(12) United States Patent
Chicca et al.

(10) Patent No.: US 10,414,721 B1
(45) Date of Patent: Sep. 17, 2019

(54) INHIBITOR OF ENDOCANNABINOID CELLULAR REUPTAKE

(71) Applicant: University of Bern, Bern (CH)

(72) Inventors: Andrea Chicca, Bern (CH); Jurg Gertsch, Court (CH)

(73) Assignee: UNIVERSITY OF BERN, Bern (CH)

( * ) Notice: Subject to any disclaimer, the term of this patent is extended or adjusted under 35 U.S.C. 154(b) by 0 days.

(21) Appl. No.: 15/996,764

(22) Filed: Jun. 4, 2018

(51) Int. Cl.
C07C 233/20 (2006.01)
A61K 31/16 (2006.01)
A61P 29/00 (2006.01)

(52) U.S. Cl.
CPC ............ C07C 233/20 (2013.01); A61K 31/16 (2013.01); A61P 29/00 (2018.01)

(58) Field of Classification Search
CPC ..... C07C 235/28; C07C 233/20; A61K 31/16; A61P 29/00
USPC .......................................... 564/143; 514/627
See application file for complete search history.

(56) References Cited

U.S. PATENT DOCUMENTS

| | | | |
|---|---|---|---|
| 6,570,036 | B1 | 5/2003 | Reuter |
| 2002/0188009 | A1 | 12/2002 | Sit et al. |
| 2003/0092734 | A1 | 5/2003 | Boger |
| 2004/0048907 | A1 | 3/2004 | Aquila et al. |
| 2004/0127518 | A1 | 7/2004 | Piomelli et al. |
| 2005/0131032 | A1 | 6/2005 | Sit et al. |

FOREIGN PATENT DOCUMENTS

| | | |
|---|---|---|
| WO | 99/16419 A1 | 4/1999 |
| WO | 01/85136 A2 | 11/2001 |

OTHER PUBLICATIONS

Karagianni et al. Pharmaceutics 2018, 10, 18; pp. 1-30.*
Chicca et al. PNAS 2017, 114(15), E5006-E5015.*
Toczek et al. Life Sci. 2018, 204: 20-45.*
Layzer, Degenerative Diseases of the Nervous System, Cecil Textbook of Medicine, 20th Edition, vol. 2, pp. 2050-2057 (1996).*
Damasio, Alzheimer's Disease and Related Dementias, Cecil Textbook of Medicine, 20th Edition, vol. 2, pp. 1992-1996 (1996).*
Freshney et al., Culture of Animal Cells, A Manual of Basic Technique, Alan R. Liss, Inc., 1983, New York, p. 4.*
Dermeret al., Bio/Technology, 1994, 12:320.*
Badea, A. et al., "Morphometric analysis of the C57BL/6J mouse brain," Neuroimage 37(3):683-693 (2007).
Batista, L. A. et al., "Inhibition of endocannabinoid neuronal uptake and hydrolysis as strategies for developing anxiolytic drugs," Behav Pharmacol 25(5-6):425-433 (2014).
Beltramo, et al., "Functional role of high-affinity anandamide transport, as revealed by selective inhibition," Science 277(5329):1094-1097 (1997).

Boger, D. L., et al., "Discovery of a potent, selective, and efficacious class of reversible α-ketoheterocycle inhibitors of fatty acid amide hydrolase effective as analgesics," J. Med. Chem. 48(6):1849-1856 (2005).
Bowes, J. et al., "Reducing safety-related drug attrition: the use of in vitro pharmacological profiling," National Reviews Drug Discovery 11(12):909-922 (2012).
Chicca, A. et al., "Chemical probes to potently and selectively inhibit endocannabinoid cellular reuptake," PNAS (USA) 114(25):E5006-E5015 (2017).
Chicca, A. et al., "Evidence for bidirectional endocannabinoid transport across cell membranes," The Journal of Biological Chemistry 287(41):34660-34682 (2012).
Chicca, A. et al., "The antinociceptive triterpene β-amyrin inhibits 2-arachidonoylglycerol (2-AG) hydrolysis without directly targeting cannabinoid receptors," British Journal of Pharmacology 167(8):1596-1608 (2012).
Cleveland Clinic, "Non-Steroidal Anti-Inflammatory Medicines (NSAIDs)," Apr. 27, 2016; available at https://my.clevelandclinic.org/health/drugs/11086-non-steroidal-anti-inflammatory-medicines-nsaids.
Fegley, D. et al., "Anandamide transport is independent of fatty-acid amide hydrolase activity and is blocked by the hydrolysis-resistant inhibitor AM1172," PNAS 101(23):8756-8761 (2004).
Hegen, M. et al . "Utility of animal models for identification of potential therapeutics for rheumatoid arthritis," Ann. Rheum. Dis. 2008, 67(11), 1505, Abstract, available at https://www.ncbi.nlm.nih.gov/pubmed/18055474.
Hillard, C.J. et al., "Accumulation of n-arachidonoylethanolamine (anandamide) into cerebellar granule cells occurs via facilitated diffusion," J. Neurochem. 69(2):631-638 (1997).
Hiller, S. et al., "α-Lipoic acid protects mitochondrial enzymes and attenuates lipopolysaccharide-induced hypothermia in mice," Free Radic Biol Med. 71:362-367 (2014).
Long, J. Z. et al., "Selective blockade of 2-arachidonoylglycerol hydrolysis produces cannabinoid behavioral effects," Nat Chem Biol.5(1):37-44 (2009).
Lutz, B., et al., "The endocannabinoid system in guarding against fear, anxiety and stress," Nat Rev Neurosci. 16(12):705-718 (2015).
Maccarrone, M. et al., "Programming and reprogramming of neural cells by (endo-) cannabinoids: from physiological rules to emerging therapies," Nat Rev Neurosci. 15(12):786-801 (2014).
Mayo Clinic, "Treating pain: Conventional medical care," Jul. 26, 2016, available at https://www.mayoclinic.org/treating-pain-conventional-medical-care/art-20208635.
Mechoulam, R., & Parker, L.A., "The endocannabinoid system and the brain," Annu Rev Psychol. 64:21-47 (2013).
Monory, K. et al., "Genetic dissection of behavioural and autonomic effects of $\Delta^9$-tetrahydrocannabinol in mice," PloS Biol. 5(10):2354-2368 (2007).

(Continued)

*Primary Examiner* — Venkataraman Balasubramanian
(74) *Attorney, Agent, or Firm* — Kilpatrick Townsend & Stockton LLP

(57) ABSTRACT

Provided is a highly potent and selective endocannabioid cellular reuptake inhibitor represented by formula (I):

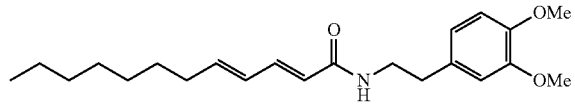

or a pharmaceutically acceptable solvate or co-crystal thereof as well as to a formulation comprising this inhibitor, and to methods of treatment in which this inhibitor is used.

14 Claims, 72 Drawing Sheets

(56) References Cited

OTHER PUBLICATIONS

Mor, M. et al., "Cyclohexylcarbamic acid 3'- or 4'-substituted biphenyl-3-yl esters as fatty acid amide hydrolase inhibitors: Synthesis, quantitative structure-activity relationships, and molecular modeling studies," J. Med. Chem. 47(21):4998-5008 (2004).
Nicolussi, S. et al., "Correlating FAAH and anandamide cellular uptake inhibition using N-alkylcarbamate inhibitors: From ultrapotent to hyperpotent," Biochem Pharmacol. 92(4):669-689 (2014).
Nicolussi, S. et al., "WOBE437—Prototype of a novel class of potent, selective endocannabinoid reuptake inhibitors," uploaded on Jun 5, 2017, available at https://www.researchgate.net/publication/271270897_WOBE437_-_Prototype_of_a_novel_class_of_potent_selective_endocannabinoid_reuptake_inhibitors.
Nicolussi, S. et al., "WOBE437—Prototype of a novel class of potent, selective endocannabinoid reuptake inhibitors," Programme Title Index: 6th European Workshop on Cannabinoid Resarch, available at https://bps.conference-services.net/programme.asp?conferenceID=3522&action=prog_titles.
Piomelli, D., & Sasso, O., "Peripheral gating of pain signals by endogenous analgesic lipids," Nat Neurosci. 17(2):164-174 (2014).
Rey, A. A. et al., "Biphasic effects of cannabinoids in anxiety responses: CB1 and GABA(B) receptors in the balance of GABAergic and glutamatergic neurotransmission," Neuropsychopharmacology 37(12):2624-2634 (2012).
Reynoso-Moreno, I. et al., "The endocannabinoid reuptake inhibitor WOBE437 is orally bioavailable and exerts indirect polypharmacological effects via different endocannabinoid receptors," Frontiers in Molecular Neuroscience 11(180):1-16 (2018).
Ruehle, S. et al., "Cannabinoid CB1 receptor in dorsal telencephalic glutamatergic neurons: Distinctive sufficiency for hippocampus-dependent and amygdala-dependent synaptic and behavioral functions," J. Neurosci. 33(25):10264-10277 (2013).
Sciencedirect, "Hot Plate Test," accessed on Dec. 3, 2018, and available at https://www.sciencedirect.com/topics/neuroscience/hot-plate-test.
Sciencedirect, "Nonsteroid Antinflammatory Agent," accessed Dec. 3, 2018, and available at https://www.sciencedirect.com/topics/medicine-and-dentistry/nonsteroid-antiinflammatory-agent.
Smith, P. K. et al., "Measurement of protein using bicinchoninic acid," Anal Biochem. 150(1):76-85 (1985).
Du, W. et al., "Heterocyclic sulfoxide and sulfone inhibitors of fatty acid amide hydrolase," Bioorganic & Medicinal Chemistry Letters 15(1):103-106 (2005).
Fischer, H. et al., "Permeation of permanently positive charged molecules through artificial membranes—influence of physicochemical properties," Eur J Pharm Sci. 31(1):32-42 (2007).
Nicolussi, S. et al., "Guineensine is a novel inhibitor of endocannabinoid uptake showing cannabimimetic behavioral effects in BALB/c mice," Pharmacol Res. 80:52-65 (2014).
Nicolussi, S., & Gertsch, J., "Endocannabinoid transport revisited," Vitam Horm. 98:441-485 (2015).
Rau, M. et al., "Assay of endocannabinoid uptake," Methods Mol Biol. 1412:191-203 (2016).
Romanovsky, A. A. et al., "Endotoxin shock: Thermoregulatory mechanisms," Am J Physiol. 270(4 Pt 2):R693-703 (1996).

* cited by examiner

|  | Mouse | Human |
|---|---|---|
| Clearance | 174 µL/min/kg | 657 µL/min/kg |
| MAB | 17% | 4% |

FIG. 6

INHIBITOR OF ENDOCANNABINOID CELLULAR REUPTAKE

BACKGROUND OF THE INVENTION

The endocannabinoid system (ECS) is a pan-organ lipid signaling network that modulates numerous biological processes, including neurotransmission and immune function (Maccarrone 2014). The major endogenous agonists (i.e., endocannabinoids, ECs) for cannabinoid receptors CB1 and CB2 are the arachidonic acid (AA)-derived lipids 2-arachidonoyl glycerol (2-AG) and N-arachidonoylethanolamine (anandamide, AEA). Altered endocannabinoid signaling in the brain has been implicated in nociception, learning and memory, anxiety, and depression (Piomelli 2014, Mechoulam 2013, Lutz 2015). The indirect modulation of endocannabinoid levels may lead to less side effects than the direct activation of CB1 receptors in terms of neurotransmission, metabolism and immunomodulation.

CB1 receptor agonists are intrinsically associated with strong central side effects that are far less pronounced for increasing endocannabinoid levels upon blockage of the main endocannabinoid hydrolytic enzymes fatty acid amide hydrolase (FAAH) and monoacylglycerol lipase (MAGL). In addition to general anti-inflammatory and analgesic effects, the modulation of endocannabinoid tissue concentrations is a promising therapeutic approach to treat diseases related to the central nervous system (CNS) (Lutz 2015). Pharmacological strategies to treat neuropsychiatric disorders currently focus on the inhibition of endocannabinoid degradation (Batista 2014). FAAH and MAGL inhibitors such as URB597 and JZL184, respectively, have been instrumental to elucidate the role of anandamide and 2-arachidonoyl glycerol in rodent models of anxiety and depression, (Nicolussi&Gertsch 2015). Although anandamide and 2-arachidonoyl glycerol have different intracellular fates, they may share a common mechanism of membrane trafficking that is selective for endocannabinoids over arachidonate and other N-acylethanolamines (NAEs) (Chicca 2012, Beltramo 1997, Hillard 1997, Fegley 2004). However, while suitable inhibitors are available for most targets within the endocannabinoid system, the existing anandamide uptake inhibitors lack potency and show poor selectivity over the other components of the endocannabinoid system, in particular FAAH (Nicolussi&Gertsch 2015).

Current uptake inhibitors are poorly bioavailable to the central nervous system (CNS) and weakly selective because they also inhibit FAAH, the major anandamide-degrading enzyme. Few studies have addressed the uptake inhibition of 2-AG, which is the major endocannabinoid. Thus, more potent and more selective inhibitors are necessary to provide pharmaceutically useful inhibitors.

BRIEF SUMMARY OF THE INVENTION

In one aspect, provided is a compound of formula (I):

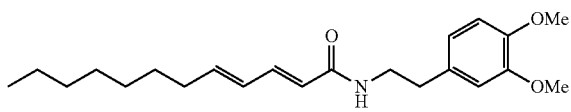 [SMILES: CCCCCCC/C=C/C=C/C(=O)NCCc1ccc(OC)c(OC)c1]

or a pharmaceutically acceptable solvate or co-crystal thereof.

Such compounds are inhibitors of endocannabinoid cellular reuptake.

It is to be understood that any reference to the compound of formula (I) also represents a reference to a pharmaceutically acceptable solvate or co-crystal of the compound of formula (I).

In another aspect, provided is a method of treating a mammal suffering from a disease, disorder, or condition by administering to said mammal a therapeutically effective amount of a compound of formula (I) or a pharmaceutically acceptable solvate or co-crystal thereof.

DESCRIPTION OF FIGURES

FIGS. 1A-1H are based on the data described in detail in Proc. Natl. Acad. Sci. USA. 2017, 114(25), pages E5006-E5015 and the supplementary information of this publication.

FIG. 1A: Chemical structures of a selection of dodeca-2E,4E-dienoyl N-alkylamides (and $IC_{50}$ values for anandamide uptake.

FIG. 1B: $IC_{50}$ values for anandamide uptake and hydrolysis inhibition for the most potent N-alkylamides and reference compounds (FAAH inhibitors are in green, anandamide uptake inhibitors are in blue). No significant correlation between these two processes (indicated with the grey dotted line) was observed (Pearson's $\rho=0.258$, $p=0.214$, not significant ($\alpha=0.05$)). WOBE437 (red) shows exceptional potency for anandamide uptake inhibition and selectivity over FAAH inhibition.

FIG. 1C: Inhibition of anandamide uptake by WOBE437 in Neuro2a cells. The curves were normalized.

FIG. 1D: Inhibition of anandamide and 2-arachidonoyl glycerol uptake induced by WOBE437 in U937 cells (multiphase assay format). Data show mean values±SEM from ten independent experiments performed in triplicate. The curves were normalized.

FIG. 1E: Time-course of anandamide uptake in Neuro2a cells in presence of WOBE437 (1 µM) or vehicle. Statistical significance was calculated with two-tailed unpaired t-test. **$p<0.01$, *$p<0.05$ vs. vehicle.

FIG. 1F: Time-course of anandamide uptake in Primary mouse cortical neurons in presence of WOBE437 (1 µM) or vehicle. Statistical significance was calculated with two-tailed unpaired t-test. **$p<0.01$, *$p<0.05$ vs. vehicle.

FIG. 1G: Time-course of 2-arachidonoyl glycerol uptake in Neuro2a cells in presence of WOBE437 (5 µM) or vehicle.

FIG. 1H: WOBE437 does not inhibit any of the major serine hydrolases in membranes obtained from mouse brain (ABPP experiment). URB597, JZL184, JZL195 and WWL70 were used as positive controls for FAAH, MAGL, dual FAAH/MAGL and ABHD6 inhibition, respectively. Data show mean values±SD from at least three independent experiments performed in triplicate.

FIGS. 2A-2G are based on the data described in detail in Proc. Natl. Acad. Sci. USA. 2017, 114(25), pages E5006-E5015 and the supplementary information of this publication.

FIGS. 2A-D: Different initial amounts of $^{14}$C-WOBE437 were incubated for 15 min with 1×10$^6$ of U937 cells at 37° C. Afterwards, cells were centrifuged and the $^{14}$C-signal was measured from the extracellular (light grey), membrane-bound (dark grey) and intracellular (white) fraction. The results are reported in absolute amounts and as percentage of the initial amount.

FIG. 2E: Binding kinetics of $^{14}$C-WOBE437 using membrane preparation of mouse brain and cells.

FIG. 2F: Binding kinetics of $^{14}$C-WOBE437 using membrane preparation of U937 cells. In U937 membranes, $^{14}$C-WOBE437 was co-incubated with vehicle or different concentrations of anandamide.

FIG. 2G: Competitive inhibition of anandamide cellular uptake in U937 cells as shown by Michaelis-Menten analysis. Data shown are mean values±SD from at least three independent experiments.

FIGS. 3A-3J are based on the data described in detail in Proc. Natl. Acad. Sci. USA. 2017, 114(25), pages E5006-E5015 and the supplementary information of this publication.

FIG. 3A-3D: Concentration-dependent WOBE437-induced hypothermia, hypolocomotion, catalepsy and analgesia (tetrad) in BALB/c mice. The tetrad was assessed after 1 h from WOBE437 injection (i.p.). Hypothermia, catalepsy and analgesia were fully blocked by pre-treating the animals for 30 min with SR1, while hypolocomotion was only partially reversed.

FIG. 3E: WOBE437 (10 mg/kg) reduces the number of abdominal stretches in the acetic acid-induced writhing test. This analgesic effect is prevented by pre-treatment with SR1. Indomethacin (5 mg/kg) is shown as reference analgesic drug.

FIG. 3F: WOBE437 (5 mg/kg) exerted protective effects in the LPS-induced drop of rectal temperature, which is a consequence of endotoxemia. The protective effect is inhibited by pre-treatment with SR1.

FIGS. 3G-3H: Analgesic and anti-inflammatory effects of WOBE437 during the second phase of formalin-induced pain and inflammatory responses. Indomethacin (5 mg/kg) is shown as reference analgesic drug.

FIG. 3I: Anxiolytic effects of WOBE437 in the elevated plus-maze test performed in C57BL6/N mice. The data show mean values±SEM. Groups were compared to the vehicle treated control group or as indicated by arcs using a one-way (a-e and g-i) or two-way (f) ANOVA following Bonferroni's post-hoc test or unpaired t-test (g-j). n=5-20 mice per group. *p<0.001, p<0.01, *p<0.05, ns=not significant. All doses are indicated in mg/kg, i.p.

FIG. 3J: Anxiolytic effects of WOBE437 in the holeboard test performed in C57BL6/N mice. The data show mean values±SEM. Groups were compared to the vehicle treated control group or as indicated by arcs using a one-way (a-e and g-i) or two-way (f) ANOVA following Bonferroni's post-hoc test or unpaired t-test (g-j). n=5-20 mice per group. *p<0.001, p<0.01, *p<0.05, ns=not significant. All doses are indicated in mg/kg, i.p.

FIGS. 4A-4H are based on the data described in detail in Proc. Natl. Acad. Sci. USA. 2017, 114(25), pages E5006-E5015 and the supplementary information of this publication.

FIGS. 4A-4D: Plasma concentrations of WOBE437, anandamide, 2-arachidonoyl glycerol and corticosterone measured at different time points post-treatment with 10 mg/kg (i.p., single injection and repeated administrations, once daily for 7 days) in C57BL6/J mice. Data represent means±SD; n=5 mice per group. Statistical analysis was performed using one-way ANOVA to compare distinct groups of animals injected with DMSO or WOBE437 and sacrificed at different time points. At every time point, DMSO- and WOBE437-treated animals were compared using two-tailed unpaired t-test *p<0.001, p<0.01 *p<0.05 WOBE437 vs. vehicle; ##p<0.01, #p<0.05 vs. baseline (time 0); +p<0.05, ++p<0.01 repeated administration vs. single administration (at 60 min post-injection).

FIGS. 4E-4H: Brain concentrations of WOBE437, anandamide, 2-arachidonoyl glycerol and corticosterone measured at different time points post-treatment with 10 mg/kg (i.p., single injection and repeated administrations, once daily for 7 days) in C57BL6/J mice. Data represent means±SD; n=5 mice per group. Statistical analysis was performed using one-way ANOVA to compare distinct groups of animals injected with DMSO or WOBE437 and sacrificed at different time points. At every time point, DMSO- and WOBE437-treated animals were compared using two-tailed unpaired t-test *p<0.001, p<0.01 *p<0.05 WOBE437 vs. vehicle; ##p<0.01, #p<0.05 vs. baseline (time 0); +p<0.05, ++p<0.01 repeated administration vs. single administration (at 60 min post-injection).

FIG. 5A: After 20 min post-gavage, WOBE437 was dose-dependently absorbed and reached quantitative concentrations in brain and plasma (right and left columns, respectively, for each condition). Data show mean values±SD of 5-10 mice.

FIG. 5B: Time course of WOBE437 concentration in brain and plasma showing a presumed $T_{max}$ of 10-20 min after administration. Data show mean values±SD of 5-10 mice.

FIG. 5C: Time course of WOBE437 concentrations in kidney, liver and spleen, showing the highest concentrations in liver 20 min after administration. p.o., per os. Data show mean values±SD of 5-10 mice.

FIG. 6. Clearance of WOBE437 calculated after incubation for 2 h with human and mouse liver microsomes. The maximal achievable bioavailability (MAB) was estimated from the clearance.

FIG. 7A: Dose-response curve of WOBE437 in the pain latency response in the hot-plate test. 50 mg/kg of WOBE437 p.o. was the minimum dose to significantly increase pain threshold.

FIG. 7B: The analgesic effect of 50 mg/kg and 100 mg/kg of WOBE437 was completely abolished by pre-treatment with rimonabant (5 mg/kg). All doses are expressed in mg/kg. Rimonabant was injected i.p. 30 min before gavage administration of WOBE437. Data show mean values±SD of 5-10 mice. Data were compared using Kruskal-Wallis test followed by Mann-Whitney test. *, p<0.05 vs vehicle; #, p<0.05 vs WOBE437. p.o. per os; ns, no significant.

FIGS. 8A-8D: Change in body temperature (B) latency of catalepsy, (C) locomotion and (D) latency of pain response 1 h after gavage administration of vehicle or 50 mg/kg of WOBE437. Data show mean values±SD of 5 mice. Data were compared using Mann-Whitney test. *, p<0.05 vs vehicle.

FIGS. 9A-9B: In somatosensory cortex, WOBE437 did not change 2-AG levels (FIG. 9A) but significantly increased AEA levels (FIG. 9B) with a single 50 mg/kg dose.

FIG. 9C: Concentration of WOBE437 in somatosensory cortex.

FIGS. 9D-9E show graphs illustrating that 2-AG and AEA, respectively, did not significantly change in total brain homogenate after oral administration of a single dose of 50 mg/kg of WOBE437.

FIG. 9F: Concentration of WOBE437 in total brain homogenate.

FIGS. 9G-9H: 2-AG levels were significantly increase in plasma (FIG. 9G) with a slightly decrease in AEA (FIG. 9H).

FIG. 9I: Concentration of WOBE437 in plasma. All Data show mean values±SD of at least 5 to 10 mice. Groups were compared using Kruskal-Wallis test followed by Mann-Whitney test. *, $p<0.05$ vs vehicle. 2-AG, 2-arachidonoyl-glycerol; AEA, anadamide; p.o. per os.

FIGS. 10A-10C show graphs illustrating Palmitoylethanolamide (PEA), oleoylethanolamine (OEA), and linoleoylethanolamide (LEA) levels in somatosensory cortex, respectively.

FIGS. 10D-F show graphs illustrating PEA, OEA, and LEA levels in total brain homogenate, respectively.

FIG. 10G-10I show PEA, OEA, and LEA levels in plasma, respectively. Data shows mean±SD for at least 5 to 10 mice. Groups were compared using Kruskal-Wallis test followed by Mann-Whitney test. *, $p<0.05$ vs vehicle. LOQ, limit of quantification; p.o. per os.

FIG. 11A: Treatment scheme of monoarthritis induced by knee immunization with complete Freund's adjuvant (CFA) (40 µL, intra-articular) in which the inflammatory process was allowed to develop for 14 days. Intraperitoneal treatments with WOBE437 were carried on days 15 to 17.

FIG. 11B: Allodynia was evaluated upon single dose treatments in which 10 mg/kg of WOBE437 increased the pain threshold.

FIGS. 11C-11D show improved allodynia and reduced edema, respectively, after 3 days of treatment, 10 mg/kg of WOBE437.

FIG. 11E: The development of monoarthritis significantly decreased the travel distance in the open field test, but no significant changes were observed after WOBE437 treatment due to high variability. Indomethacin was used as a reference drug. All doses are shown in mg/kg i.p. Allodynia was evaluated by mechanical sensitivity and edema through knee diameter, both were measured 1 h after pharmacological treatments. All data show mean values±SD of at least 6 to 15 mice. Groups were compared using Kruskal-Wallis test followed by Mann-Whitney test. *, $p<0.05$ vs ipsilateral/vehicle; #, $p<0.05$ vs contralateral/healthy; i.p. intraperitoneally.

FIG. 12A: Anti-allodynia effects of single dose of WOBE437 (10 mg/kg, i.p.) were significantly mediated by CB2 receptor antagonist SR144528 and TRPV1 antagonist Capsazepine.

FIGS. 12B-12C: In the 3 days treatment scheme, (FIG. 12B) anti-allodynia and (FIG. 12C) anti-inflammatory effect were prevented by antagonists to CB1r rimonabant, CB2r SR144528 and PPARγ GW9662. Rimonabant, SR144528 or GW9662 were administered 30 min before WOBE437 injection(s). Allodynia was evaluated by mechanical sensitivity and edema through knee diameter, both were measured 1 h after WOBE437 injection. All compounds were administered i.p. Groups were compared using Kruskal-Wallis test followed by Mann-Whitney test. *, $p<0.05$ vs ipsilateral/vehicle; #, $p<0.05$ vs contralateral/vehicle; &, $p<0.05$ vs WOBE437; i.p. intraperitoneally.

FIGS. 13A-13C: Total RNA levels of cannabinoid CB1 receptor (Cnr1), cannabinoid CB2 receptor (Cnr2) N-acyl-phosphatidylethanolamine specific phospholipase D (Nape-pld) and diacylglycerol lipase (Dagla) did not show any significant changes in (FIG. 13A) somatosensory cortex, (FIG. 13B) thalamus or (FIG. 13C) articular tissue. Beta-actin was used as housekeeping gene and mean values in vehicle group as a calibrator mRNA levels were determined by RT-PCR. All data show median, percentile 75, percentile 25, min. and max of at least 6 to 15 mice. Groups were compared using Kruskal-Wallis test followed by Mann-Whitney test. *, $p<0.05$ vs ipsilateral/vehicle.

Figure 1A:
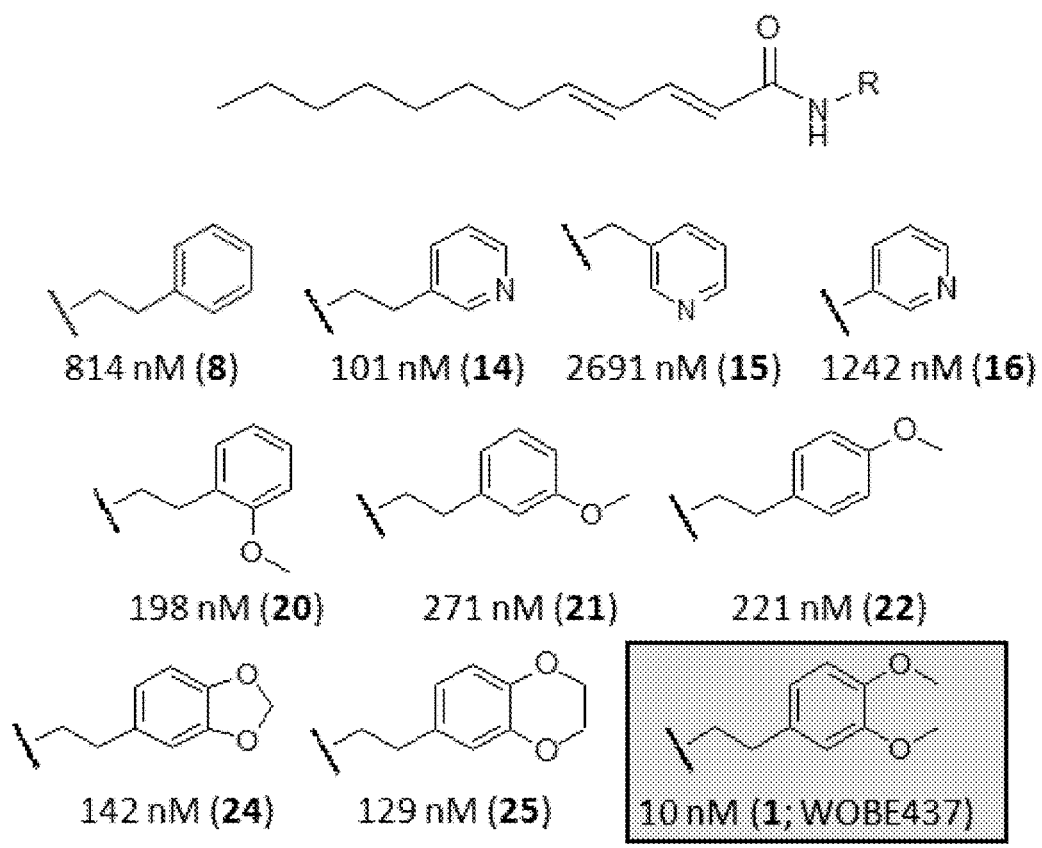
FIGS. 1A-1H. Design and in vitro pharmacological characterization of the highly potent and selective endocannabinoid transport inhibitor WOBE437.

The development of the compound of formula (I), which is hereinafter also referred to as WOBE437, has been described by the present inventors in Proc. Natl. Acad. Sci. USA. 2017, 114(25), pages E5006-E5015, which is hereby incorporated by reference in its entirety including the Supplementary Information. Further investigations regarding WOBE437 and its activities have been published by the present inventors in Reynoso-Moreno I et al., Front. Mol. Neurosci., 28 May 2018 (https://doi.org/10.3389/fnmol.2018.00180) with the title "The Endocannabinoid Reuptake Inhibitor WOBE437 Is Orally Bioavailable and Exerts Indirect Polypharmacological Effects via Different Endocannabinoid Receptors" which is hereby also incorporated by reference in its entirety including the Supplementary Information.

DETAILED DESCRIPTION OF THE INVENTION

The present invention relates to a highly potent and selective endocannabinoid cellular reuptake inhibitor and to methods of treatment of various diseases such as selected from asthma, neuropathic pain, peripheral pain; persistent pain, inflammatory pain, epilepsy, hyperactivity, cardiovascular diseases and blood pressure disorders such as hypertension, brain ischemia, spasticity, to prevent or reduce diseases associated with motor function such as Tourette's syndrome; chronic inflammatory diseases; schizophrenia, haemorrhagic shock, septic shock, cardiac shock, migraine, Horton's headache, anorexia, AIDS wasting syndrome, organ rejection, autoimmune diseases, allergy, arthritis, Crohn's disease, colitis, malignant gliomas, neurodegenerative diseases including multiple sclerosis, Parkinson's Disease, Huntington's Chorea and Alzheimer's Disease, amyotrophic lateral sclerosis, nausea such as associated with cancer chemotherapy; anxiety, psychosis, panic attack, sleep disorders, attention deficit hyperactivity disorder, premature ejaculation, and stroke, and to provide neuro-protection; stress and mood disorders such as post-traumatic stress disorders, depressive disorders, bipolar disorders, chronic stress, to produce peripheral vasodilation, to suppress memory, to enhance appetite and to reduce fertility. Further indications include the treatment of substance of abuse disorders, in particular alcohol use disorder (AUD), tobacco use disorder (TUD), Cannabis use disorder (CAB), opioid use disorder, stimulant use disorder and hallucinogen use disorder. Still further indications include the treatment of alcohol-related liver disease, non-alcoholic fatty liver disease, hepatic ischaemia-reperfusion injury, liver fibrosis, hepatitis, primary biliary cirrhosis, primary sclerosing cholangitis, chronic kidney disease, diabetic kidney disease and kidney ischaemia-reperfusion injury. The compounds of the present invention may further be used in the treatment of skin diseases such as psoriasis, atopic dermatitis, systemic scleroderma, severe itching or pruritus associated with different causes. The compounds of the present invention may further be used in the treatment of eye diseases such as uveitis, conjunctivitis, scleritis, keratitis and other inflammatory and immunological disorders of different origins; glaucoma of different origins; retinopathies of different origins.

Unless defined otherwise, all technical and scientific terms used herein have the same meanings as commonly understood by one of ordinary skill in the art to which this invention belongs.

The term "preferably" is used to describe features or embodiments which are not required in the present invention but may lead to improved technical effects and are thus desirable but not essential.

In one aspect, provided is a compound represented by formula (I):

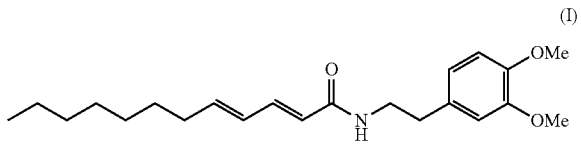 [SMILES: CCCCCCC/C=C/C=C/C(=O)NCCc1ccc(OC)c(OC)c1]

(I)

or a pharmaceutically acceptable solvate or co-crystal thereof. Such compounds are inhibitors of endocannabinoid cellular reuptake.

In general, the term "cannabinoid reuptake inhibitor" refers to compounds that decrease the reuptake of endogenous cannabinoids into neurons or decrease the enzymatic breakdown of endogenous cannabinoids in extracellular space, including synaptic clefts. Furthermore, as defined herein, the cannabinoid reuptake inhibitor of formula (I) is a strong inhibitor of fatty acid amide hydrolase, with a half-maximal inhibitory concentration ($IC_{50}$) of much less than 5 µM. This half-maximal inhibitory concentration can be measured using a radiolabeled anandamide assay described by Mor (Mor et al., (2004) J. Med. Chem. 47(21): 4998-5008).

A "solvate" refers to an association or complex of one or more solvent molecules and the compound of formula (I). Examples of solvents that form solvates include, but are not limited to, water, isopropanol, ethanol, methanol, dimethyl sulfoxide (DMSO), ethyl acetate, acetic acid, and ethanolamine. The term "hydrate" refers to the complex where the solvent molecule is water.

A "co-crystal" refers to a crystalline structure that contains at least two different compounds that are solid in their pure form under ambient conditions. Co-crystals are made from neutral molecular species, and all species remain neutral after crystallization; further, typically and preferably, they are crystalline homogeneous phase materials where two or more building compounds are present in a defined stoichiometric ratio. See hereto Wang Y and Chen A, 2013; and Springuel G R, et al., 2012; and U.S. Pat. No. 6,570,036.

The development of the compound of formula (I), which is hereinafter also referred to as WOBE437, has been described by the present inventors in Proc. Natl. Acad. Sci. USA. 2017, 114(25), pages E5006-E5015, which is hereby incorporated by reference in its entirety including the Supplementary Information.

Generally known examples of cannabinoid reuptake inhibitors, include amines as described in US Patent Application 2004/0048907, specifically including the compounds N-(4-hydroxyphenyl)arachidonamide (AM404), N-(5Z, 8Z, 11Z, 14Z eicosatetraenyl)-4-hydroxybenzamide (AM1172), and N-(2-methyl-4-hydroxy-phenyl)-arachidonamide (VDM11); the compound cyclohexylcarbamic acid 3'-carbamoylbiphenyl-3-yl ester (URB-597, described in Mor et al., (2004) J. Med. Chem. 47(21): 4998-5008); as well as fatty acid amide hydrolase (FAAH) inhibitors such as those described in US Patent Application Nos. 20040127518, 20050131032, 20030092734, and 20020188009, and literature publications (Beltramo et al. (1997) Science 277: 1094-1097; Fegley et al. (2004) Proc. Natl. Acad. Sci. USA 101(23): 8756-61; Du et al. (2005) Bioorganic & Medicinal Chemistry Letters 15(1): 103-106; Boger et al., (2005) J. Med. Chem. 48(6): 1849-1856). The compound of formula (I) of the present invention is both a more potent and more selective inhibitor of endocannabinoid cellular reuptake than these cannabinoid reuptake inhibitors.

Figure 1B:
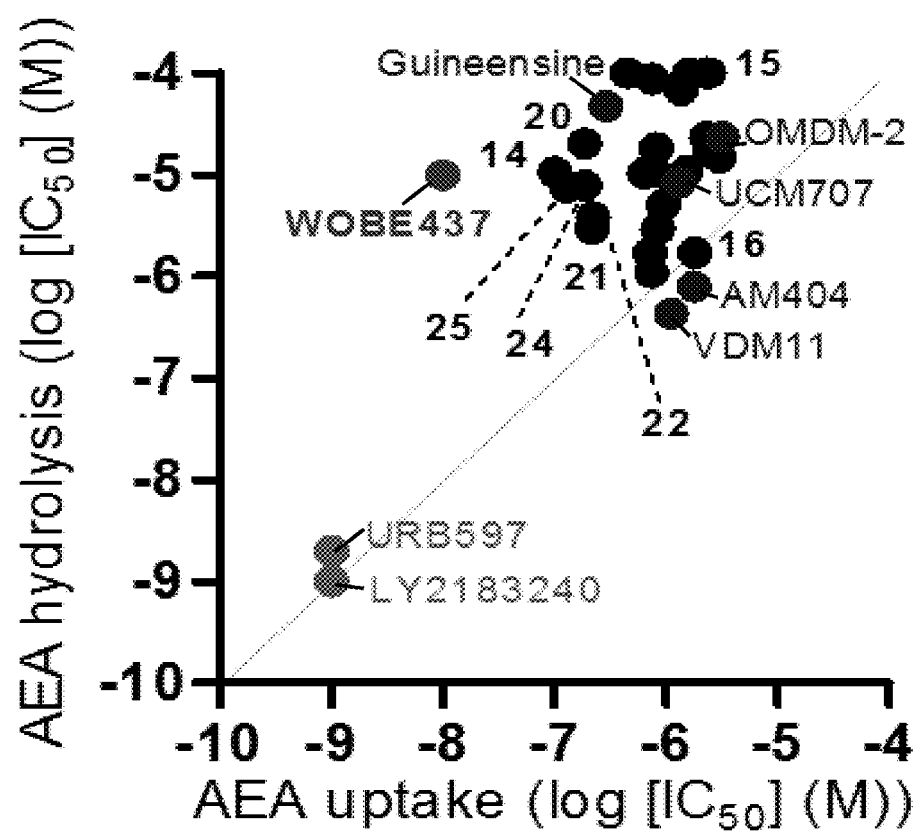
Figure 1C:
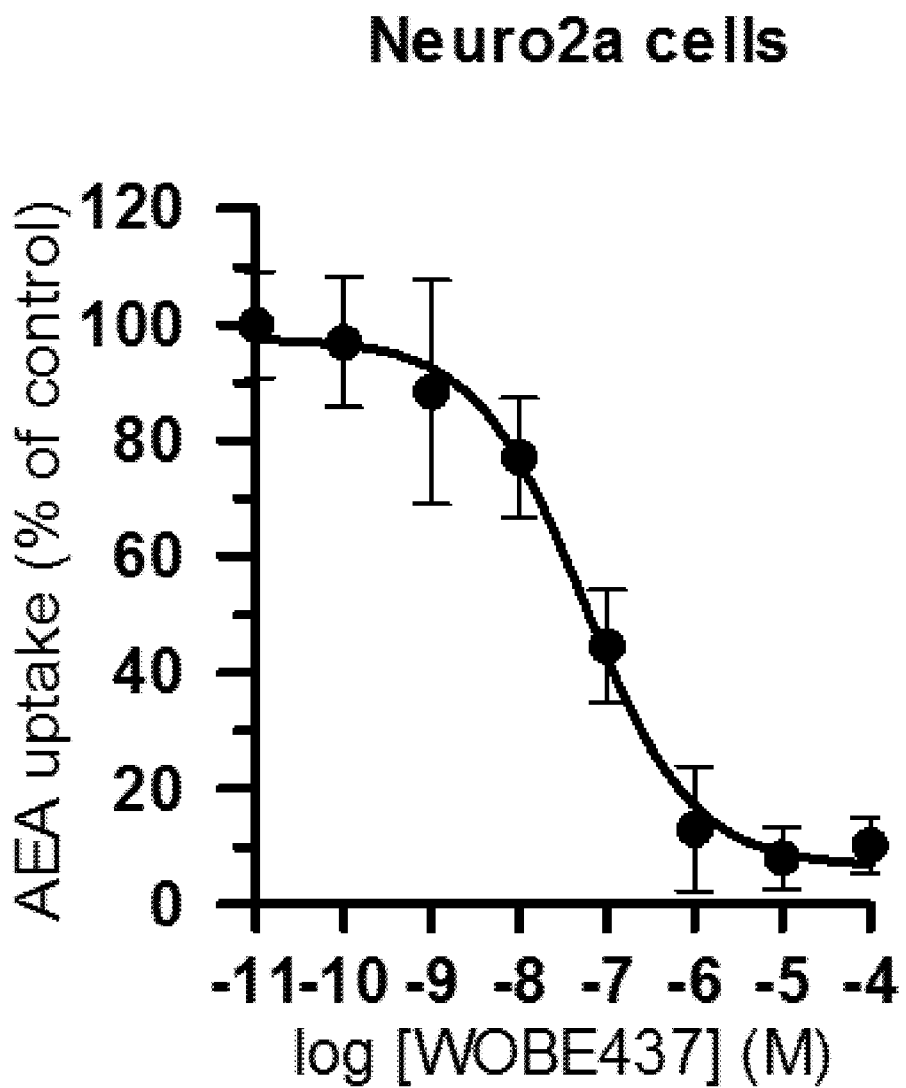
Figure 1D:
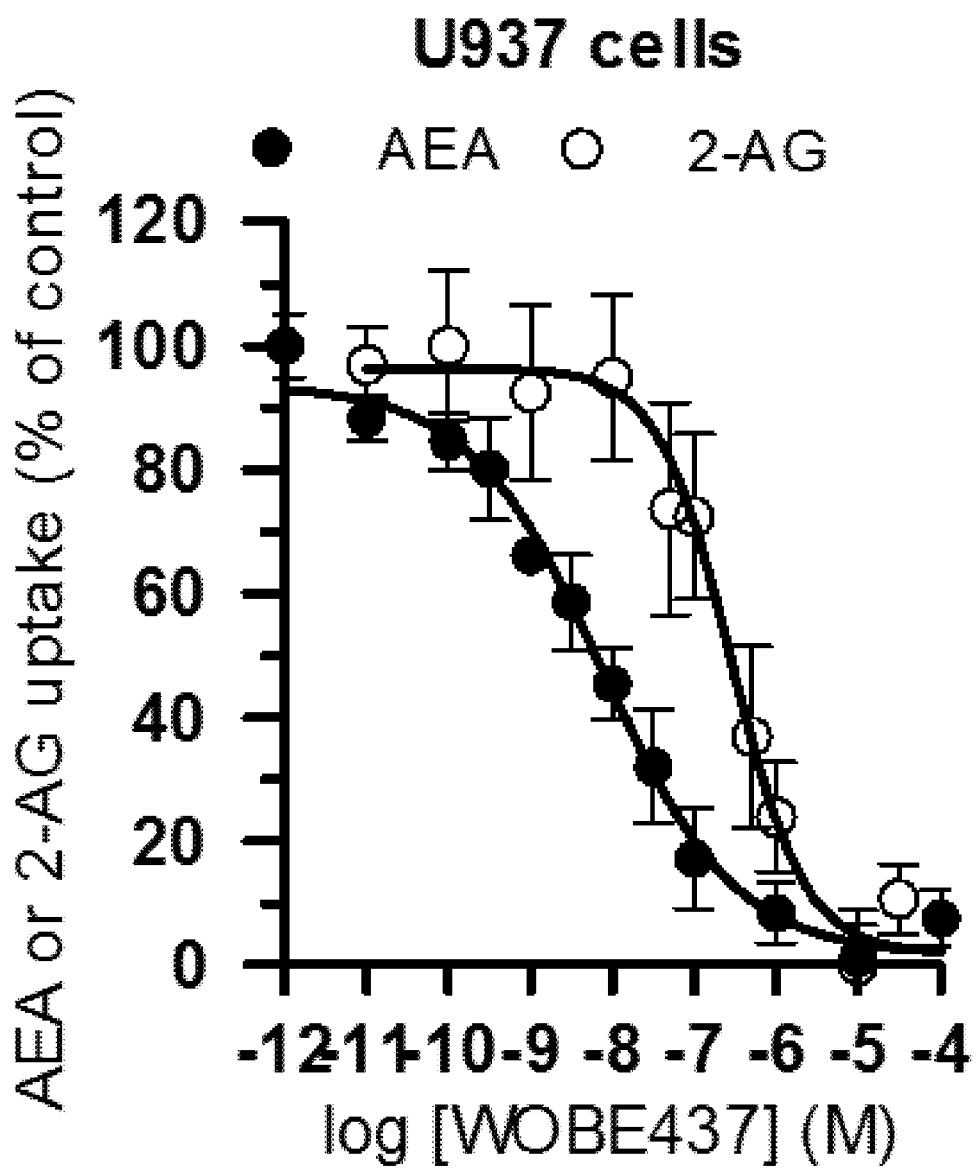

The present inventors have thoroughly investigated the effects of WOBE437 on anandamide uptake and the inhibition of FAAH as shown in FIG. 1a. WOBE437 exhibits dramatically improved selectivity for anandamide uptake reduction over FAAH inhibition, as compared to any previously described non-selective and cell-permeable anandamide uptake inhibitors (FIG. 1b). Furthermore, the lack of significant FAAH inhibition by WOBE437 has been established in different assay systems using human recombinant enzyme, cell and brain homogenates. Accordingly, this compound does not significantly inhibit anandamide hydrolysis in any biological matrices investigated, which can be seen from the fact that the $IC_{50}$ is at least 10 µM. On the other hand, WOBE437 showed low nanomolar potency for the inhibition of anandamide uptake in different cell lines and assay formats (FIG. 1d).

Figure 1E:
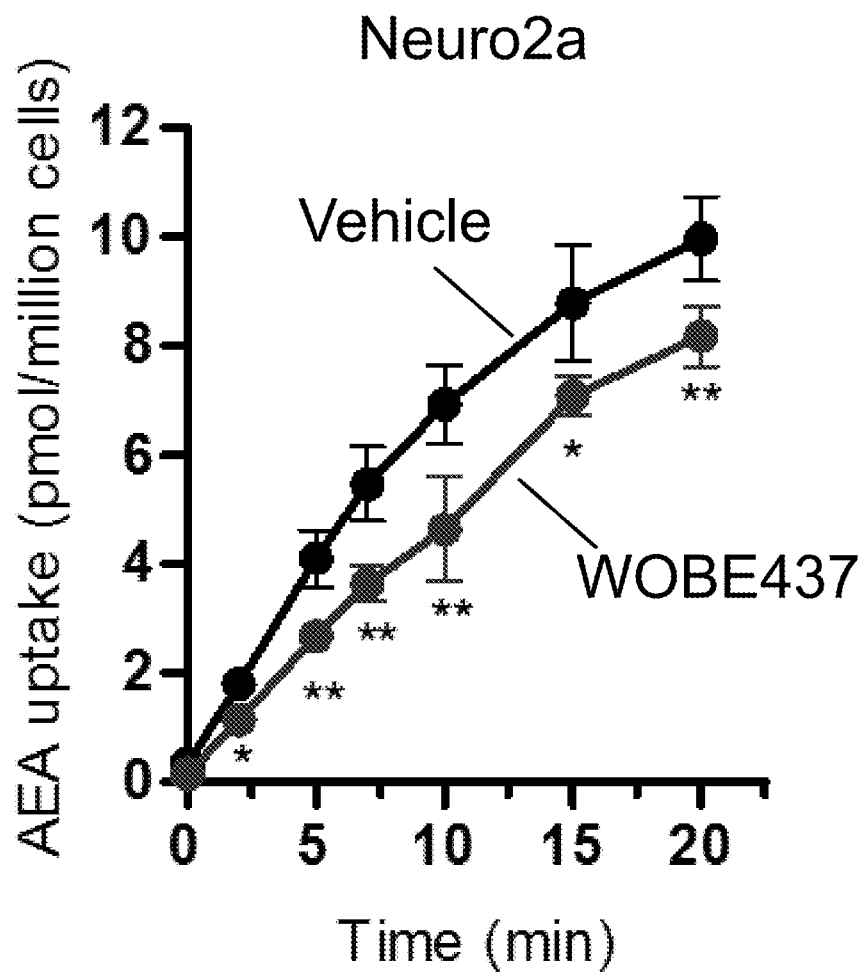
Figure 1F:
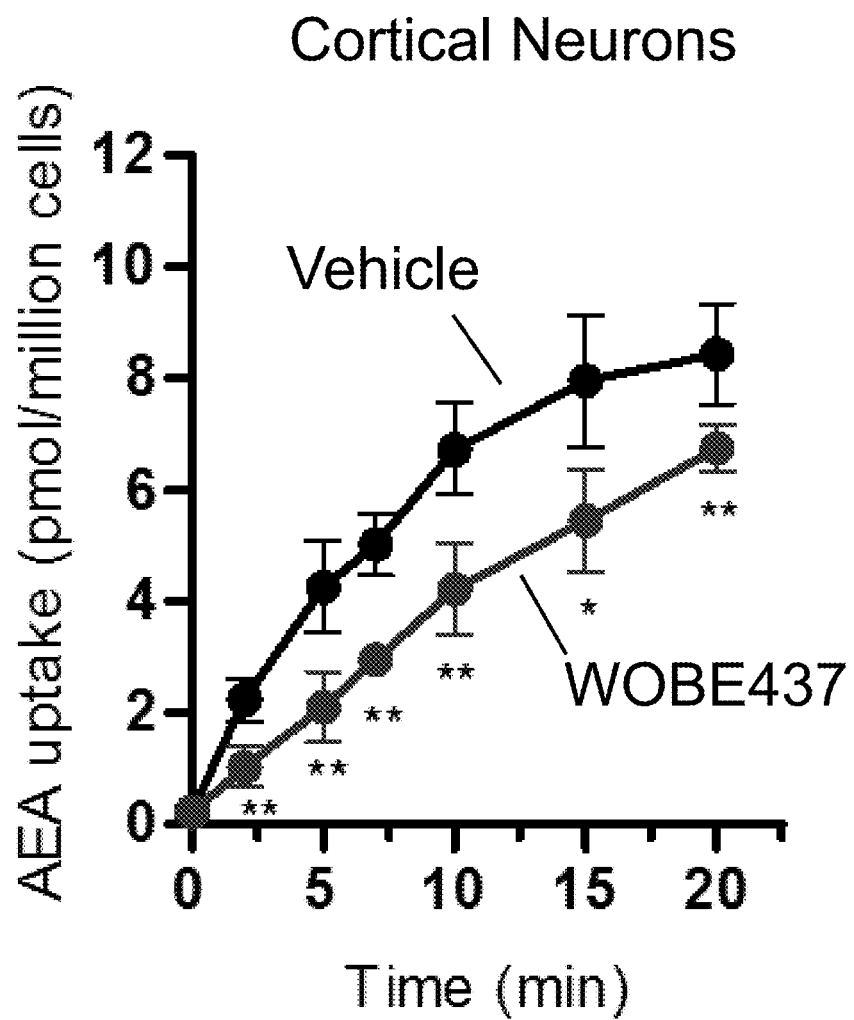
Figure 1G:
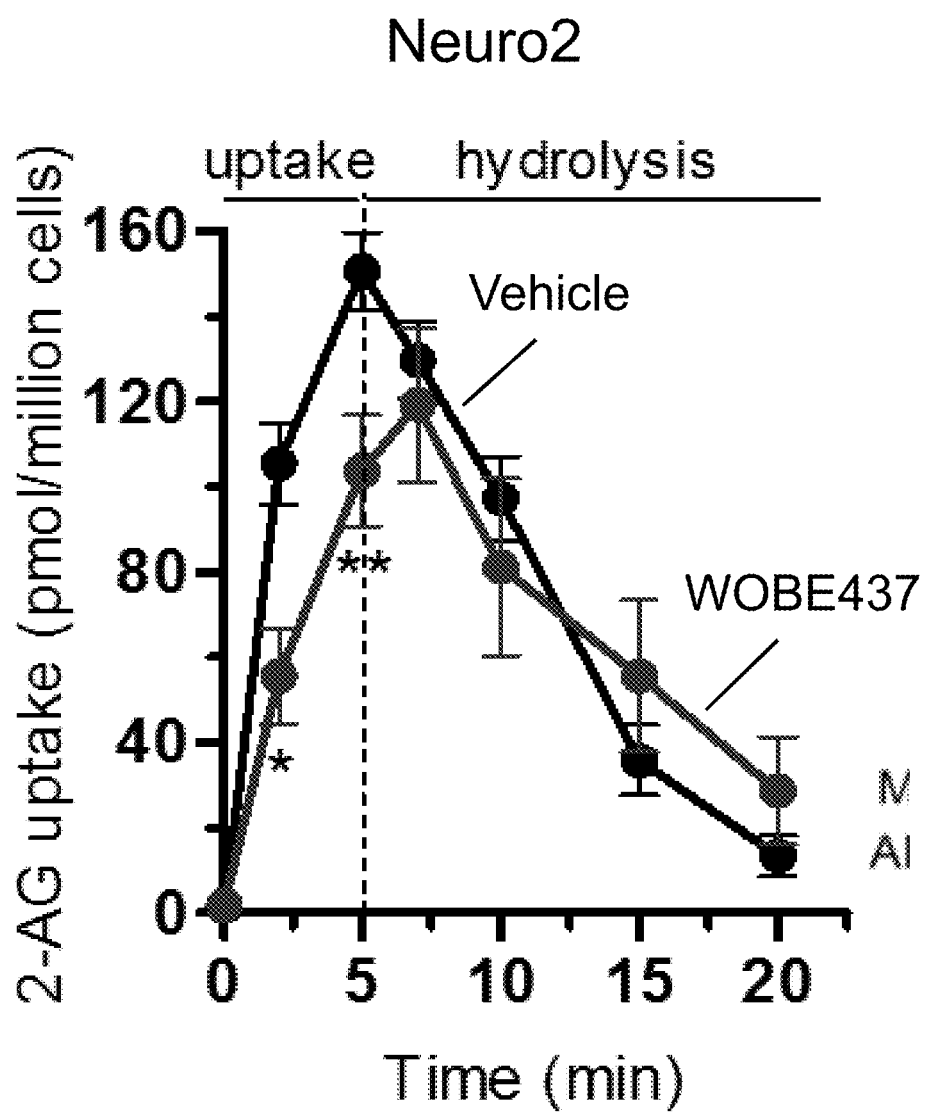
Figure 1H:
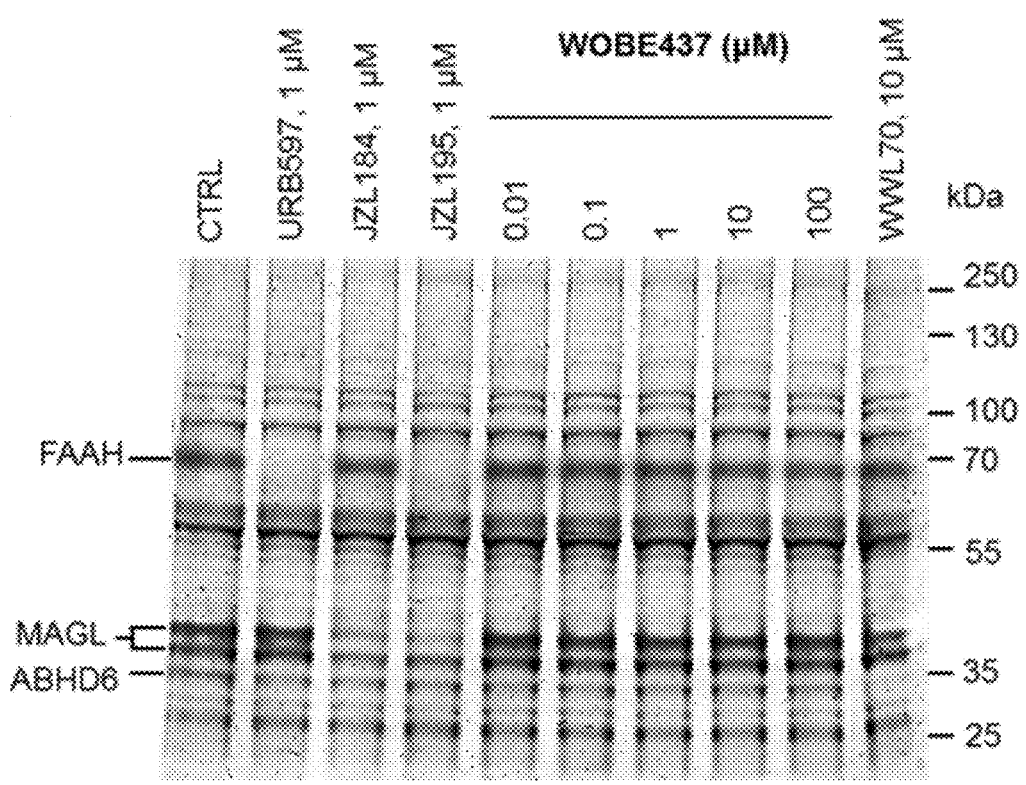

In addition, the present inventors found that WOBE437 strongly inhibits 2-arachidonoyl glycerol uptake but not hydrolysis (FIG. 1g). In agreement with the hydrolase activity-based protein profiling (ABPP) in mouse brain homogenate (FIG. 1h) and of classical radioactivity-based hydrolytic assays in other biological matrices, WOBE437 does not inhibit any of the 2-arachidonoyl glycerol hydrolyzing enzymes MAGL, ABHD6, and ABHD12. Importantly, WOBE437 is stable in the presence of the main endocannabinoid degrading enzymes. Furthermore, it does not inhibit COX-2 activity and exhibits no binding to fatty acid binding protein 5 (FABP5)

Figure 4A:
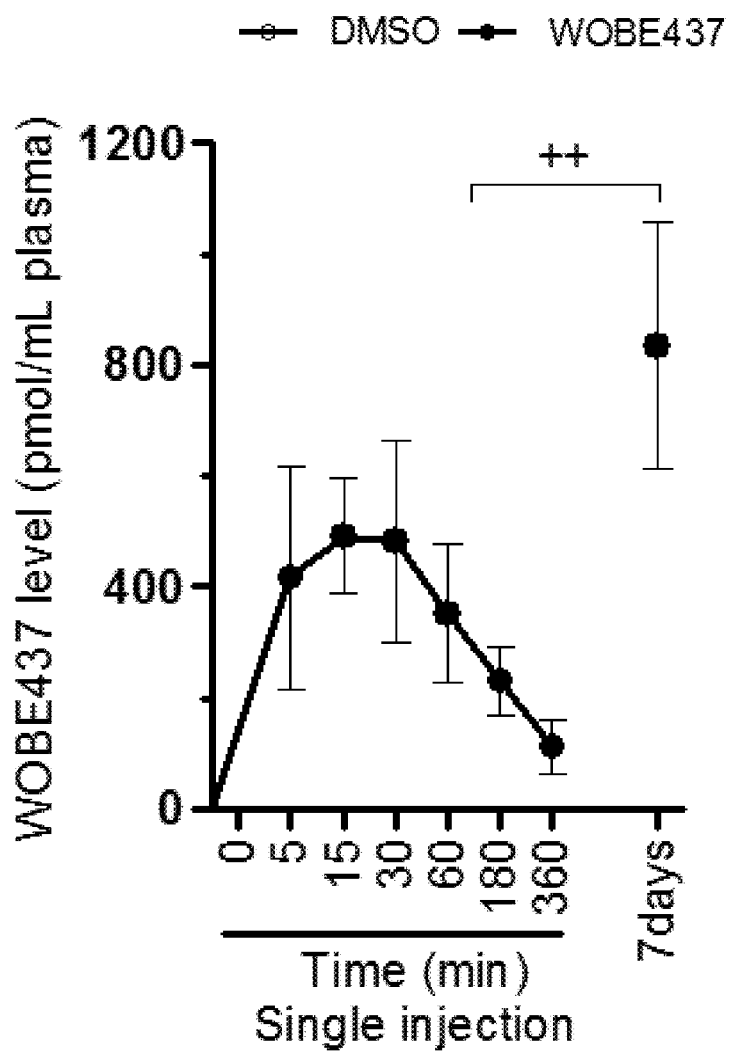
FIGS. 4A-4H. LC-MS/MS quantification of WOBE437, anandamide, 2-arachidonoyl glycerol and corticosterone in brain and plasma of C57BL6/J mice treated with 10 mg/kg of WOBE437 for different times.
Figure 4B:
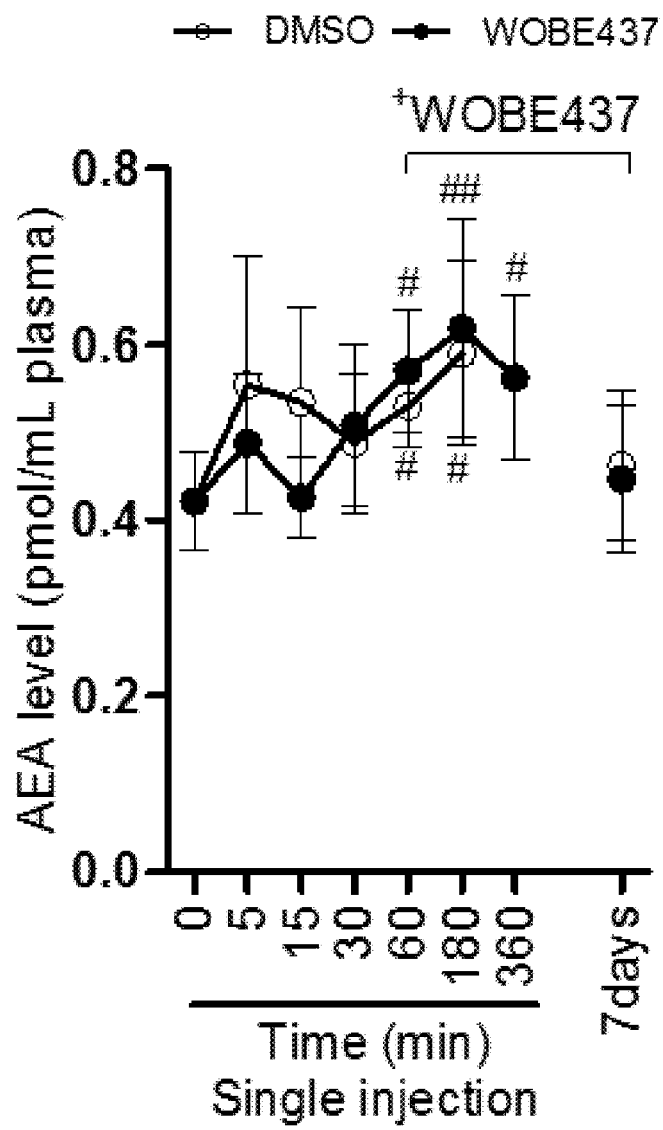
Figure 4C:
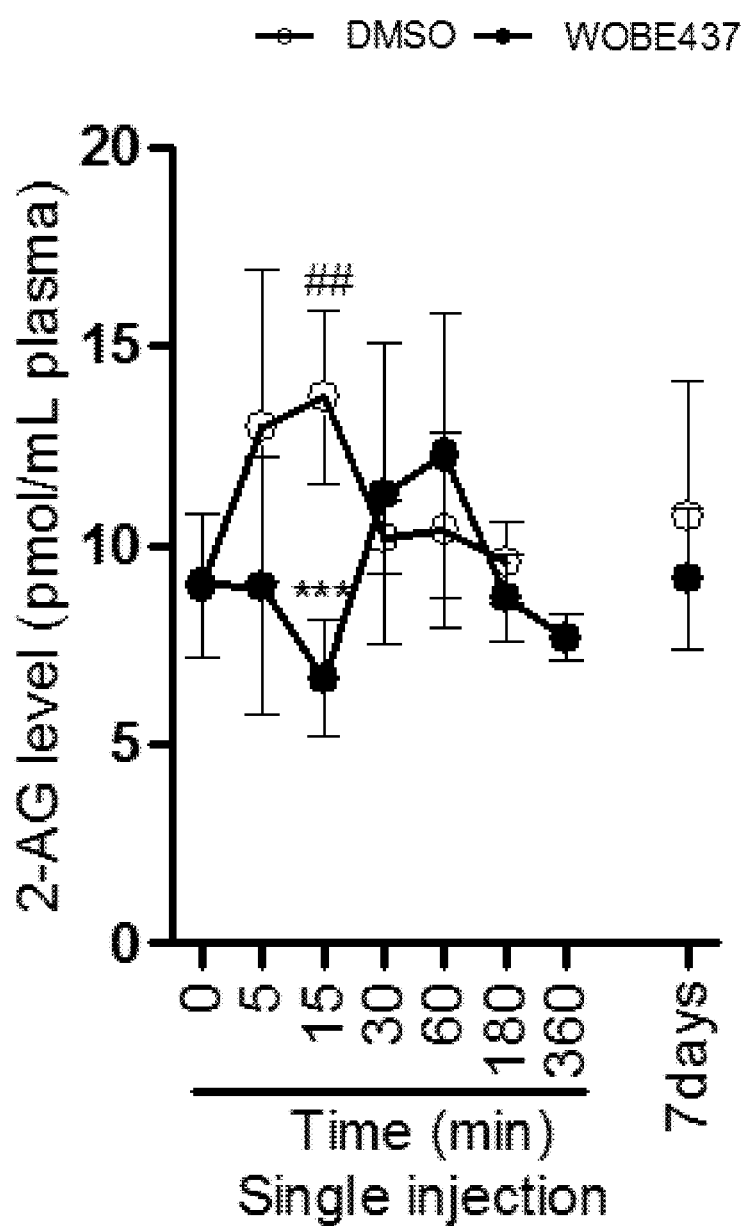

The compound of formula (I) is not only highly potent in inhibiting endocannabinoid cellular reuptake, it is furthermore highly selective for anandamide and 2-arachidonoyl glycerol even at substoichiometric concentrations relative to these types of endocannabinoids. In contrast, the levels of other NAEs in cell lines and human whole blood are not altered which shows that the compound of formula (I) is the first suitable selective endocannabinoid uptake inhibitor. Surprisingly, although WOBE437 can inhibit endocannabinoid release and reuptake, the net effect observed in complex matrices (i.e. whole blood and mice) showed an increase of endocannabinoid levels. Without wishing to be bound by theory, it seems plausible that a possible explanation of this effect may derive from a higher affinity of WOBE437 for reuptake inhibition which can also be linked to its limited cell penetration. Additionally, WOBE437 membrane target may be differentially involved in endocannabinoid reuptake and release as compared to other mechanisms. Indeed, residual anandamide and 2-arachidonoyl glycerol reuptake upon WOBE437 treatment is approximately 20-30% while it can inhibit only 20% of endocannabinoid release (i.e., 80% residual release). In tissues, binding kinetics indicate that WOBE437 binds to a membrane site with high affinity (10-20 nM). However, a second low affinity binding site and/or nonspecific binding to phospholipids cannot be excluded. WOBE437 is hydrolytically stable and after i.p. administration at 10 mg/kg rapidly and efficiently accumulates in the brain ($K_p>1$ after 15 min). In order to assess the potential role of endocannabinoid uptake in vivo, the pharmacological and biochemical effects of WOBE437 have been thoroughly investigated. In mice, 10 mg/kg of WOBE437 elicited a full tetrad response, which is a hallmark of either direct $CB_1$ receptor activation or the simultaneous elevation of anandamide and 2-arachidonoyl glycerol levels in the brain (FIG. 3a-d). In contrast, it is known that FAAH inhibitors only trigger analgesia, while MAGL inhibitors induce hypolocomotion, hypothermia and analgesia, but not catalepsy. The LC-MS/MS data show that in total brain tissue, acute WOBE437 treatment significantly increases 2-arachidonoyl glycerol levels without affecting anandamide (FIGS. 4F and 4G).

However, the $CB_1$-mediated WOBE437-induced behavioral changes indicate that the significant increase in 2-arachidonoyl glycerol is likely accompanied by a mild and/or region-specific rise of anandamide levels. At 5-10 mg/kg (e.g., a dose of about 5, 6, 7, 8, 9, or 10 mg/kg), WOBE437 elicites significant analgesic and anti-inflammatory effects in different animal models; at the sub tetrad-inducing dose of 3 mg/kg, the inhibitor exhibited anxiolytic effects in two mouse models of anxiety behavior (FIGS. 3i and 3j), similar to FAAH and MAGL inhibitors.

Surprisingly, after 7 days of treatment, both anandamide and 2-arachidonoyl glycerol levels significantly increase in the brain by a factor of 1.5 compared to vehicle. Similarly, WOBE437 accumulates in the brain, reaching a concentration of 926 nM after 7 days of treatment (10 mg/kg i.p., daily) compared to 555 nM 1 h after a single injection (FIGS. 4a and 4e). The levels of other NAEs remain essentially unchanged, suggesting that FAAH activity is not affected, which is also in agreement with the minor cell penetration of WOBE437 (FIG. 2a-d). The moderate increase of anandamide and 2-arachidonoyl glycerol concentrations induced by WOBE437 has been shown to not alter the number of functional $CB_1$ receptors in the brain.

In contrast, the prolonged 2-arachidonoyl glycerol "overflow" (10-12 times basal levels) resulting from repeated administrations of JZL184 has been shown to desensitize $CB_1$ receptors. The experimental data presented herein shows that a selective competitive endocannabinoid reuptake inhibitor modulates the homeostasis of anandamide and 2-arachidonoyl glycerol levels in a time- and space-restricted manner without leading to an endocannabinoid overflow or altering the levels of other lipids. This unique pharmacological properties allows enhancing the endocannabinoid system activity by mildly and site-specifically increasing the levels of both major endocannabinoids AEA and 2-AG. WOBE437 is a competitive and reversible inhibitor of cellular endocannabinoid reuptake and this property intrinsically limits the possibility of an excessive accumulation of AEA and 2-AG. Our data also indicate that by modulating the levels of both AEA and 2-AG, WOBE437 triggers the full spectrum of endocannabinoid activities unlike FAAH and MAGL inhibitors which only increase the levels of AEA or 2-AG. Finally, in vitro, ex vivo and in vivo WOBE437 inhibited the cellular reuptake of AEA and 2AG without affecting the levels of other related lipids (e.g. N-acetylethanolamines) in contrast with FAAH and MAGL inhibitors. This selectivity may significantly reduce the possibility of off-target-mediated side effects.

Importantly, after repeated administrations WOBE437 (10 mg/kg) did not significantly alter the levels of anandamide, 2-arachidonoyl glycerol and NAEs in kidney and liver. This represents another pharmacological difference between the inhibition of endocannabinoid reuptake and the blockage of endocannabinoid degradation. The possibility to tissue-specifically increase endocannabinoid levels provides a new targeted-approach without leading to chronic activation of liver and kidney $CB_1$ receptors that exacerbate inflammation, promoting liver and renal fibrosis, insulin resistance, steatosis and nephropathy.

Figure 4D:
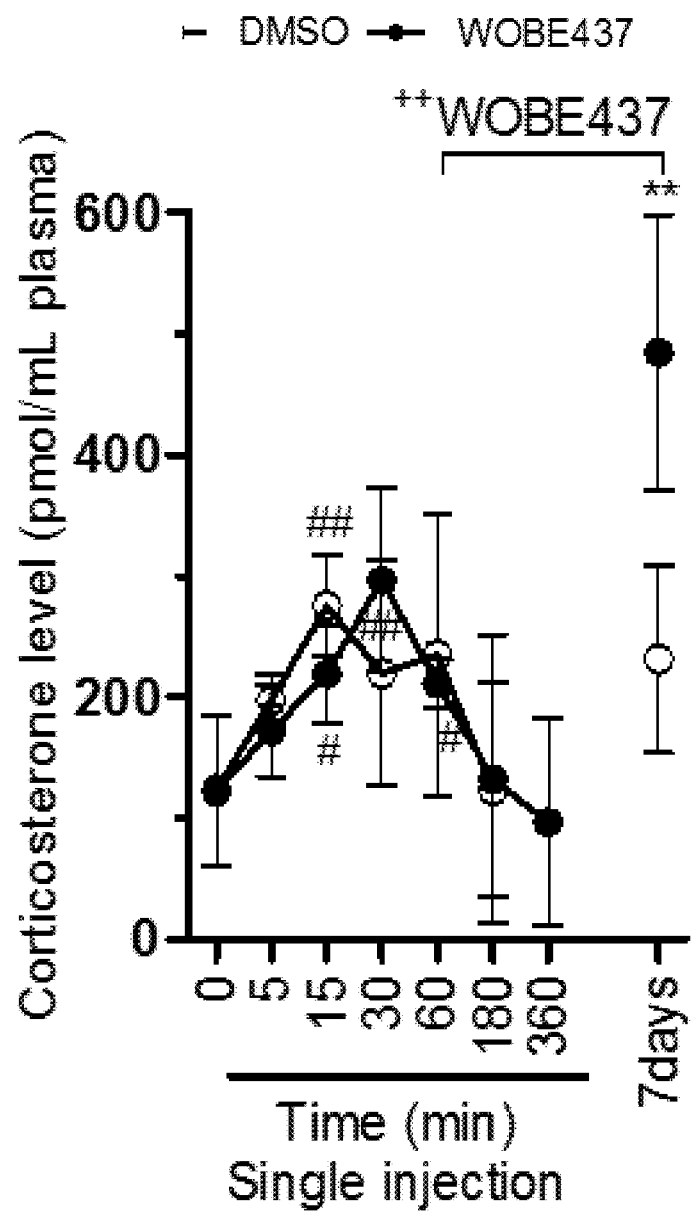
Figure 4E:
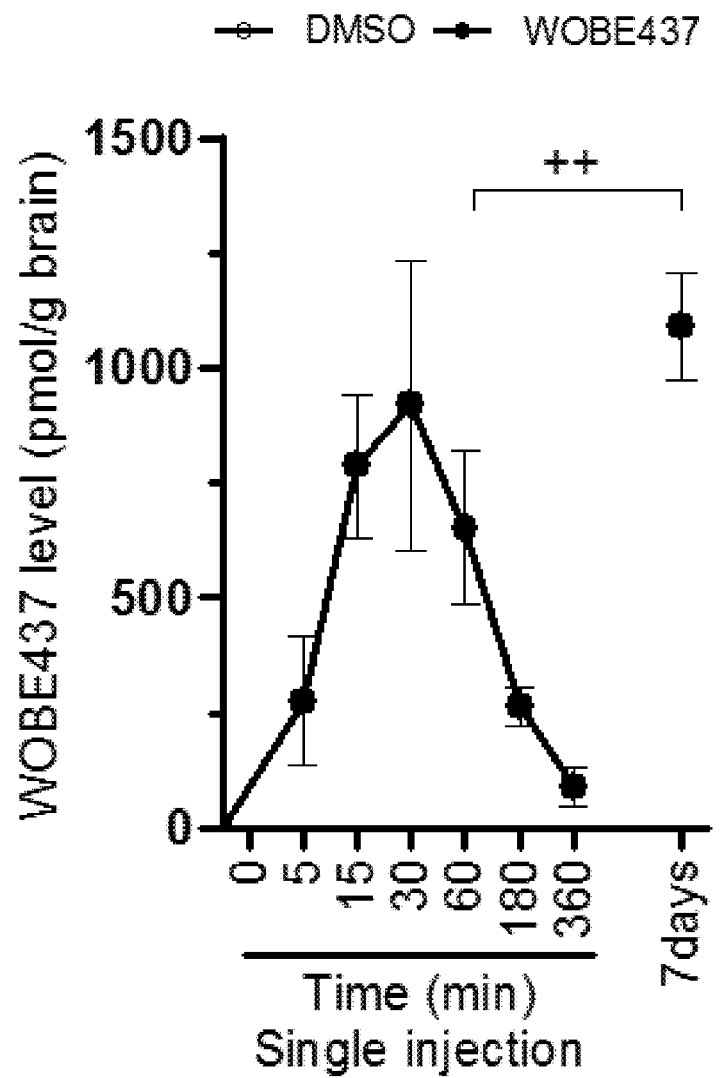
Figure 4F:
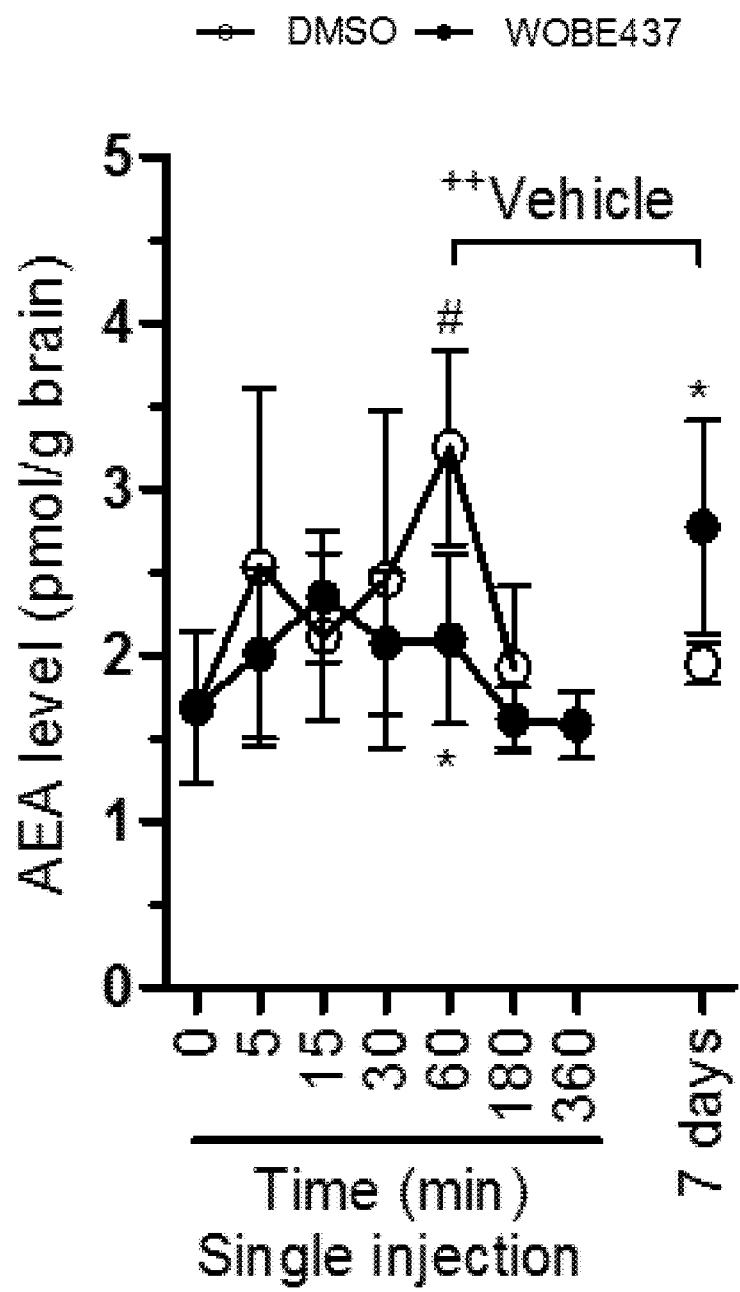
Figure 4G:
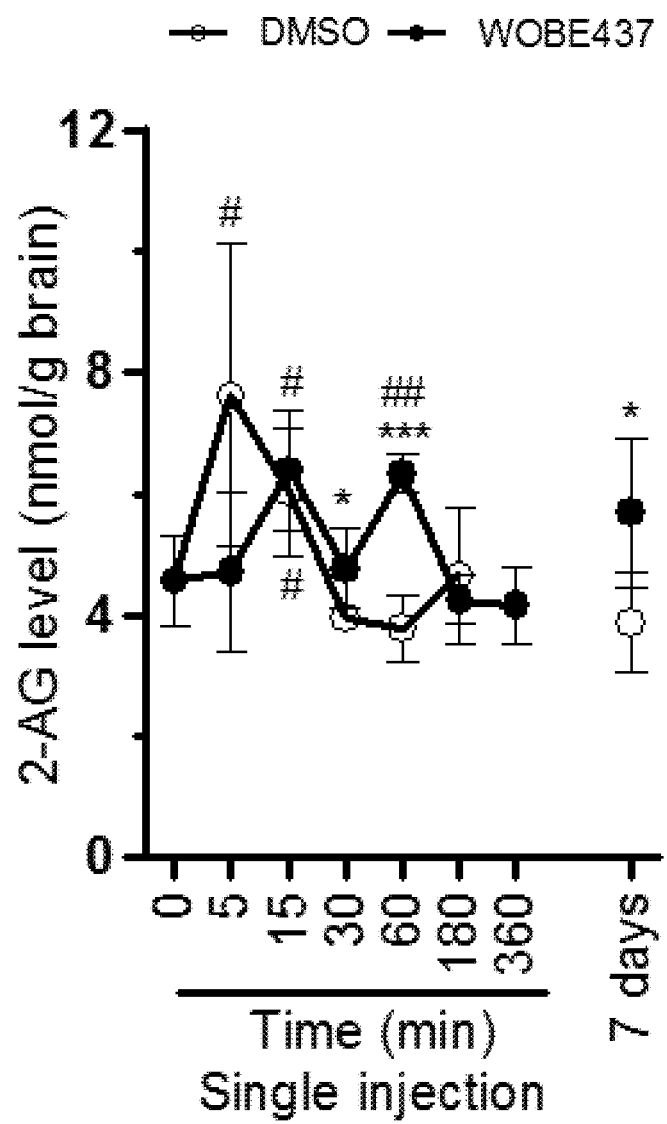
Figure 4H:
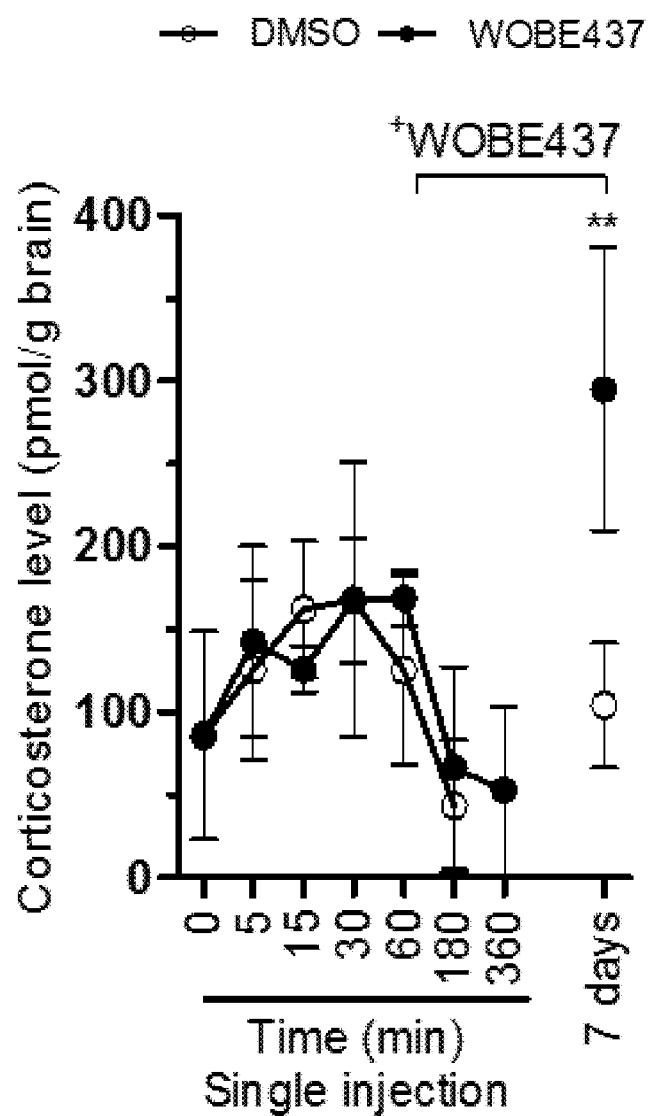

It has furthermore been found that repeated administration of WOBE437 leads to a significant 2-4 fold increase of the corticosterone levels in brain, plasma and peripheral organs (FIGS. 4D and 4H). A potential correlation between $\Delta^9$-THC-induced suppression of neuroinflammation and activation of the hypothalamic-pituitary-adrenal (HPA) axis in multiple sclerosis has recently been discussed. Although stress conditions are usually characterized by high cortisol levels, burnout patients and people suffering from post-traumatic stress disorders and certain types of depressive disorders have an impaired response of the HPA axis which leads to hypocortisolism. In these patients, the chronic low level of cortisol has been correlated with the severity of clinical and non-clinical symptoms.

Figure 3A:
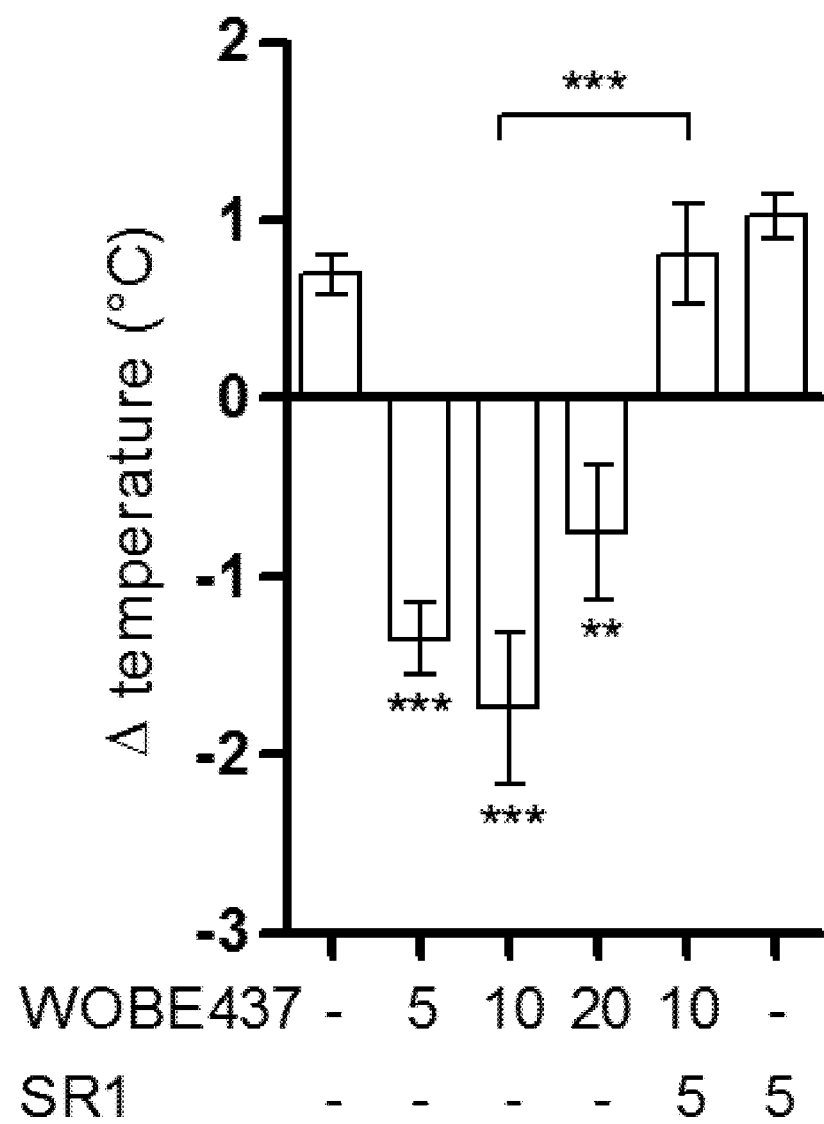
FIGS. 3A-3J. Pharmacological profile of WOBE437 in vivo.
Figure 3B:
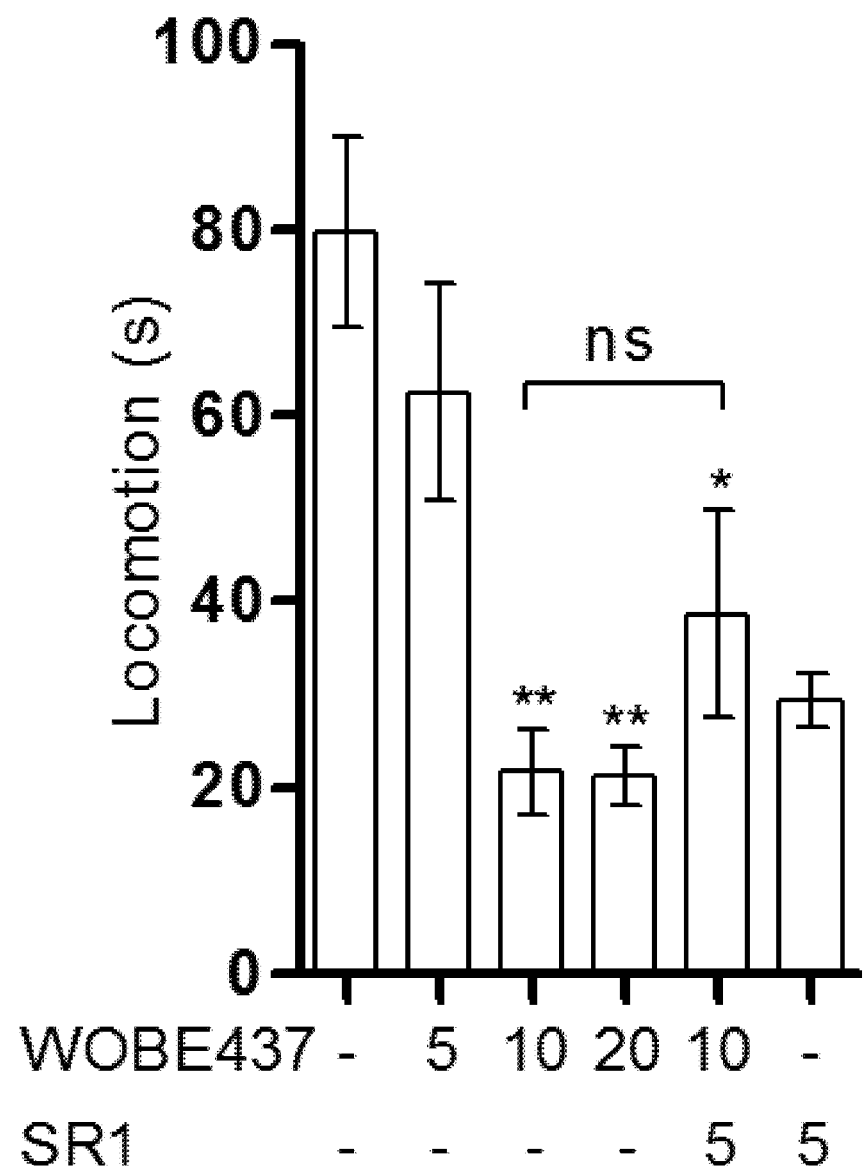
Figure 3C:
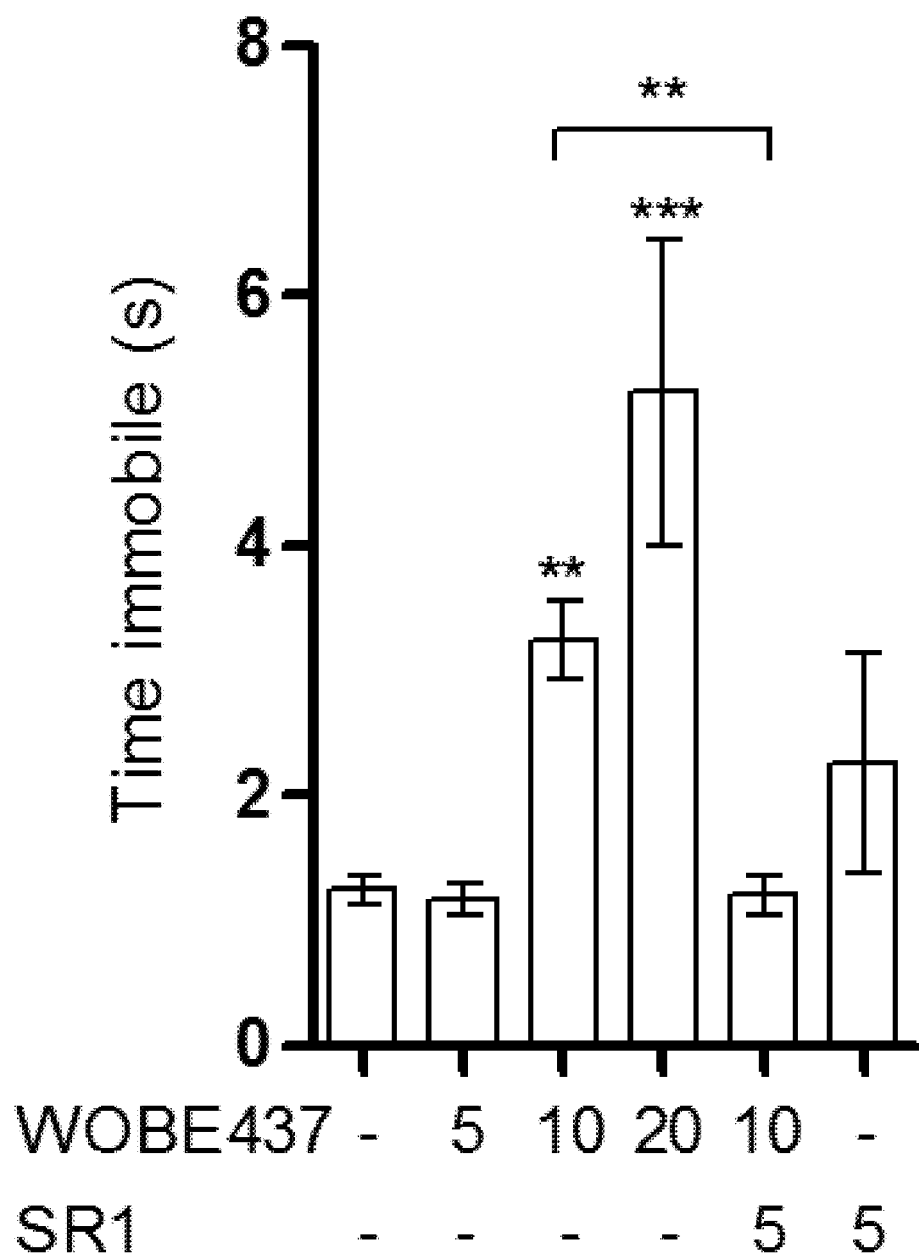
Figure 3D:
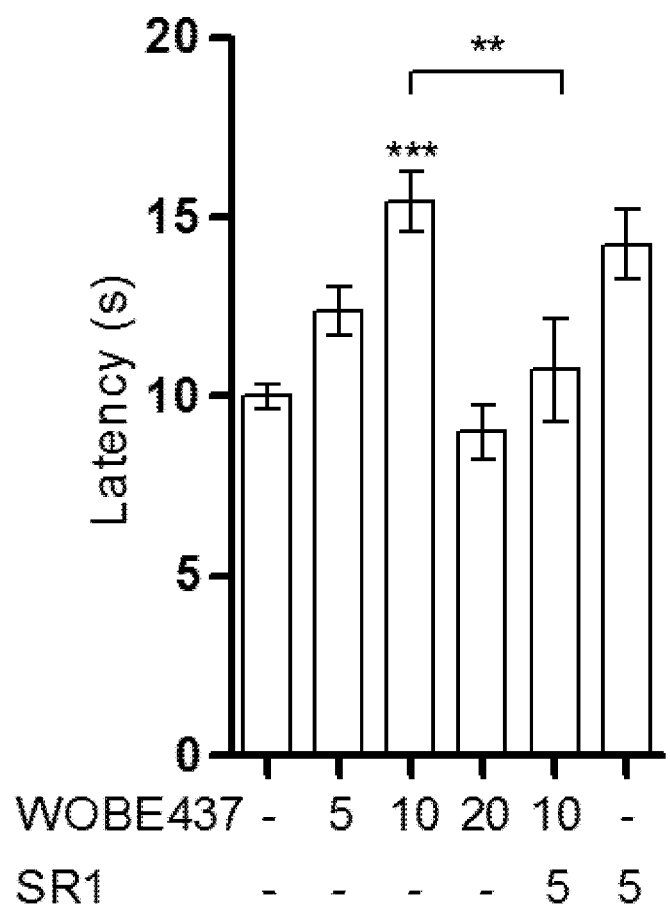
Figure 3E:
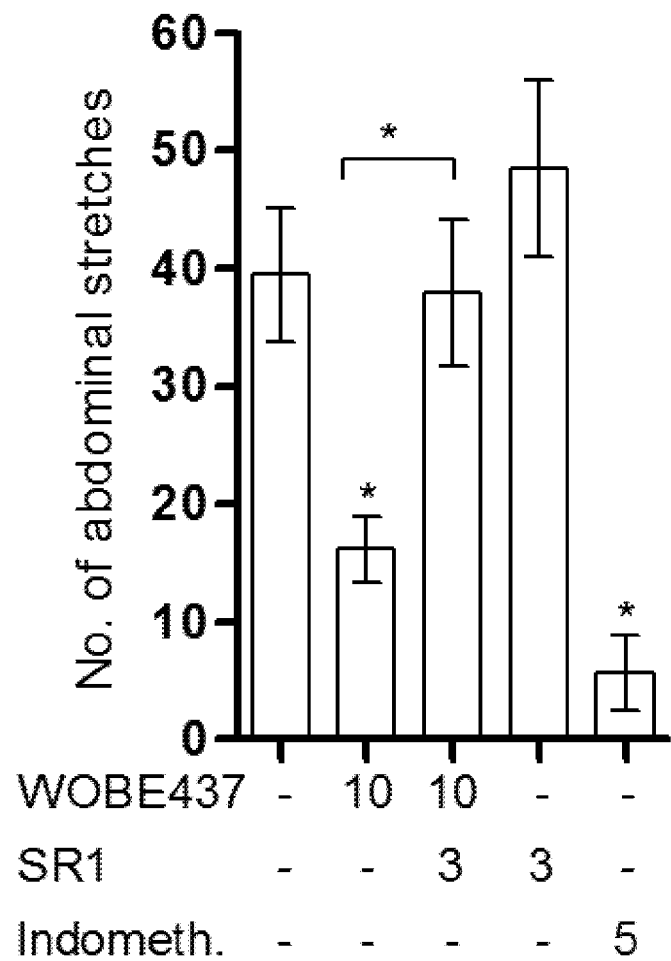
Figure 3F:
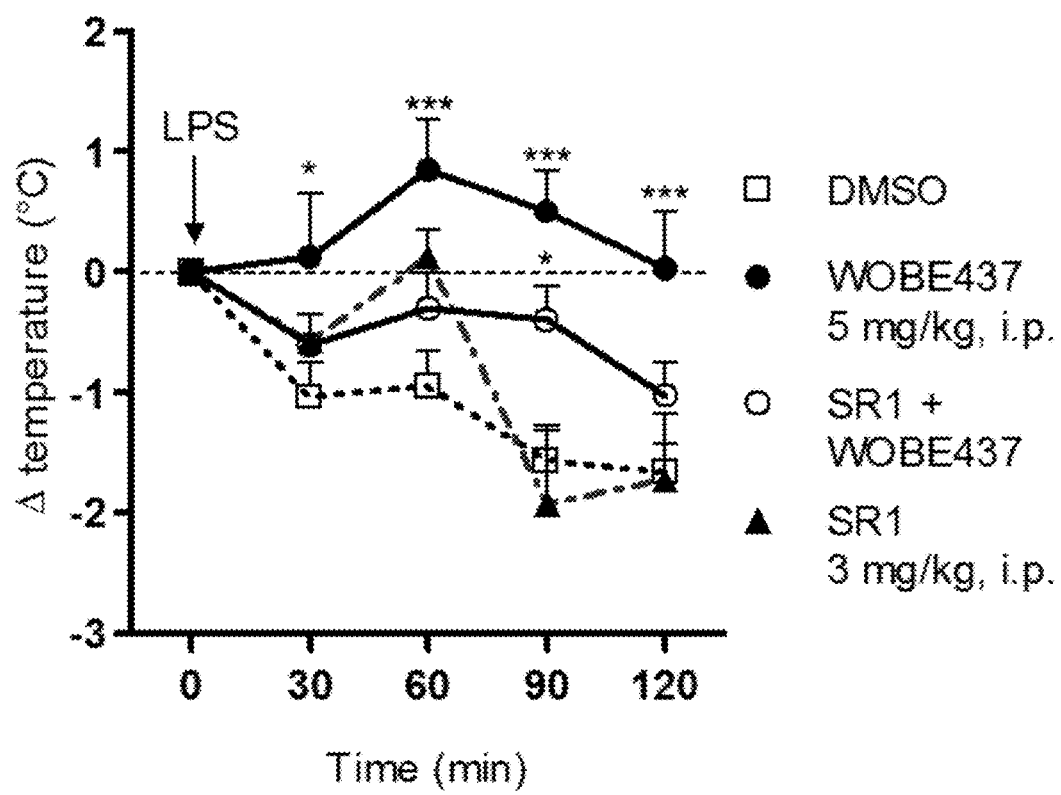
Figure 3G:
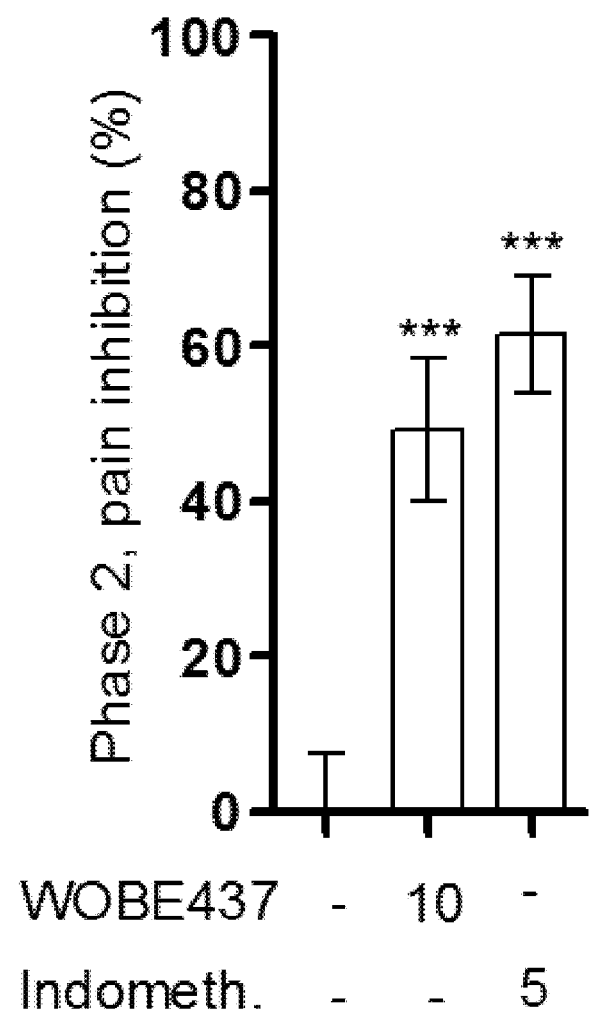
Figure 3H:
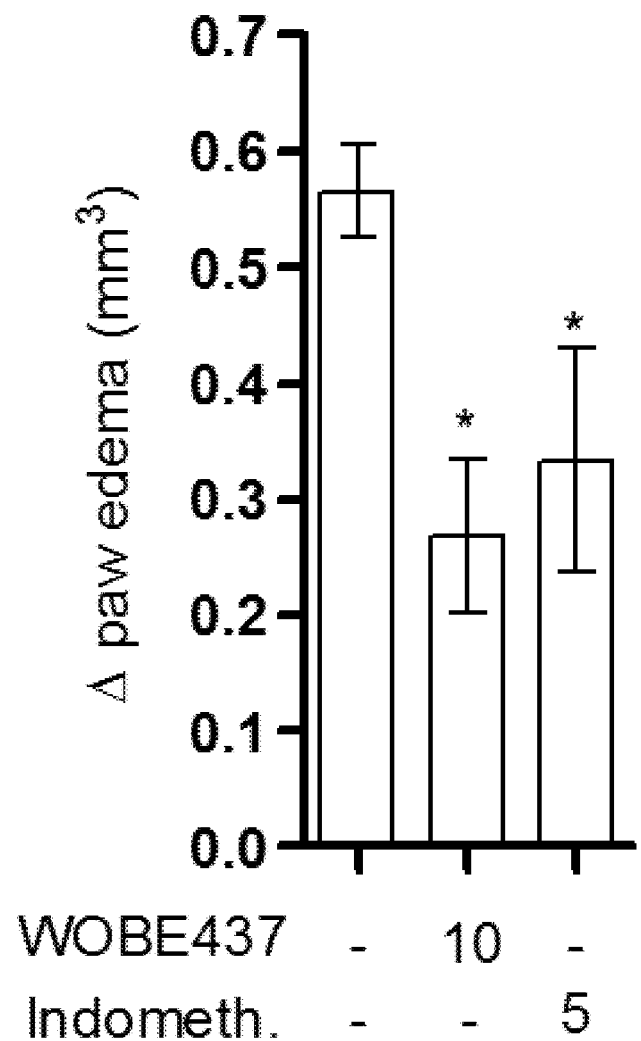
Figure 3I:
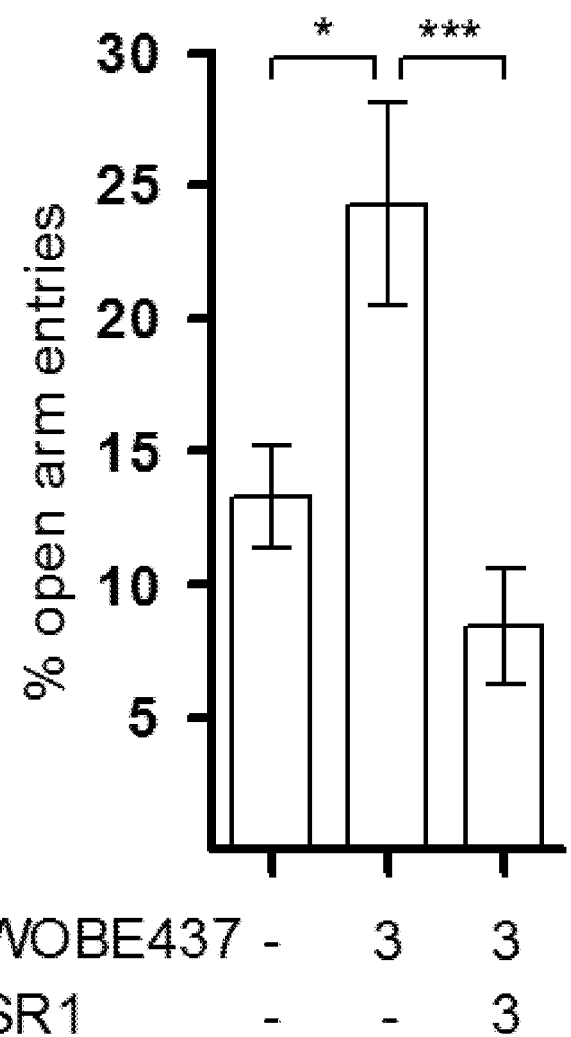
Figure 3J:
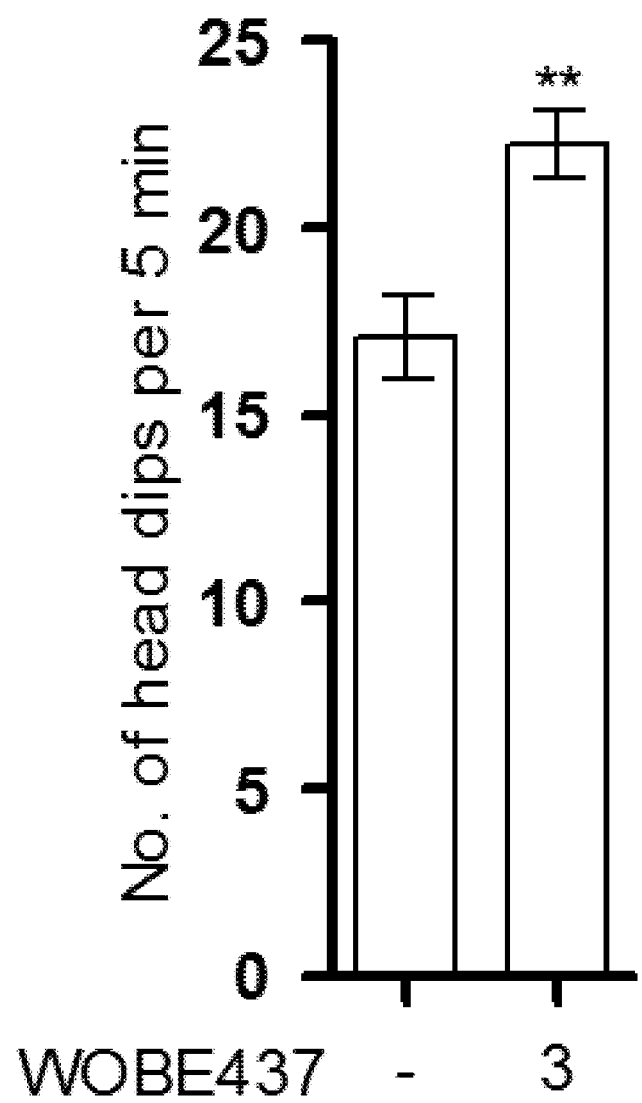

The pharmacological effects of the compound of formula (I) have also been investigated in vivo. Accordingly, WOBE437 has been assessed in a battery of four individual tests typically associated with $CB_1$ receptor activation in mice (nociception, locomotion, body temperature and cataleptic behavior), collectively referred to as the "tetrad". Dose-response experiments identified 10 mg/kg as the lowest dose to elicit a moderate but complete tetrad in BALB/c mice upon intraperitoneal (i.p.) administration (FIGS. 3A-D). These experiments provide a proof-of-concept for the mechanism of action of WOBE437 as a novel "indirect $CB_1$ receptor agonist". In subsequent studies, the effects of WOBE437 in pain, inflammatory and anxiety models have been evaluated. At doses of 5 and 10 mg/kg, WOBE437 elicits significant analgesic and anti-inflammatory effects, as indicated by the reduced number of abdominal stretches in the acetic writhing test, comparable to indomethacin (5 mg/kg), and by protective effects in lipopolysaccharides (LPS)-induced endotoxemia in BALB/c mice. At the lower dose of 3 mg/kg, WOBE437 shows significant anxiolytic effects in C57BL6/N mice in the elevated plus maze (EPM) and in the holeboard (HB) test (FIGS. 3I-J). The anxiolytic effect was completely blocked by SR1, indicating an indirect $CB_1$ receptor-mediated mechanism for WOBE437. The anxiolytic effect of WOBE437 has been confirmed in a HB test, in which the head dipping frequency was significantly increased after 1 h post injection (FIG. 3J).

The present inventors also found that WOBE437 selectively modulates 2-arachidonoyl glycerol and anandamide concentrations in mice. In order to investigate whether there was a link between the in vivo pharmacological effects of WOBE437 and the inhibition of endocannabinoid uptake in vitro, the levels of WOBE437, anandamide, 2-arachidonoyl glycerol and related lipids in different tissues have been quantified by LC-MS/MS. Accordingly, in the brain, anandamide levels do not change compared to basal level after a single injection with WOBE437 (FIG. 4F). On the contrary, 2-arachidonoyl glycerol levels increase 1.7-fold compared to vehicle at 1 h post-injection (FIG. 4G). After 7 days of daily treatment, both anandamide and 2-arachidonoyl glycerol levels are significantly raised by 1.5-fold compared to DMSO. The moderate but significant increase of both endocannabinoids in the brain apparently does not affect the number of functional $CB_1$ receptors. Repeated administrations of WOBE437 have been shown to lead to a significant 3-fold increase of corticosterone in the brain, which mirrors the changes observed in plasma (FIG. 4H). Endocannabinoid concentrations are not affected by repeated administrations of WOBE437 in peripheral tissues. Furthermore, the concentrations of other lipids (NAEs, AA, prostaglandins and progesterone) are not significantly altered upon WOBE437 treatment in brain, plasma and peripheral organs.

Based on WOBE437, the irreversible endocannabinoid transport inhibitor RX-055 has been developed which provides further evidence of the selective anti-inflammatory and anxiolytic effects. The preparation of RX-055 and the evaluation have been described by the present inventors in detail in Proc. Natl. Acad. Sci. USA. 2017, 114(25), pages E5006-E5015.

In view of the above discussion, which is supported by the experimental data presented in the Examples below and by the data presented by the present inventors in Proc. Natl. Acad. Sci. USA. 2017, 114(25), pages E5006-E5015 and the Supplementary Information published therewith, the excellent potency and selectivity of WOBE437 for cellular reuptake of specific endocannabinoids is clearly evidenced.

Thus the present invention also relates to a formulation, comprising the compound of formula (I) or the solvate or co-crystal thereof and a pharmaceutically acceptable excipient.

The term "pharmaceutically acceptable" indicates that the compound or formulation, typically and preferably the solvates, co-crystals or carrier, must be compatible chemically or toxicologically with the other ingredient(s), typically and preferably with the inventive formulation, when typically and preferably used in a formulation or when typically and preferably used for treating the animal, preferably the human, therewith. Preferably, the term "pharmaceutically acceptable" indicates that the compound or formulation, typically and preferably the solvates, co-crystals or carrier, must be compatible chemically and toxicologically with the other ingredient(s), typically and preferably with the inventive formulation, when typically and preferably used in a formulation or when typically and preferably used for treating the animal, preferably the human, therewith. It is noted that pharmaceutical compositions and formulations can be formulated by techniques known to the person skilled in the art, such as the techniques published in "Remington: The Science and Practice of Pharmacy", Pharmaceutical Press, 22nd edition.

The compound of formula (I) can be used to treat a wide variety of diseases, disorders and conditions. Examples include diseases and conditions where a patient is in need of selective inhibition of EC reuptake, for example in chronic inflammatory conditions in which different receptors and signaling pathways cooperate in the etiopathology. Examples thereof include asthma, pain, such as neuropathic pain, peripheral pain; persistent pain, and inflammatory pain; epilepsy, hyperactivity, cardiovascular diseases and blood pressure disorders, such as hypertension, brain ischemia, spasticity, diseases associated with motor function, such as Tourette's syndrome; schizophrenia, hemorrhagic shock, septic shock, cardiac shock, migraine, Horton's headache, anorexia, AIDS wasting syndrome, organ rejection, autoimmune diseases, allergy, arthritis, Crohn's disease, malignant gliomas, neurodegenerative diseases, including multiple sclerosis, Parkinson's disease, Huntington's chorea and Alzheimer's disease; nausea, such as nausea associated with cancer chemotherapy; anxiety, psychosis, attention deficit hyperactivity disorder, premature ejaculation, and stroke. Further indications include the treatment of substance of abuse disorders, in particular alcohol use disorder (AUD), tobacco use disorder (TUD), *Cannabis* use disorder (CAB), opioid use disorder, stimulant use disorder and hallucinogen use disorder. Still further indications include the treatment of a liver disease, such as alcohol-related liver disease, non-alcoholic fatty liver disease, hepatic ischaemia-reperfusion injury, liver fibrosis, hepatitis, primary biliary cirrhosis, primary sclerosing cholangitis; or a kidney disease, such as chronic kidney disease, diabetic kidney disease and kidney ischaemia-reperfusion injury. The compounds of the present invention may further be used in the treatment of skin diseases such as psoriasis, atopic dermatitis, systemic scleroderma, severe itching or pruritus associated with different causes. The compounds of the present invention may further be used in the treatment of eye diseases such as uveitis, conjunctivitis, scleritis, keratitis and other inflammatory and immunological disorders of different origins; glaucoma of different origins; retinopathies of different origins. Furthermore, the compound of formula (I) can also be used to provide neuro-protection, to produce peripheral vasodilation, to suppress memory, to enhance appetite and to reduce fertility.

In preferred embodiments, the mammal is a primate, equine, canine or feline. In more preferred embodiments, the mammal is a human.

The term "therapeutically effective amount" here refers to that amount sufficient to modulate one or more of the symptoms of the condition or disease being treated, preferably between 10 mg and 3000 mg per administration (e.g., about 10, 15, 20, 25, 30, 35, 40, 45, 50, 55, 60, 65, 70, 75, 80, 85, 90, 95, 100, 110, 120, 125, 130, 140, 150, 160, 170, 175, 180, 190, 200, 210, 220, 225, 230, 240, 250, 260, 270 275, 280, 290, 300, 310, 320, 325, 330, 340, 350, 360, 370, 375, 380, 390, 400, 425, 450, 475, 500, 525, 550, 575, 600, 625, 650, 675, 700, 725, 750, 775, 800, 825, 850, 875, 900, 925, 950, 975, 1000, 1100, 1200, 1300, 1400, 1500, 1600, 1700, 1800, 1900, 2000, 2100, 2200, 2300, 2400, 2500, 2600, 2700, 2800, 2900, or 3000), given once daily or twice daily or three times daily, e.g. intravenously or by the oral route.

If the compound of the present invention or the formulation comprising it is administered parenterally, then examples of such administration include one or more of: intravenously, intraarterially, intraperitoneally, intrathecally, intraventricularly, intraurethrally, intrasternally, intracardially, intracranially, intramuscularly or subcutaneously administering the compound or formulation, and/or by using infusion techniques. For parenteral administration, the compound of the present invention (or the formulation comprising it) is preferably used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well known to those skilled in the art.

Said compound of the present invention or the formulation comprising it can also be administered orally in the form of tablets, capsules, ovules, elixirs, solutions or suspensions, which may contain flavoring or coloring agents, for immediate-, delayed-, modified-, sustained-, pulsed- or controlled-release applications.

The tablets may contain excipients such as microcrystalline cellulose, lactose, sodium citrate, calcium carbonate, dibasic calcium phosphate and glycine, disintegrants such as starch (preferably corn, potato or tapioca starch), sodium starch glycolate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia. Additionally, lubricating agents such as magnesium stearate, stearic acid, glyceryl behenate and talc may be included. Solid compositions of a similar type may also be employed as fillers in gelatin capsules. Preferred excipients in this regard include lactose, starch, a cellulose, or high molecular weight polyethylene glycols. For aqueous suspensions and/or elixirs, the agent may be combined with various sweetening or flavoring agents, coloring matter or dyes, with emulsifying and/or suspending agents and with diluents such as water, ethanol, propylene glycol and glycerin, and combinations thereof.

Alternatively, said compound of the present invention or the formulation comprising it can be administered in the form of a suppository or pessary, or it may be applied topically in the form of a gel, hydrogel, lotion, solution, cream, ointment or dusting powder. The compound of the present invention or the formulation comprising it may also be dermally or transdermally administered, for example, by the use of a skin patch.

The compound of the present invention can be administered also topically in the eye in the form of solutions, suspensions, ointments or direct injection into the eye. The compound of the present invention can be formulated in different forms including excipients, preservatives, surface-active agents, viscosity-modifying agents, antioxidants stabilizers and liposomes.

Said compound of the present invention or the formulation comprising it may also be administered by sustained release systems. Suitable examples of sustained-release compositions include semi permeable polymer matrices in the form of shaped articles, e.g., films, or microcapsules. Sustained-release matrices include, e.g., polylactides (see, e.g., U.S. Pat. No. 3,773,919), copolymers of L-glutamic acid and gamma-ethyl-L-glutamate (Sidman, U. et al., Biopolymers 22:547-556 (1983)), poly(2-hydroxyethyl methacrylate) (R. Langer et al., J. Biomed. Mater. Res. 15:167-277 (1981), and R. Langer, Chem. Tech. 12:98-105 (1982)), ethylene vinyl acetate (R. Langer et al., Id.) or poly-D-(−)-3-hydroxybutyric acid (EP133988). Sustained-release pharmaceutical compositions also include liposomally entrapped compounds. Liposomes containing a compound of the present invention can be prepared by methods known in the art, such as, e.g., the methods described in any one of: DE 3218 121; Epstein et al., Proc. Natl. Acad. Sci. (USA) 82:3688-3692 (1985); Hwang et al., Proc. Natl. Acad. Sci. (USA) 77:4030-4034 (1980); EP 0 052 322; EP 0 036 676; EP 088 046; EP 0 143 949; EP 0 142 641; JP 83-118008; U.S. Pat. Nos. 4,485,045; 4,544,545; and EP 0 102 324.

Said compound of the present invention or the formulation comprising it may also be administered by the pulmonary route, rectal routes, or the ocular route. For ophthalmic use, they can be formulated as micronized suspensions in isotonic, pH adjusted, sterile saline, or, preferably, as solutions in isotonic, pH adjusted, sterile saline, optionally in combination with a preservative such as a benzalkonium chloride. Alternatively, they may be formulated in an ointment such as petrolatum.

It is also envisaged to prepare dry powder formulations of the compound of the present invention or the formulation comprising it for pulmonary administration, particularly inhalation. Such dry powders may be prepared by spray drying under conditions which result in a substantially amorphous glassy or a substantially crystalline bioactive powder. Accordingly, dry powders of the compounds of the present invention can be made according to the emulsification/spray drying process disclosed in WO 99/16419 or WO 01/85136. Spray drying of solution formulations of the compounds of the present invention can be carried out, e.g., as described generally in the "Spray Drying Handbook", 5th ed., K. Masters, John Wiley & Sons, Inc., NY (1991), and in WO 97/41833 or WO 03/053411.

For topical application to the skin, said compound of the present invention or the formulation comprising it can be formulated as a suitable ointment containing the active compound suspended or dissolved in, for example, a mixture with one or more of the following: mineral oil, liquid petrolatum, white petrolatum, propylene glycol, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, 2-octyldodecanol, benzyl alcohol and water.

The compound of the present invention can be administered also topically in the eye in the form of solutions, suspensions, ointments or direct injection into the eye. The compound of the present invention can be formulated in different forms including, for example, one or more of excipients, preservatives, surface-active agents, viscosity-modifying agents, antioxidants stabilizers and liposomes.

The present invention thus relates to the compound of the present invention or the formulation comprising it as provided herein, wherein the corresponding compound or formulation is to be administered by any one of: an oral route; topical route, including by transdermal, intranasal, ocular, buccal, or sublingual route; parenteral route using injection techniques or infusion techniques, including by subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, intrasternal, intraventricular, intraurethral, or intracranial route; pulmonary route, including by inhalation or insufflation therapy; gastrointestinal route; intrauterine route; intraocular route; subcutaneous route; ophthalmic route, including by intravitreal, or intracameral route; rectal route; or vaginal route. Particularly preferred routes of administration of the compound or formulation of the present invention for systemic uses are oral administration or parenteral administration (e.g., subcutaneous or intravenous administration), and most preferably, the compound or formulation of the invention is to be administered orally. Alternatively, the compound is administered by means of a transdermal patch. For topical applications, the compounds is administered locally on the skin as a cream or an ointment and as eye drops or direct injection into the eye to treat glaucoma and other eye diseases.

Typically, a physician will determine the actual dosage which will be most suitable for an individual subject. The specific dose level and frequency of dosage for any particular individual subject may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the individual subject undergoing therapy.

A proposed, yet non-limiting dose of the compounds according to the invention for oral administration to a human (e.g., of approximately 70 kg body weight) may be 0.05 to 2000 mg, preferably 0.1 mg to 1000 mg, of the active ingredient per unit dose (e.g., about 0.05, 0.06, 0.07, 0.08, 0.09, 0.10, 0.11, 0.12, 0.13, 0.14, 0.15, 0.16, 0.17, 0.18, 0.19, 0.20, 0.25, 0.30, 0.35, 0.40, 0.45, 0.5, 0.6, 0.7, 0.8, 0.9, 1.0, 1.1, 1.2, 1.3, 1.4, 1.5, 1.75, 2.0, 2.25, 2.5, 2.75, 3.0, 3.25, 3.5, 3.75, 4.0, 4.25, 4.5, 4.75, 5.0, 5.5, 6.0, 6.5, 7.0, 7.5, 8.0, 8.5, 9.0, 9.5, 10.0, 11, 12, 13, 14, 15, 16, 17, 18, 19, 20, 21, 22, 23, 24, 25, 28, 30, 33, 35, 38, 40, 43, 45, 48, 50, 55, 60, 65, 70, 75, 80, 85, 90, 95, 100, 125, 150, 175, 200, 225, 250, 275, 300, 350, 400, 450, 500, 550, 600, 650, 700, 750, 800, 900, 1000, 1100, 1200, 1300, 1400, 1500, 1600, 1700, 1800, 1900, 2000, or ranges thereof). The unit dose may be administered, e.g., 1 to 3 times per day. The unit dose may also be administered 1 to 7 times per week, e.g., with not more than one administration per day. It will be appreciated that it may be necessary to make routine variations to the dosage depending on the age and weight of the patient/subject as well as the severity of the condition to be treated. The precise dose and also the route of administration will ultimately be at the discretion of the attendant physician or veterinarian.

The compound of formula (I) can be used in combination with other therapeutic agents. For example, the formulation may comprise the compound of formula (I) as well as the other therapeutic agent(s). When the compound of the invention is used in combination with a second therapeutic agent active against the same disease, the dose of each compound may differ from that when the compound is used alone. The combination of a compound of the present invention with a second therapeutic agent may comprise the administration of the second therapeutic agent simultaneously/concomitantly or sequentially/separately with the compound of the invention.

Preferably, the second therapeutic agent to be administered in combination with a compound of this invention is anticancer drugs, non-steroidal anti-inflammatory drugs, corticosteroids, cyclopegics, beta-blockers, adrenergic drugs, prostaglandins, immunosuppressive agents, carbonic anhydrase inhibitors, prostaglandins, anxiolytic drugs, antidepressants.

In a further embodiment, the present invention relates to a method of treating a mammal suffering from a disease, illness or disorder associated with an aberrant functioning of the endocannabinoid system, in particular related to endocannabinoid deficiency, comprising administering to said mammal a therapeutically effective amount of a compound of Formula (1), or a pharmaceutically acceptable solvate or co-crystal thereof, wherein the endocannabinoid is preferably one or both selected from anandamide and 2-arachidonoyl glycerol.

In yet a further embodiment, the present invention relates to a method of modulating endocannabinoid reuptake in a mammal, comprising the step of:

administering to said mammal a therapeutically effective amount of a compound of Formula (1), or a pharmaceutically acceptable solvate or co-crystal thereof, wherein the endocannabinoid is preferably one or both selected from anandamide and 2-arachidonoyl glycerol.

In any embodiments of the present invention, the compound or formulation of the present invention is preferably administered orally. For topical applications, the compound may be administered locally on the skin as a cream or an ointment and as eye drops or direct injection into the eye to treat glaucoma and other eye diseases.

CITED REFERENCES

1. Maccarrone M, Guzman M, Mackie K, Doherty P, Harkany T (2014) Programming of neural cells by (endo)cannabinoids: from physiological rules to emerging therapies. Nat Rev Neurosci 15(12):786-801.
2. Piomelli D, Sasso O (2014) Peripheral gating of pain signals by endogenous lipid mediators. Nat Neurosci 17(2):164-174
3. Mechoulam R, Parker L A (2013) The endocannabinoid system and the brain. Annu Rev Psychol 64:21-47.
4. Lutz B, Marsicano G, Maldonado R, Hillard C J (2015) The endocannabinoid system in guarding against fear, anxiety and stress. Nat Rev Neurosci 16(12):705-718.
5. Batista L, Gobira P H, Viana T G, Aguiar D C, Moreira F (2014) Inhibition of endocannabinoid neuronal uptake and hydrolysis as strategies for developing anxiolytic drugs. Behav Pharmacol 25(5-6):425-33.
6. Chicca A, Marazzi J, Nicolussi S, Gertsch J (2012) Evidence for bidirectional endocannabinoid transport across cell membranes. J Biol Chem 287(41):34660-34682.
7. Beltramo M, et al. (1997) Functional role of high-affinity anandamide transport, as revealed by selective inhibition. Science 277(5329):1094-1097.
8. Hillard C J, Edgemond W S, Jarrahian A, Campbell W B (1997) Accumulation of N-arachidonoylethanolamine (anandamide) into cerebellar granule cells occurs via facilitated diffusion. J Neurochem 69(2):631-8.
9. Fegley D, et al. (2004) Anandamide transport is independent of fatty-acid amide hydrolase activity and is blocked by the hydrolysis-resistant inhibitor AM1172. Proc Natl Acad Sci USA 101 (23):8756-61.
10. Nicolussi S, Gertsch J (2015) Endocannabinoid Transport Revisited. Vitam Horm 98:441-85.

The present invention may be better understood with reference to the following examples. These examples are intended to be representative of specific embodiments of the invention, and are not intended as limiting the scope of the invention. All cited publications are hereby incorporated hi their entirety by reference, except that in case of conflict, the text of the specification as field controls.

EXAMPLES

Example A) Synthesis of WOBE437

General Synthetic Procedures.

Starting materials and reagents were purchased from commercial suppliers and used without further purification. All compounds were checked for homogeneity by TLC with silica gel as the stationary phase. NMR spectra were recorded on a Bruker DMX400 spectrometer ($^1$H at 400 MHz and $^{13}$C at 100 MHz). Alternatively, nuclear magnetic resonance ($^1$H and $^{13}$C NMR) spectra were recorded on a Bruker Avance 400 MHz spectrometer and were analyzed using the Topspin 1.3 software. Chemical shifts (δ) for $^1$H and $^{13}$C NMR are reported in parts per million (ppm) from an internal standard of solvent (CDCl$_3$ δ=7.26 and 77.0 ppm or DMSO-d$_6$ δ=2.50 and 39.51 ppm, respectively). Data are reported as shift, splitting (s=singlet, d=doublet, t=triplet, m=multiplet; b=broad), coupling constant in Hz; integration. HPLC-MS analyses were performed using an Agilent 1100 with ELSD (PL-ELS 2100) or an Agilent 1200 with diode array detector with UV-detection between 220 and 320 nm and Mass Selective Detector (MSD) in ESI+ and ESI-modus (mass range: m/z=100-800). The following methods were used: Gradient A: A Waters XBridge™ C18 column (3.5 µm, 2.1 mm×50 mm) was used. The flow rate was set to 0.8 mL/min applying a column temperature of 30° C. Acetonitrile containing 0.1% formic acid was used a mobile phase A and 0.1% aqueous formic acid was used as mobile phase B. Linear gradient from 2% to 98% acetonitrile in water (0.1% HCOOH) (0.0 min, 2% A; 3.5 min, 98% A; 6.0 min, 98% A), Gradient B: A Waters XBridge™ C18 column (3.5 µm, 2.1 mm×50 mm) was used. The flow rate was set to 0.8 mL/min applying a column temperature of 30° C. 95% acetonitrile+5% 10 mM ammonium bicarbonate in water was used a mobile phase A and 10 mM ammonium bicarbonate in water (pH=9.5) was used as mobile phase B. Linear gradient from 2% to 98% acetonitrile in water (0.1% HCOOH) (0.0 min, 2% A; 3.5 min, 98% A; 6.0 min, 98% A). Melting points (mp) were determined in open capillaries using a Büchi Melting Point B-540 or B-545 apparatus. High-resolution ESI positive mass spectra were obtained on a 4.7T Ultima FT-ICR-ESI Mass spectrometer (Varian, Inc., Palo Alto, Calif., USA) with ionization voltage of 3.0-3.8 kV.

Synthesis of (2E,4E)-N-[2-(3,4-Dimethoxyphenyl) ethyl]dodeca-2,4-dienamide (WOBE437)

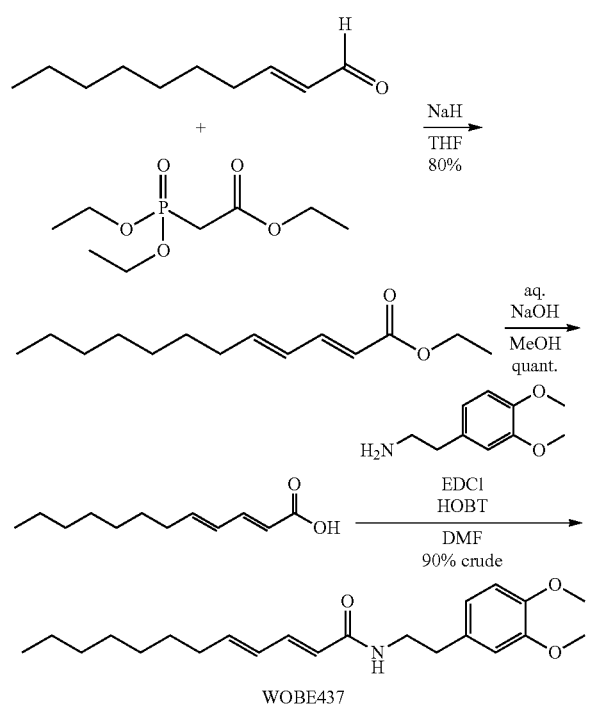

WOBE437

Purchased from Parchem and SigmaAldrich

Synthesis of (2E,4E)-N-[2-(3,4-Dimethoxyphenyl) ethyl]dodeca-2,4-dienamide (1; WOBE437)

(2E,4E)-Dodeca-2,4-dienoic acid (500 mg, 2.55 mmol) and 2-(3,4-dimethoxyphenyl)ethylamine (462 mg, 2.55 mmol) were mixed in dichloromethane (5 mL). EDC (537 mg, 2.80 mmol) and HOAt (173 mg, 1.274 mmol) were added and the reaction mixture was stirred at room temperature overnight. The reaction mixture was extracted with saturated sodium bicarbonate solution and the organic layer was separated and solvents were evaporated. Purification of the residue by flash column chromatography over silica (EtOAc/heptane from 5:95 to 50:50) afforded the title compound (1; WOBE437) as white solid (401 mg, 43%): M.p.: 112° C.; purity (LCMS, gradient A, $t_R$=3.70 min): >95%; $^1$H NMR (DMSO-d$_6$): δ 8.01 (t, J=5.5 Hz, 1H), 6.97 (dd, J=10.6, 15.1 Hz, 1H), 6.85 (d, J=8.2 Hz, 1H), 6.79 (d, J=1.9 Hz, 1H), 6.70 (dd, J=1.9, 8.2 Hz, 1H), 6.17 (dd, J=10.6, 15.1 Hz, 1H), 6.03-6.10 (m, 1H), 5.90 (d, J=15.0 Hz, 1H), 3.73 (s, 3H), 3.71 (s, 3H), 3.27-3.35 (m, 2H), 2.66 (dd, J=7.0, 7.5 Hz, 2H), 2.11 (q, J=7.0 Hz, 2H), 1.33-1.42 (m, 2H), 1.19-1.32 (m, 8H), 0.86 (t, J=6.8 Hz, 3H); $^{13}$C NMR (DMSO-d$_6$) δ 165.18, 148.55, 147.18, 141.66, 139.10, 131.91, 128.58, 123.28, 120.39, 112.44, 111.80, 55.47, 55.32, 40.42, 34.71, 32.25, 31.25, 28.59, 28.54, 28.39, 22.10, 13.97; ESI-MS(+) (m/z) calcd. for $C_{22}H_{33}NO_3$, 359.50 g/mol; found 360.2 [M+H]$^+$; HRMS (m/z): [M]$^+$ calcd. for $C_{22}H_{33}NO_3$, 360.2533; found, 360.2533.

Example B1) Biochemical Evaluation of WOBE437—Discovery of WOBE437 as a Highly Potent AEA Uptake Inhibitor Based on the natural product (2E,4E)-N-isobutylamidedodeca-2,4-dienamide from the medicinal plant E. purpurea as a starting point, a library of 634 of analogs and derivatives with varying alkyl chain length was synthesized, and structure of the head group moiety analyzed. All new derivatives were tested for AEA uptake inhibition in U937 cells using a high-content screening assay. From a total of 348 analogs, the dodeca-2E,4E-dienoyl N-alkylamide scaffold was identified as the most promising framework for the development of EC transport inhibitors highly selective against FAAH (>100 fold selectivity, FIG. 1A). For instance, N-(pyridin-3-yl)ethyl, N-(2-methoxyphenyl)ethyl, and N-(2,3-dihydro-1,4-benzodioxin-6-yl)ethyl dodeca-2E,4E-dienamide, respectively, exhibited IC$_{50}$ values in the nanomolar range for AEA uptake and 60- to 110-fold selectivity over AEA hydrolysis (FIGS. 1A-B). The ethyl linker connecting the amide group with the aromatic system provided the preferred length for effective uptake inhibition, as exemplified by the comparison between the 2-(pyridin-3-yl)] ethyl, pyridin-3-ylmethyl and pyridin-3-yl head groups, which lead to IC$_{50}$ values of 101 nM, 2691 nM and 1242 nM, respectively (FIGS. 1A-B). The most potent compounds were those with an N-phenethyl head group, which showed IC$_{50}$ values in the low nanomolar range. Compared to the unsubstituted parent compound (IC$_{50}$=1142 nM), the presence of a single methoxy group at different positions of the aryl system was associated with approximately 4-fold increased potency (IC$_{50}$=198-271 nM) (FIGS. 1A-B). Potency could be further increased dramatically by 3,4- dimethoxylation, providing the highly potent and selective inhibitor (WOBE437) with an $IC_{50}$ value of 10±8 nM for AEA uptake inhibition (using 100 nM total AEA) and an outstanding 1000-fold selectivity over FAAH (FIGS. 1A-B). The structurally related benzodioxole and dihydrobenzodioxine analogs were approximately 13-times less potent (FIGS. 1A-B). Modifications in the acyl part of WOBE437 (chain length, degree of unsaturation) led to less potent analogs. The similarity between the head groups in WOBE437 and the minor EC N-arachidonoyl dopamine (NADA) prompted us to prepare and test (2E,4E)-dodecadienoyl dopamine and the arachidonic acid-based analog of WOBE437. Interestingly, the (2E,4E)-dodecadienoyl ethanolamine generated by linking the acyl chain of WOBE437 and the head group of AEA significantly lost potency ($IC_{50}$=3.47 µM).

Figure 2A:
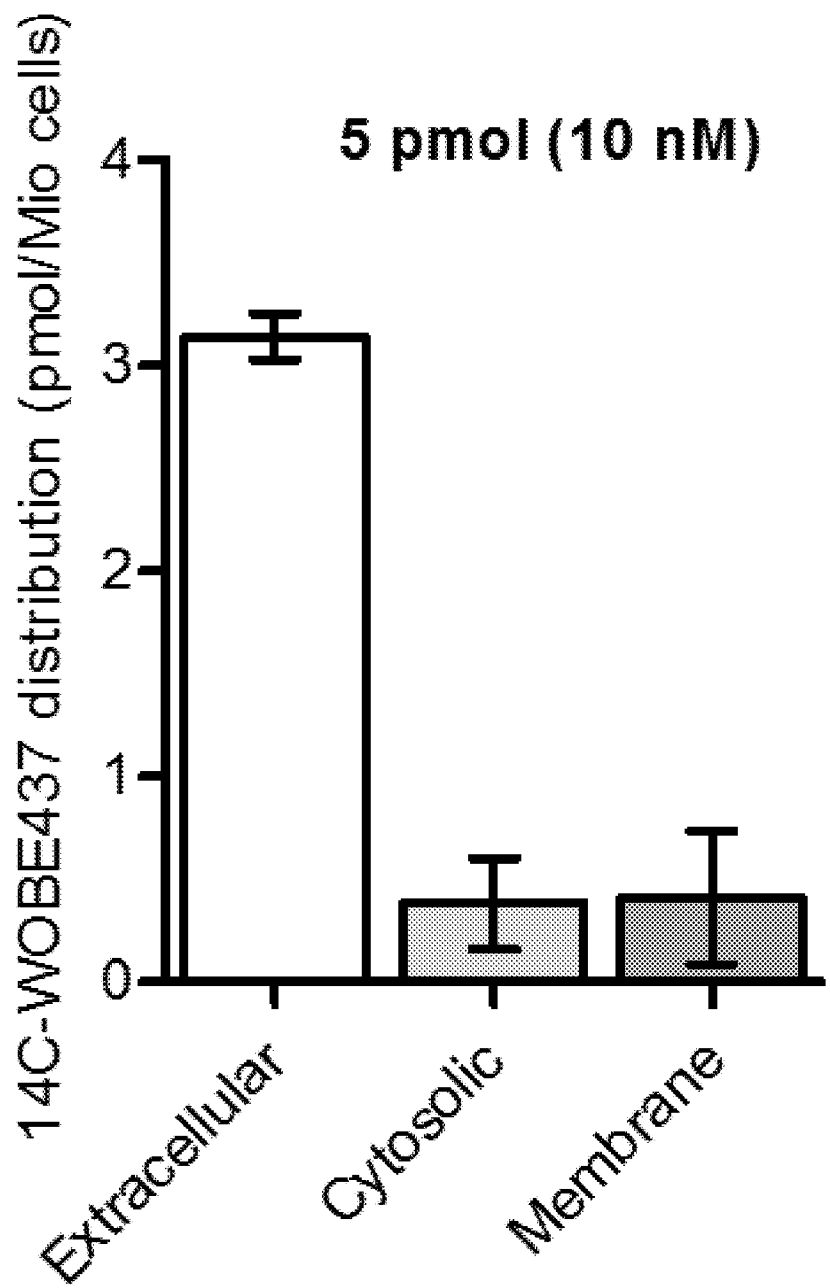
FIGS. 2A-2G. In vitro characterization of WOBE437.
Figure 2B:
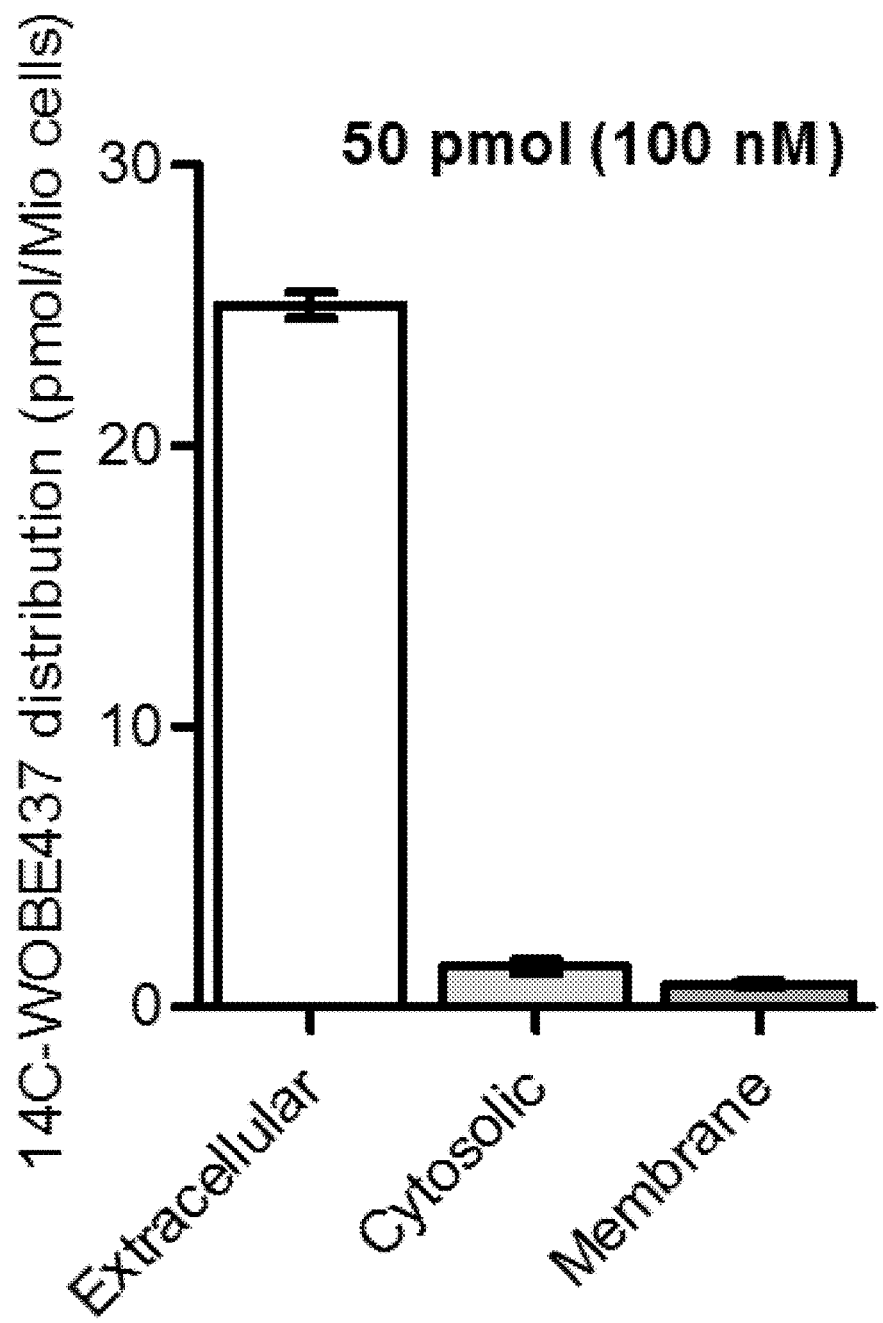
Figure 2C:
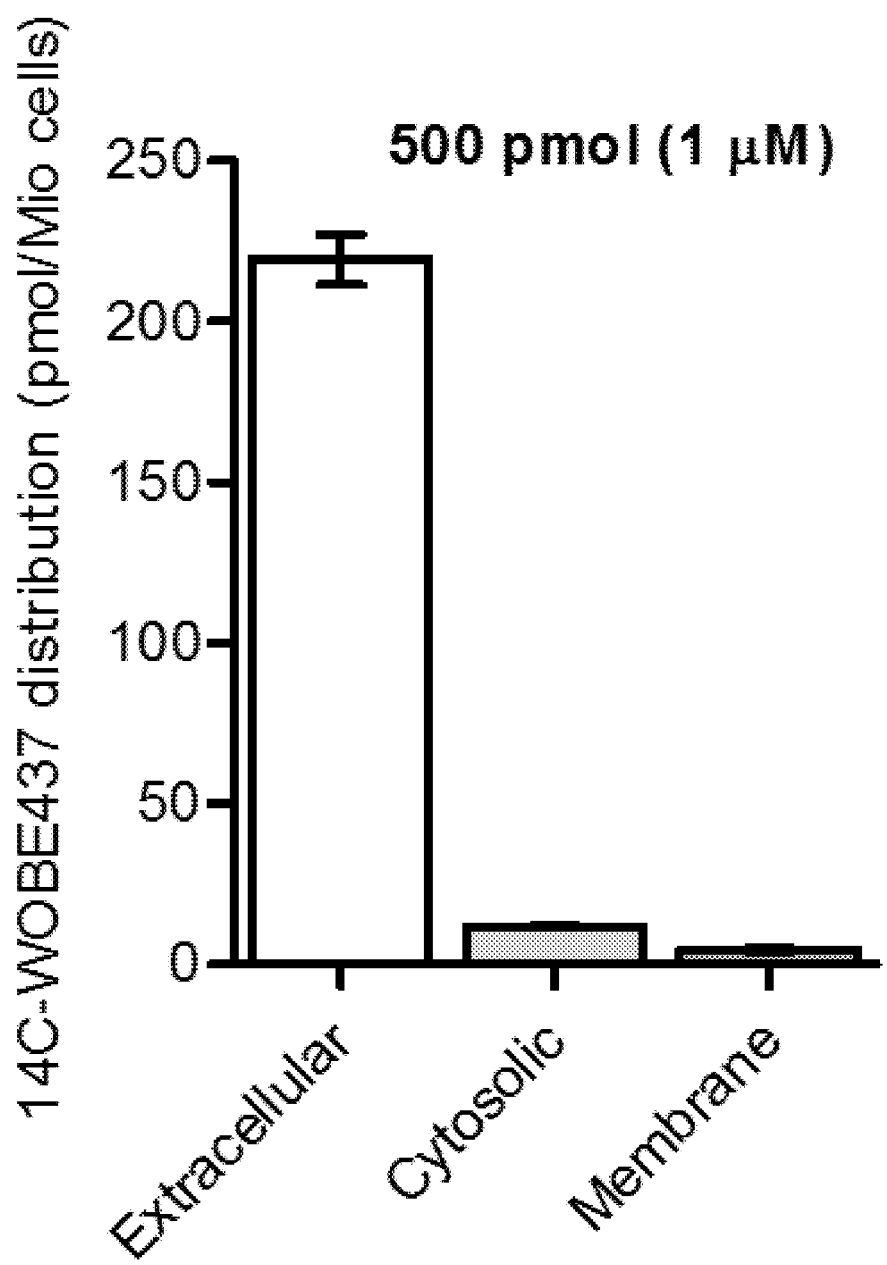
Figure 2D:
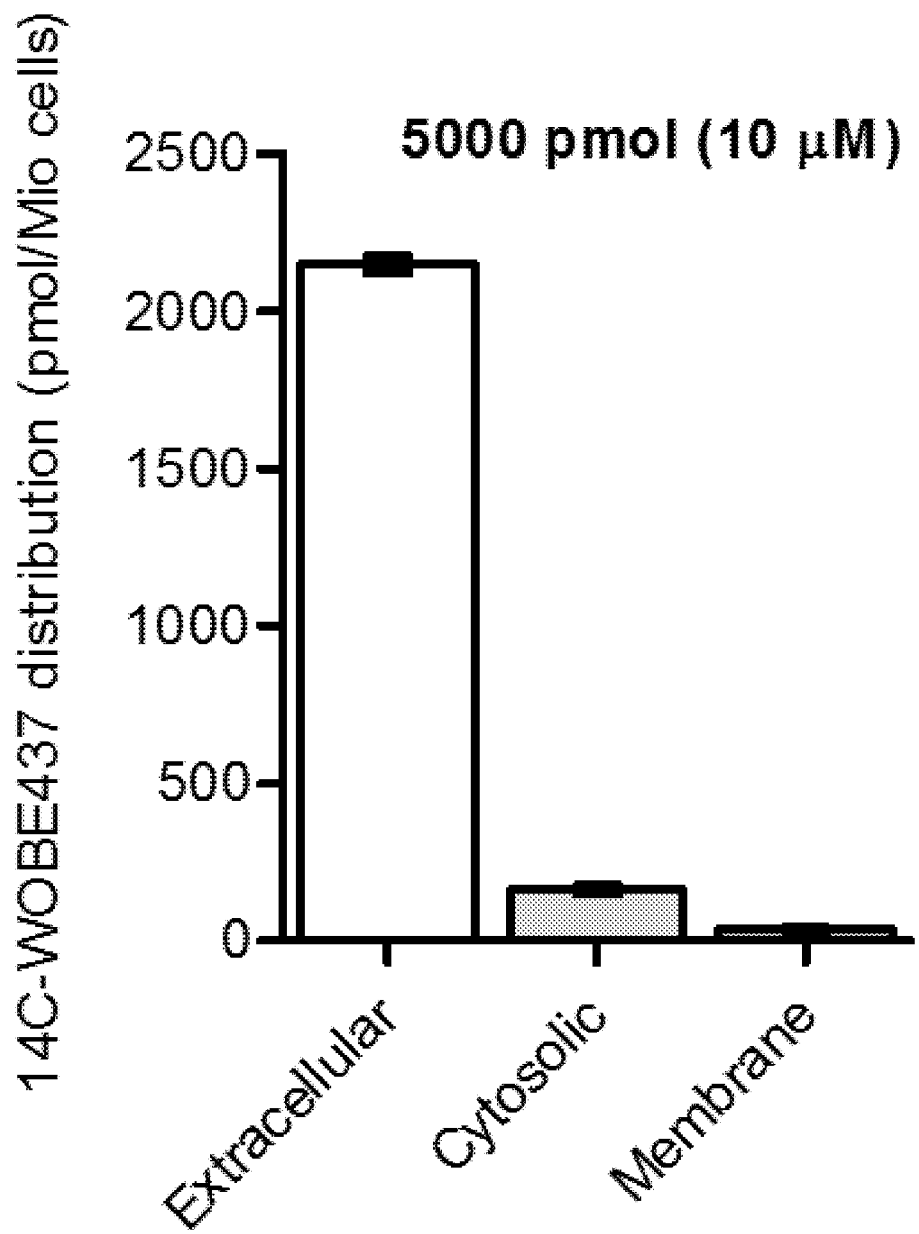
Figure 2E:
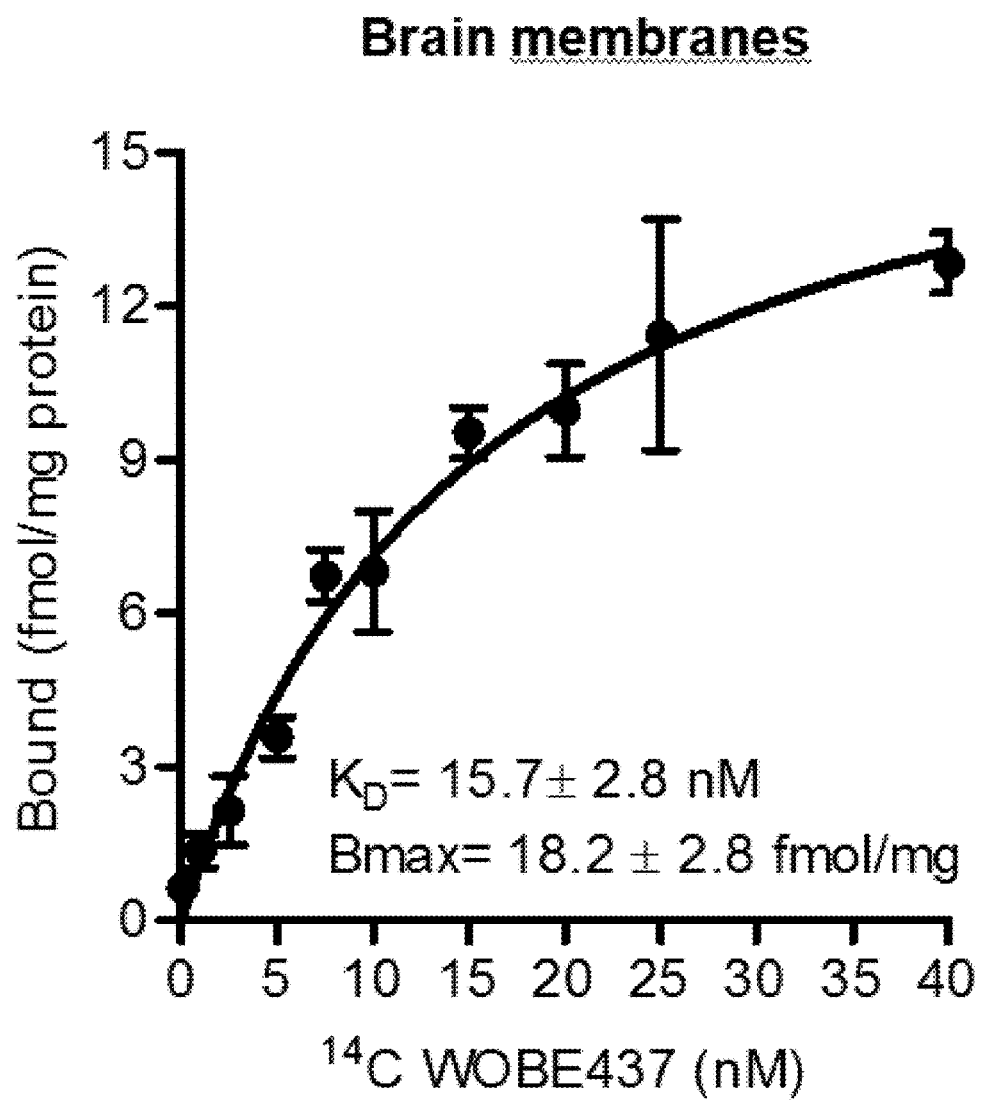
Figure 2F:
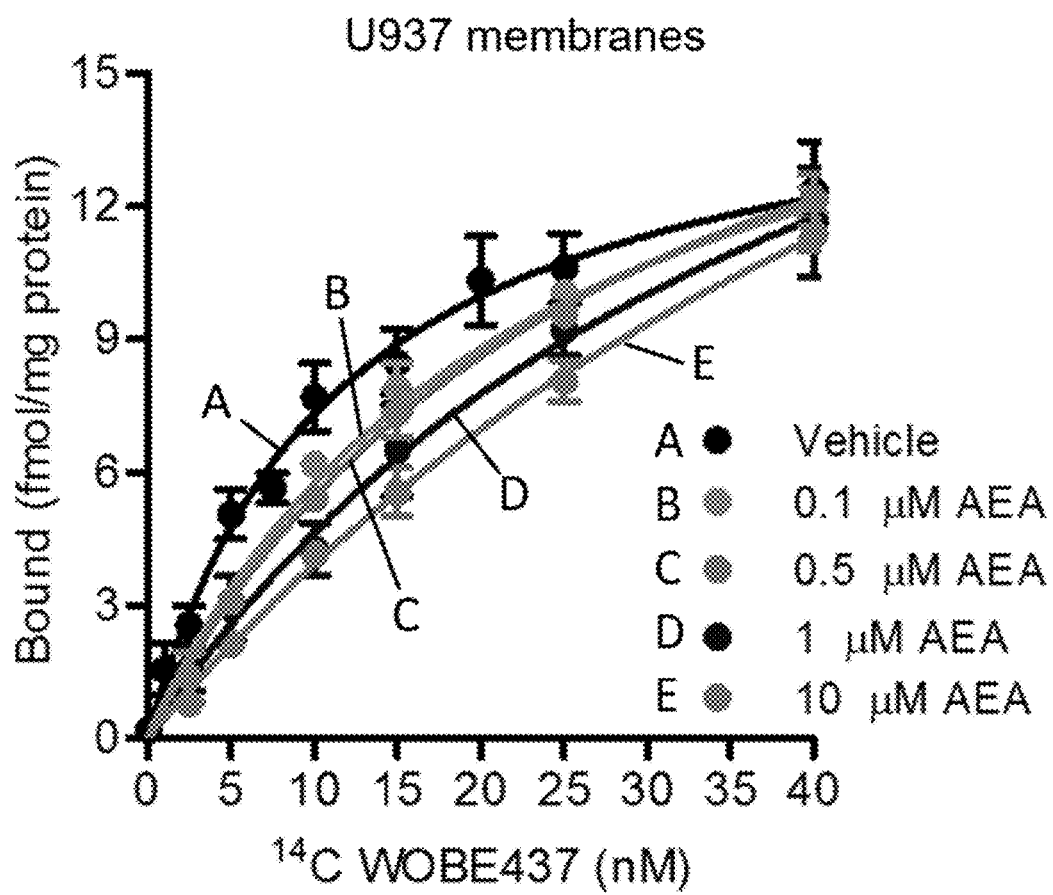
Figure 2G:
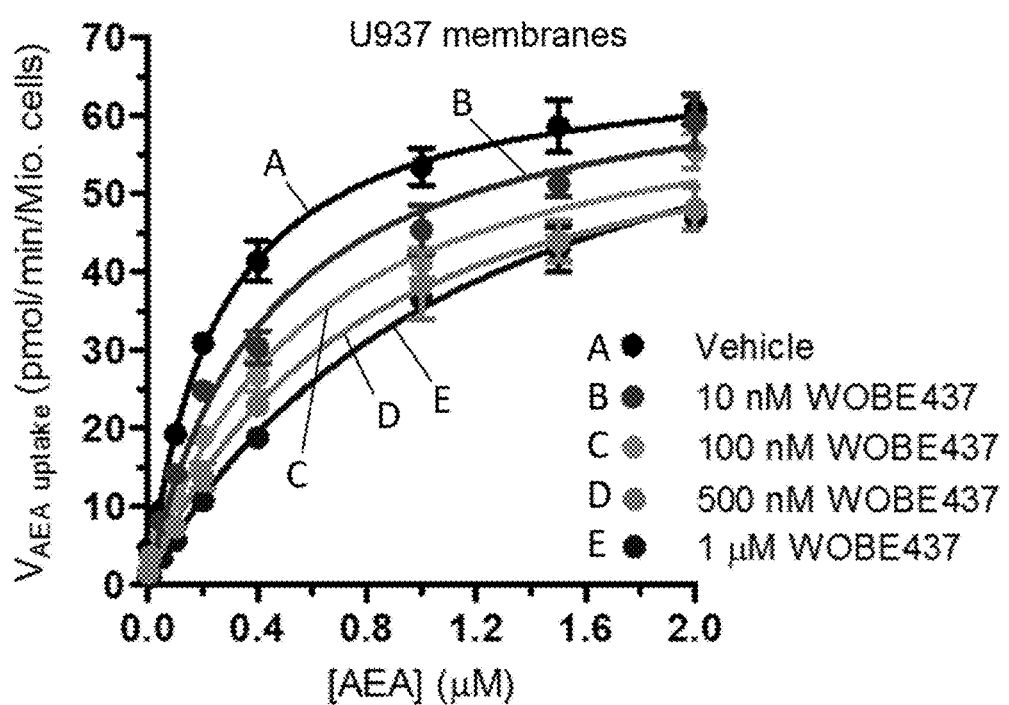

Biochemical and Pharmacological Profiling of WOBE437 Shows Functional Specificity In addition to their effects on AEA uptake, the inhibition of FAAH was thoroughly investigated for all nanomolar inhibitors. Several N-alkylamides exhibited dramatically improved selectivity for AEA uptake reduction over FAAH inhibition, as compared to any previously described non-selective and cell-permeable AEA uptake inhibitors (FIG. 1B). The lack of significant FAAH inhibition by WOBE437 was established in different assay systems using human recombinant enzyme, cell and brain homogenates. The compound did not significantly inhibit AEA hydrolysis in all biological matrices investigated ($IC_{50} \geq 10$ µM). On the other hand, WOBE437 showed low nanomolar potency for the inhibition of AEA uptake in different cell lines and assay formats, including the FAAH-deficient HMC-1 human mast cells (estimated $IC_{50}$ value of ~137 nM, Hill slope=−0.934), Neuro2a mouse neuroblastoma cells ($IC_{50}$=55±18 nM, Hill slope=−0.705, FIG. 1C) and U937 cells ($IC_{50}$=10±8 nM, Hill slope=−0.715), using the multiphase AEA uptake assay (FIG. 1D). Time-course experiments showed that in Neuro2a cells, WOBE437 (1 µM) inhibited AEA uptake by 35% after 2-10 min of incubation reducing the effect to 20% of inhibition after 15-20 min of incubation (FIG. 1E). Importantly, WOBE437 (1 µM) inhibited AEA uptake also in primary mouse cortical neurons by 50% after 2-7 min of incubation with a smaller inhibition (20-35%) upon longer incubation (10-20 min, FIG. 1F). WOBE437 inhibited 2-AG uptake (using 1 µM total 2-AG) in U937 cells with an $IC_{50}$ of 283±121 nM (Hill slope=−0.973, FIG. 1D). In Neuro2a cells, incubation with WOBE437 (5 µM) for 2 and 5 min reduced overall uptake by 40%. (FIG. 1G). Interestingly, the α/β-hydrolase domain-6 (ABHD6) inhibitor WWL70 prevented 2-AG uptake and hydrolysis occurring at later time points, unlike JZL184 which specifically inhibited hydrolysis. WOBE437 only inhibited 2-AG uptake but not hydrolysis (FIG. 1G). In agreement with the hydrolase activity-based protein profiling (ABPP) in mouse brain homogenate (FIG. 1H) and of classical radioactivity-based hydrolytic assays in other biological matrices, WOBE437 did not inhibit any of the 2-AG hydrolyzing enzymes MAGL, ABHD6, and ABHD12. Importantly, WOBE437 was completely stable in the presence of the main EC degrading enzymes. Furthermore, it did not inhibit COX-2 activity and exhibited no binding to fatty acid binding protein 5 (FABP5). As AEA and 2-AG transport was previously suggested to be bidirectional, the effect of WOBE437 on EC efflux and release in U937 cells was also explored. WOBE437 inhibited the efflux of AEA from pre-loaded cells and blocked the release of both ECs while increasing their intracellular levels in cells stimulated with ATP, thapsigargin and ionomycin. Then cells were treated with radiolabeled $^{14}$C-WOBE437 to investigate the cellular penetration of the compound. In U937 cells, the vast majority of the radioactive signal was collected in the extracellular and membrane-bound fractions (75-90%), with negligible amounts (5-9%) detected in the intracellular fraction (FIGS. 2A-D). Interestingly, the highest membrane-associated signal was shown at the concentration of 10 nM (9.8% of total signal), while at higher $^{14}$C-WOBE437 concentrations the membrane-associated radioactivity significantly dropped to 1.7%, 0.7% and 0.7% of total signal for the concentration of 100 nM, 1 µM and 10 µM, respectively (FIGS. 2A-D). This data suggested a saturable membrane target for WOBE437 (FIGS. 2A-D). In order to further investigate this point, $^{14}$C-WOBE437 was applied to membrane preparations generated in-house from mouse brain and U937 cells. Interestingly, the data showed a clear saturation binding kinetics with similar Kd (15.7±2.8 nM and 11.3±2.4 nM for mouse brain and U937 membranes, respectively) and Bmax values (18.2±1.5 fmol/mg protein and 15.6±1.4 fmol/mg protein for mouse brain and U937 membranes, respectively) (FIGS. 2E-F). The Kd values are in line with the $IC_{50}$ values shown in the functional AEA uptake assays in Neuro2a and U937 cells (FIGS. 1C and 1D). In further experiments, 10 nM of $^{14}$C-WOBE437 was co-incubated with different concentrations of AEA and U937 membranes. The results showed that increasing amounts of AEA induced a right-down shift of the $^{14}$C-WOBE437 binding curve leading to an increase of Kd values, while not significantly modifying Bmax values (FIG. 2F). Furthermore, the endocannabinoids AEA and noladin ether and the AEA uptake inhibitor OMDM-2 could compete with $^{14}$C-WOBE437 binding in brain and U937 membranes. Altogether, this data indicates a saturable membrane binding site for WOBE437 that is compatable with endocannabinoids and membrane transport inhibitors. In intact U937 cells, Michaelis-Menten analysis of AEA transport kinetics, showed a competitive type of inhibition (FIG. 2G). Secondary plots of the slope (Kmapp/Vmaxapp vs. [WOBE437]) and intercept (1/Vmaxapp vs. [WOBE437]) confirmed the competitive inhibition of AEA uptake. In further experiments, the mechanism of AEA uptake inhibition showed to be reversible (rapid dilution assay) and independent of pre-incubation time. Incubation of $^{14}$C-WOBE437 (100 nM) with U937 cells over time (0-30 min) did not show any increase of the cell-associated radioactive signal (approximately 10% of total signal). The same result was obtained by co-incubating $^{14}$C-WOBE437 with 50-times higher concentration of AEA, thus suggesting that WOBE437 does not act as a substrate of endocannabinoid transport.

Cell penetration was further investigated by quantifying intracellular levels of WOBE437 by LC-MS/MS and measuring its physicochemical distribution in the parallel artificial membrane permeability assay (PAMPA). Both result confirmed that WOBE437 does not significantly penetrate cell membranes.

Noteworthy, WOBE437 did not exhibit any significant interaction with 45 CNS-related receptors, including cannabinoid receptors, highlighting its specificity towards EC membrane transport. A full assessment of the concentration-dependent binding of WOBE437 to $CB_1$ and $CB_2$ receptors revealed only negligible binding interactions ($K_i$ values of 17 µM and 48 µM, respectively).

Pharmacological Effects of WOBE437 in Mice

WOBE437 was initially assessed in a battery of four individual tests typically associated with $CB_1$ receptor activation in mice (nociception, locomotion, body temperature and cataleptic behavior), collectively referred to as the "tetrad". Dose-response experiments identified 10 mg/kg as the lowest dose to elicit a moderate but complete tetrad in BALB/c mice upon intraperitoneal (i.p.) administration (FIGS. 3A-D). Compared to the $CB_1$ receptor agonist (R)-WIN55,212-2, the observed hypothermia, catalepsy and antinociception were significantly less pronounced, whereas the reduction in locomotion was comparable. To assess whether the WOBE437-induced effects were $CB_1$ receptor-mediated, mice were pre-treated with the selective antagonist/inverse agonist rimonabant (SR1). As in the case of (R)-WIN55,212-2, the WOBE437-induced hypothermia, catalepsy and antinociception were completely blocked by SR1 while hypolocomotion was partially reversed (FIGS. 3A-D). The tetrad was fully replicated in wild-type C57BL6/N mice and completely absent in $CB_1$ receptor-deficient littermates. These experiments provided a proof-of-concept for the mechanism of action of WOBE437 as a novel "indirect $CB_1$ receptor agonist". In subsequent studies, the effects of WOBE437 in pain, inflammatory and anxiety models were investigated. At doses of 5 and 10 mg/kg, WOBE437 elicited significant analgesic and anti-inflammatory effects, as indicated by the reduced number of abdominal stretches in the acetic writhing test, comparable to indomethacin (5 mg/kg), and by protective effects in lipopolysaccharides (LPS)-induced endotoxemia in BALB/c mice (FIGS. 3E-F). Both effects were reversed by SR1. In the formalin test, WOBE437 reduced inflammatory pain and paw thickness comparable to indomethacin (5 mg/kg) (FIGS. 3G-H). At the lower dose of 3 mg/kg, WOBE437 showed significant anxiolytic effects in C57BL6/N mice in the elevated plus maze (EPM) and in the holeboard (HB) test (Figs. eI-J). The number of entries and the time spent in the open arms of the EPM were both significantly increased compared to vehicle-treated animals (FIG. 3I). The anxiolytic effect was completely blocked by SR1, indicating an indirect $CB_1$ receptor-mediated mechanism for WOBE437. The same dose of 3 mg/kg was ineffective in the tetrad test and did not alter locomotion in the EPM assay. In the HB test, the head dipping frequency was significantly increased after 1 h post injection, thus reconfirming the anxiolytic effect of WOBE437 (FIG. 3J).

WOBE437 Selectively Modulates 2-AG and AEA Concentrations in Mice

In order to investigate whether there was a link between the in vivo pharmacological effects of WOBE437 and the inhibition of EC uptake in vitro, the levels of WOBE437, AEA, 2-AG and related lipids in different tissues were quantified by LC-MS/MS. After i.p. injection of 10 mg/kg of WOBE437 the peak plasma concentration of 492±103 was reached after 15 min and decreased with a half-life of 203 min (FIG. 4A). In the brain, the highest concentration was measured after 30 min (919±314 mol/g brain), remaining unchanged up to 1 h (652±165 pmol/g brain). The $C_{brain}/C_{plasma}$ ratio (Kp) of WOBE437 was 0.65 after 5 min, 1.64 after 15 min and reached 1.9 after 30 and 60 min (FIGS. 4A and 4E). The peak concentration of WOBE437 in the brain was 780±267 nM, thus being in line with the bioactive concentrations determined in cellular assays. WOBE437 did not inhibit any of the major serine hydrolases in vivo. After single and repeated injection(s), AEA and 2-AG levels in the plasma were not significantly affected by WOBE437 (FIGS. 4B-C). Only at 15 min post-injection, WOBE437 prevented the moderate increase of 2-AG induced by DMSO (FIG. 4C). Interestingly, although WOBE437 did not alter corticosterone levels after a single injection, it doubled the circulating concentration of corticosterone after 7 days (FIG. 4D). In the brain, AEA levels did not change compared to basal level after a single injection with WOBE437 (FIG. 4F). On the contrary, 2-AG levels increased 1.7-fold compared to vehicle at 1 h post-injection (FIG. 4G). After 7 days of daily treatment, both AEA and 2-AG levels were significantly raised by 1.5-fold compared to DMSO. The moderate but significant increase of both ECs in the brain did not affect the number of functional $CB_1$ receptors. Repeated administrations of WOBE437 led to a significant 3-fold increase of corticosterone in the brain, which mirrors the changes observed in plasma (FIG. 4H). In peripheral organs, WOBE437 reached peak concentrations of 5-20 nmol/g tissue, without any signs of accumulation over 7 days. After a single injection, the AEA level did not change in liver, whereas in kidney and spleen it moderately diminished. Similarly, 2-AG levels were not altered in the spleen, but dropped significantly after 60-360 min in liver and kidney. However, EC concentrations were not affected by repeated administrations of WOBE437 in peripheral tissues. Again, corticosterone levels were increased in spleen, liver and kidney. Importantly, the concentrations of other lipids (NAEs, AA, prostaglandins and progesterone) were not significantly altered upon WOBE437 treatment in brain, plasma and peripheral organs. The tissue distribution of $^{14}$C-WOBE437 (10 mg/kg, i.p.) in C57BL6/N mice after 1 h was also determined and the highest $^{14}$C signal was measured in adipose tissue followed by the spleen, liver and kidney. The LC-MS/MS and the $^{14}$C isotope quantifications provided a comparable tissue distribution of WOBE437, indicating its CNS bioavailability.

Discussion

WOBE437 inhibits AEA and 2-AG cellular uptake at sub-stoichiometric concentrations (relative to the ECs) without altering the levels of other NAEs in cell lines and human whole blood, thus represents the first suitable selective EC uptake inhibitor. Intriguingly, despite WOBE437 can inhibit EC release and reuptake, the net effect observed in complex matrices (i.e. whole blood and mice) showed an increase of EC levels. Additionally, WOBE437 membrane target can be differentially involved in EC reuptake and release as compared to other mechanisms. Indeed, residual AEA and 2-AG reuptake upon WOBE437 treatment is approximately 20-30% while it can inhibit only 20% of EC release (i.e. 80% residual release).

Binding kinetics indicated that WOBE437 binds to a membrane site with high affinity (10-20 nM). WOBE437 is hydrolytically stable and after i.p. administration at 10 mg/kg rapidly and efficiently accumulates in the brain (Kp>1 after 15 min). In mice, 10 mg/kg of WOBE437 elicited a full tetrad response, which is a hallmark of either direct $CB_1$ receptor activation or the simultaneous elevation of AEA and 2-AG levels in the brain (FIGS. 3A-D). In contrast, FAAH inhibitors only trigger analgesia, while MAGL inhibitors induce hypolocomotion, hypothermia and analgesia, but not catalepsy. The LC-MS/MS data showed that in total brain tissue, acute WOBE437 treatment significantly increased 2-AG levels without affecting AEA (FIGS. 4F and 4G). At 5-10 mg/kg, WOBE437 elicited significant analgesic and anti-inflammatory effects in different animal models; at the sub tetrad-inducing dose of 3 mg/kg, the inhibitor exhibited anxiolytic effects in two mouse models of anxiety behavior (FIGS. 3I and 3J), similar to FAAH and MAGL inhibitors.

Intriguingly, after 7 days of treatment, both AEA and 2-AG levels had significantly increased in the brain by a factor of 1.5 compared to vehicle. Similarly, WOBE437 accumulated in the brain, reaching an estimated concentration of 926 nM after 7 days of treatment (10 mg/kg i.p., daily) compared to 555 nM 1 h after a single injection (FIGS. 4A and 4E). The levels of other NAEs remained essentially unchanged, suggesting that FAAH activity was not affected, which is also in agreement with the minor cell penetration of WOBE437 (FIGS. 2A-D). The moderate increase of AEA and 2-AG concentrations induced by WOBE437 did not alter the number of functional $CB_1$ receptors in the brain. In contrast, the prolonged 2-AG "overflow" (10-12 times basal levels) resulting from repeated administrations of JZL184 has been shown to desensitize $CB_1$ receptors. However, repeated low doses of JZL184 in combination with FAAH inhibition produce antinociceptive and anxiolytic effects without causing $CB_1$ functional antagonism. Similarly, a reversible MAGL inhibitor showed protective effects in a mouse model of multiple sclerosis after 21 days of treatment which was associated with a 2-fold increase of 2-AG levels in the brain. The data show that a selective competitive EC reuptake inhibitor modulates the homeostasis of AEA and 2-AG levels in a time- and space-restricted manner without leading to an EC overflow or altering the levels of other lipids.

Importantly, after repeated administrations WOBE437 (10 mg/kg) did not significantly alter the levels of AEA, 2-AG and NAEs in kidney and liver. This represents another pharmacological difference/advantage between the inhibition of EC reuptake and the blockage of EC degradation. The possibility to tissue-specifically increase EC levels provides a new targeted-approach without leading to chronic activation of liver and kidney $CB_1$ receptors that exacerbate inflammation, promoting liver and renal fibrosis, insulin resistance, steatosis and nephropathy.

Unexpectedly, upon repeated administration WOBE437 led to a significant 2-4 fold increase of the corticosterone levels in brain, plasma and peripheral organs (FIGS. 4D and 4H). Although this requires further investigations, the modulation of corticosterone (the rodent equivalent of cortisol) concentrations is interesting. A potential correlation between $\Delta^9$-THC-induced suppression of neuroinflammation and activation of the hypothalamic-pituitary-adrenal (HPA) axis in multiple sclerosis was recently discussed. Although stress conditions are usually characterized by high cortisol levels, burnout patients have an impaired response of the HPA axis which leads to hypocortisolism. In these patients, the chronic low level of cortisol has been correlated with the severity of clinical and non-clinical symptoms.

The data show that EC membrane trafficking and cellular reuptake can be targeted. The potent and selective blockage of EC membrane transport by WOBE437 represents a novel type of pharmacological modulation of the ECS. This strongly indicates that EC transport mechanisms play a crucial role in the brain. Being a selective low nanomolar EC transport inhibitor WOBE437 is not only a suitable tool compound to study lipid membrane transport mechanisms, which is highly challenging, but also addresses the need of high quality chemical probes for research.

Material and Methods

Inhibition of AEA and 2-AG Uptake and Release in Different Cell Types

All radioactivity-based AEA and 2-AG uptake and release assays performed in U937, and HMC-1 cells were carried out using two different assay formats as previously reported. AEA and 2-AG uptake assay in Neuro2a and primary mouse cortical neurons were performed with a different method disclosed in Chicca 2017.

Activity-Based Protein Profiling (ABPP)

ABPP experiments were performed using membrane preparations obtained from mouse brains as described earlier.

Enzyme Activity and Metabolic Stability Assays

FAAH, ABHDs, MAGL and COX-2 activity assays were performed using cell homogenates, human recombinant enzymes and mouse, rat and pig brain homogenates as previously described.

Binding Assay, CB1 Functional Assays and In Vitro Pharmacological Screening $CB_1$ and $CB_2$ receptor binding assays [$^{35}$S]GTPγS assays were performed as previously described. WOBE437 was profiled in more detail in an extended CNS adverse drug reaction screening panel (CEREP).

Localization and Quantification of $^{14}$C-WOBE437 in Cellular Fractions of U937 Cells and Mouse Tissues The cell penetration and tissue distribution of $^{14}$C-WOBE437 was assessed in U937 cells and C57BL6/N mice as described in Chicca 2017.

In Vivo Experiments in BALB/c, C57BL6 and Phenotypic CB1-KO Mice

WOBE437 and RX-055 were tested in independent laboratories, in different mouse strains and in multiple (behavioral) models for cannabimimetic, analgesic, anti-inflammatory and anxiolytic-effects in wild-type and phenotypical $CB_1$-KO mice as described in Chicca 2017.

LC-MS/MS Quantification of WOBE437, Endocannabinoids and Other Lipids

WOBE437, AEA, 2-AG, other lipids and hormones were quantified by LC-MS/MS in different biological matrices (cells, human whole blood, rodent tissues) as reported in Chicca 2017.

Example B2) Biochemical Evaluation of WOBE437—Further Characterization

The aim of this study was to assess the oral bioavailability of WOBE437 to the brain and obtain data on its tissue distribution over time. The oral dose of WOBE437 could be correlated with both its pharmacological effect in acute pain and overall modulation of lipids related to the ECS. It was shown that in chronic inflammation, the action of WOBE437 is mediated via different receptors, thus reflecting the pleiotropic action of ECs in complex pathophysiological conditions. These data indicate that the selective inhibition of EC reuptake is a therapeutic strategy for chronic inflammatory conditions in which different receptors and signaling pathways cooperate in the etiopathology.

Material and Methods

Animals.

Male BALB/c or male C57BL6/J mice (8 to 10 weeks old; 20-25 g body weight) were either supplied by the Centro de Investigación Biomédica de Occidente or Jackson Laboratory and kept under standard environmental conditions (24±2° C.; light-dark cycle of 12:12 h) with food and water ad libitum. Mice were handled according to Mexican Federal Regulations for the Care and Use of Laboratory Animals NOM-062-ZOO-1999 (Mexican Ministry of Health) and according to the Swiss federal guidelines, which is in accordance with the Code of Ethics of the Directive 2010/63/EU.

Oral Bioavailability Experiments.

Male C57BL6/J or male BALB/c mice were orally administered by gavage with 10, 25, 50 or 100 mg/kg of WOBE437 (100 µL; olive oil and ethanol 8:2) using a metal feeding needle (20G, Kent Scientific, USA). The mice were sacrificed by decapitation after gavage administration.

Brain, blood, liver, kidney and spleen were collected for the LC-MS/MS analyses. All tissues were briefly washed with ice cold PBS and immediately snap-frozen and stored at −80° C. Whole brain samples were dissected between the hemispheres. Blood samples were immediately centrifuged to obtain plasma, which was stored at −80° C.

Quantification of WOBE437 and Endocannabinoid Levels by LC-MS/MS.

Samples extractions and LC-MS/MS measurements were performed as previously described (Chicca et al., 2017). Briefly, tissues were weighted and transferred in to extraction tubes containing three steel beads and 0.1 M formic acid. Tissues were homogenized and rapidly transferred to glass tubes containing 1.5 mL of ethyl acetate:hexane (9:1) 0.1% formic acid and internal standards (ISs). Samples were centrifuged and the organic phase was recovered. After evaporation, the extracts were reconstituted in 200 µL of ACN:ddH$_2$O (8:2). 10 µL of the solution were injected in the LC-MS/MS system using the same LC and ionization protocols as described (Chicca et al., 2017).

Microsomal Clearance.

Human or mice microsome clearance experiment were carried out as according to a previously describe protocol. Briefly, microsome preparation (0.5 mg/mL) plus cofactor NADPH solution was incubated with 1 µM of WOBE437 in 96-well plates at 37° C. After 1, 3, 6, 9, 15, 25, 35 and 45 min, 40 µL of the preparation was transferred and quenched with 3:1 (v/v) acetonitrile containing internal standards. Samples were then cooled and centrifuged before analysis by LC-MS/MS. Log peak area ratios (test compound peak area/internal standard peak area) are plotted against incubation time using a linear fit. The calculated slope is used to determine the intrinsic clearance. Data are obtained from single experiments measured with multiple time-points.

Hot Plate Test.

Acute pain was evaluated 1 h after gavage administration of WOBE437, at 10, 25, 50 and 100 mg/kg in BALB/c mice. The test was performed using a clean 54-56° C. hot plate (Thermo Scientific, USA) with a Plexiglas cylinder. The latency to show the first nociceptive response (paw lick or foot shake) was measured. In order to evaluate CB1 receptor antagonism, 5 mg/kg of rimonabant (Pharmasery AG, Switzerland) was injected intraperitoneally (i.p.) (20 µL, in DMSO) 30 min before WOBE437 administration.

Tetrad Test.

The tetrad test was performed in the following order: rectal temperature, catalepsy, locomotion and analgesia. Rectal temperature was measured before (basal) and 1 h post gavage administration by using a thermocouple probe (Physitemp Instruments Inc., USA) and results were reported as the difference (Δ) between both temperatures. The bar test was used to evaluated catalepsy by placing the mouse in an imposed position with both forelimbs resting on a bar of 4 cm high; the end point of catalepsy was considered when both front limbs were removed or remained over 120 s. Locomotor activity was determined by placing the mouse on a rotarod (Erweka, Germany) at 4 rpm, the latency to fall was measured with a cut-off time of 120 s. Each mouse was previously trained to walk over the rotarod for at least 120 s. Catalepsy and locomotion were measured in three trials. Analgesia was evaluated with the hot plate test, each mouse was placed in a 54-56° C. hot plate (Thermo Scientific, USA) with a Plexiglas cylinder, the latency to first nociceptive response (paw lick or foot shake) was measured.

Mouse Model of Complete Freund's Adjuvant Induced Monoarthritis.

BALB/c mice were anesthetized with xylazine/ketamine (5 and 10 mg/kg, respectively) and subsequently monoarthritis was induced by intra-articular injection of complete Freund's adjuvant (CFA, 40 µL; Sigma-Aldrich, St. Louis, USA) into the right knee joint. The inflammation was allowed to develop for 14 days prior to pharmacological treatments starting at day 15 for 1 or 3 days, respectively. Mechanical sensitivity (allodynia) and knee diameter (edema) were evaluated 1 h post treatment in the ipsilateral and contralateral knees. Articular sensitivity was evaluated using a digital algometer (Bioseb, USA). The knee withdrawal threshold was determined by applying slow increments of force into the joint until the mice showed a signal of pain (withdrawal reflex or vocalization). A cut-off force of 300 g was considered to avoid damage in the tissue. The measurements were done in triplicates and the average was considered for the statistical analysis. To evaluate the degree of inflammation, knee diameter was measured in both extremities using a digital micrometer (Mitutoyo, USA). WOBE437 was administered at doses of 2.5, 5 or 10 mg/kg, either as single dose or for 3 days treatment. To evaluate the involvement of CB1 and CB2 receptors, TRPV1 and PPARγ, rimonabant (5 mg/kg, CB1 receptor antagonist/inverse agonist), SR144528 (3 mg/kg, CB2 receptor antagonist/inverse agonist; Cayman Chemical, USA), capsazepine (5 mg/kg, TRPV1 antagonist; Tocris Bioscience, UK) and GW9662 (3 mg/kg, PPARγ antagonist; Tocris Bioscience, UK) were injected 30 min before WOBE437 administration. Indomethacin (5 mg/kg; Sigma-Aldrich, USA) was used as a reference drug (positive control). For all the compounds, dimethylsulfoxide (DMSO) was used as vehicle (20 µL, i.p.).

Open Field Test.

Potential motor changes were evaluated in an open field box (40×40×30 cm, Plexiglas). The mice were individually placed in the center and allowed to move freely for 5 min. The locomotion activity was recorded with the OpenFieldTest© and traveled distance was evaluated automatically. After every experiment, the box was cleaned with 70% ethanol to remove odors.

Real-Time PCR.

To evaluate gene expression of CB receptors and the main enzymes involve in AEA and 2-AG biosynthesis, somatosensory cortex, thalamus and knee articular tissue were recover after 3 days of treatment with vehicle or WOBE437 in the complete Freund's adjuvant induced monoarthritis model. Total RNA extraction and reverse transcription were carried out with a previously described protocol. The kit LightCycler® FastStart DNA Master$^{PLUS}$ SYBR Green I (Roche, USA) was used for the real-time PCR, according to manufacturer protocol, and the reaction was performed in the LightCycler 2.0 equipment (Roche, USA). The relative gene expression was calculated by using the method known as $2^{\wedge}(-\Delta\Delta Ct)$ (Livak and Schmittgen, 2001). ΔΔCt was calculated using the following formula:

$$\Delta\Delta Ct = (Ct_{TE} - Ct_{HE}) - (Ct_{TC} - Ct_{HC})$$

$Ct_{TE}$: Ct for the tested gene (Cnr1, Cnr2, Nape-pld, Dagla) in the experimental or control group $Ct_{HE}$: Ct for the housekeeping gene (Actb) in the experimental or control group $Ct_{TC}$: mean Ct for the tested gene in the control group $Ct_{HC}$: mean Ct for the housekeeping gene in the control group Finally $2^{\wedge}(-\Delta\Delta Ct)$ was calculated to obtain the fold change of gene expression. Every sample (n=6-15, per group and region) was analyzed in duplicated and the mean value was considered for ΔΔCt calculation. Beta-actin was used as the housekeeping gene and mean of vehicle group was used as a calibrator.

Statistical Analysis.

All data are presented as mean values±SD and were analyzed by nonparametrical methods using a Kruskal-Wallis test followed by Mann-Whitney U as a post hoc test. A confidence level of p<0.05 was considered statistically significant. Analyses were carried out using the GraphPad Prism software version v5.0 (La Jolla, Calif.).

Results

The Endocannabinoid Reuptake Inhibitor WOBE437 is Orally Bioavailable

Figure 5A:
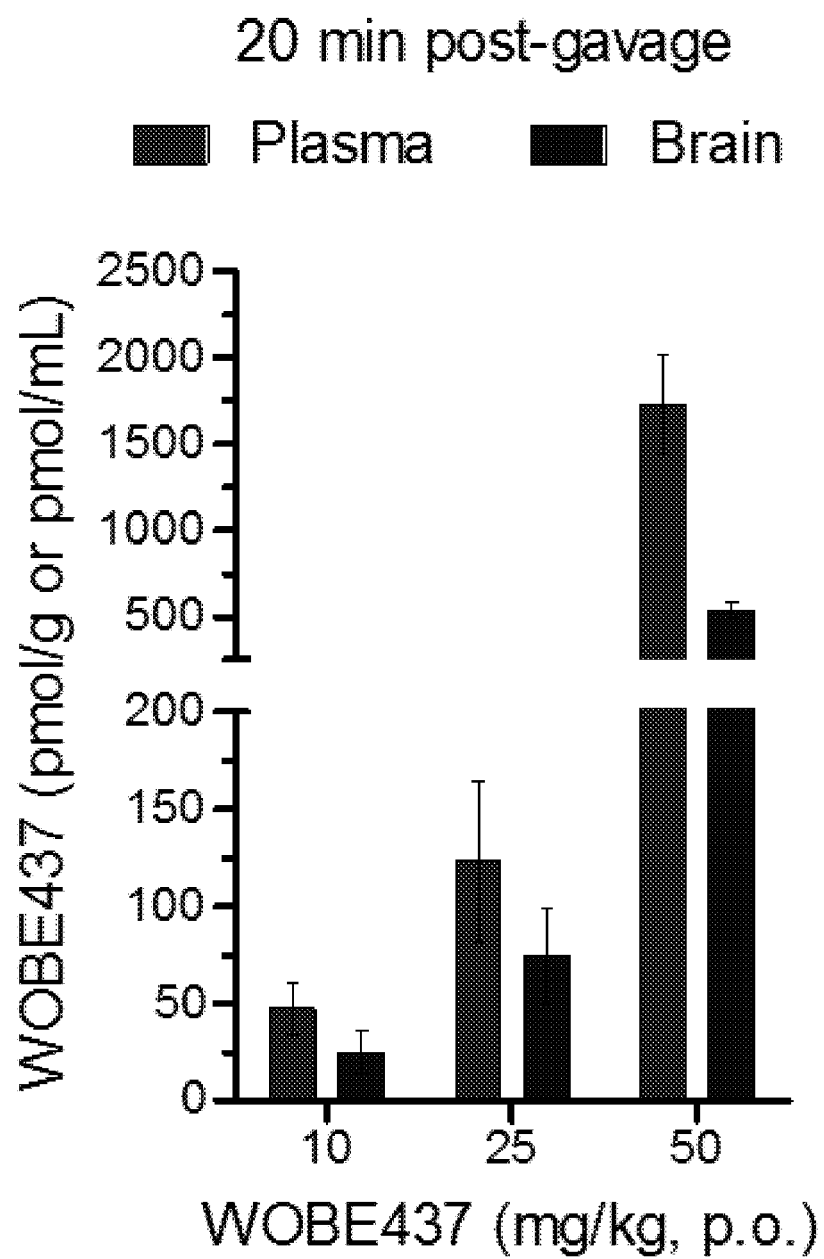
FIGS. 5A-5C. WOBE437 is rapidly biodistributed after oral administration in C57BL6 male mice.
Figure 5B:
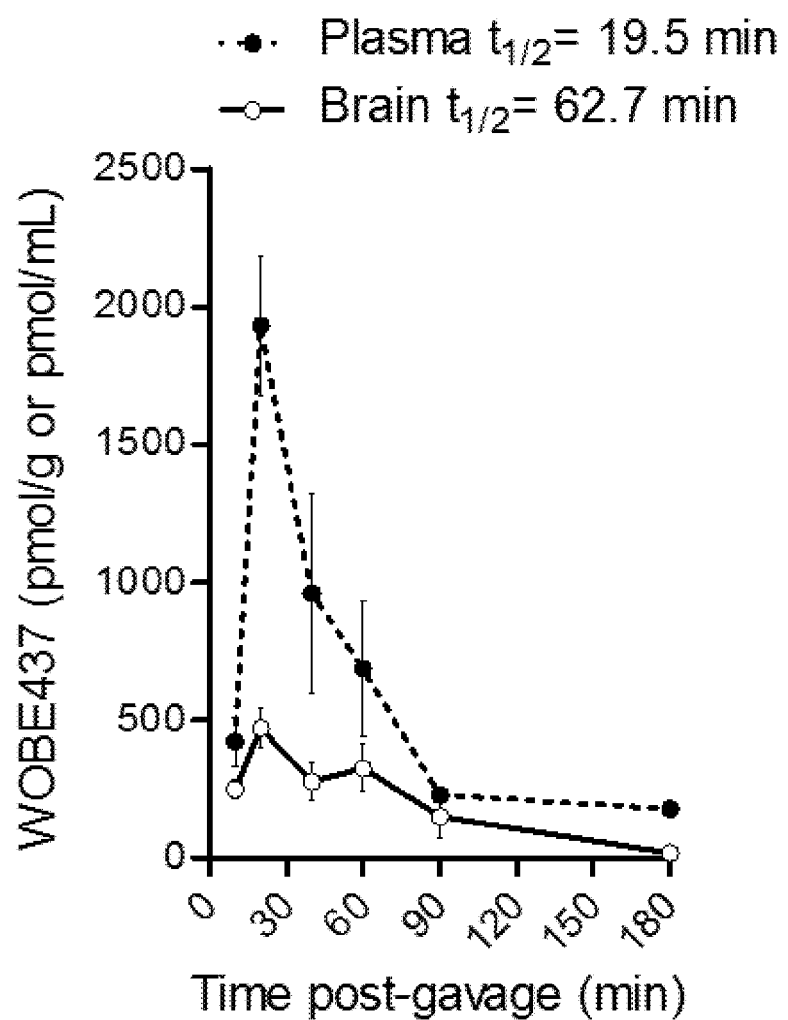
Figure 5C:
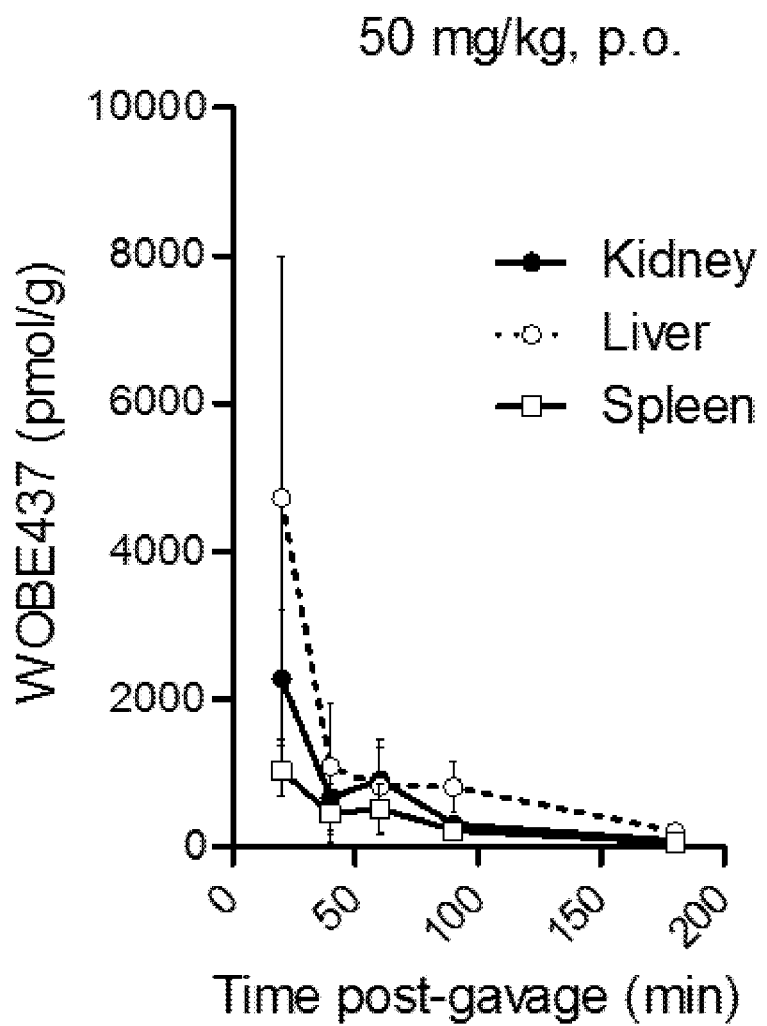

Oral administration of WOBE437 in male C57BL6/J mice showed a complete biodistribution after 20 min, with corresponding brain levels of 24.7±25.3 pmol/g using a dose of 10 mg/kg and 534.5±109.9 pmol/g using a dose of 50 mg/kg (FIG. 5A). In plasma, WOBE437 reached 47.3±32.5 pmol/mL and 1731.5±703.4 pmol/mL after oral doses of 10 or 50 mg/kg, respectively (FIG. 5A). In order to characterize the tissue distribution of WOBE437 over time, brain and plasma samples were recovered at different time-points (10, 20, 40, 60, 90 and 180 min) after gavage administration of 50 mg/kg. The highest concentration of WOBE437 was found at ≤20 min ($t_{max}$), reaching apparent $C_{max}$ values of 471.7±182.6 pmol/g in brain and 1931±564 pmol/mL in plasma, respectively (FIG. 5B). The apparent volume of distribution (Vd) at $C_{max}$ was 80.4 L/kg and at the steady state 609 L/kg, thus large and reflecting lipid solubility and massive tissue penetration/retention. In brain, the value obtained with 50 mg/kg p.o. is equivalent to an estimated concentration of 399.7±154.7 nM. WOBE437 is cleared from the brain after approximately 180 min. Furthermore, in kidney, liver and spleen, the $t_{max}$ values of WOBE437 were 20 min after administration (FIG. 5C). The highest concentration was found in liver with 4720±3273 pmol/g, followed by kidney (2277±916 pmol/g) and spleen (1030±339 pmol/g). Between 20 and 40 min, the hepatic concentration of WOBE437 showed the most significant reduction, dropping by a factor 4 from 4720 to 1080 pmol/g (FIG. 5C). In preliminary experiments with human and mouse liver microsomes the clearance of WOBE437 was estimated as 657 µL/min/kg and 174 µL/min/kg, respectively (FIG. 6). These values suggested an estimated maximal bioavailability of 17% in mice and 4% in humans.

Nociceptive Effect after Single Oral Dose of WOBE437

Figure 7A:
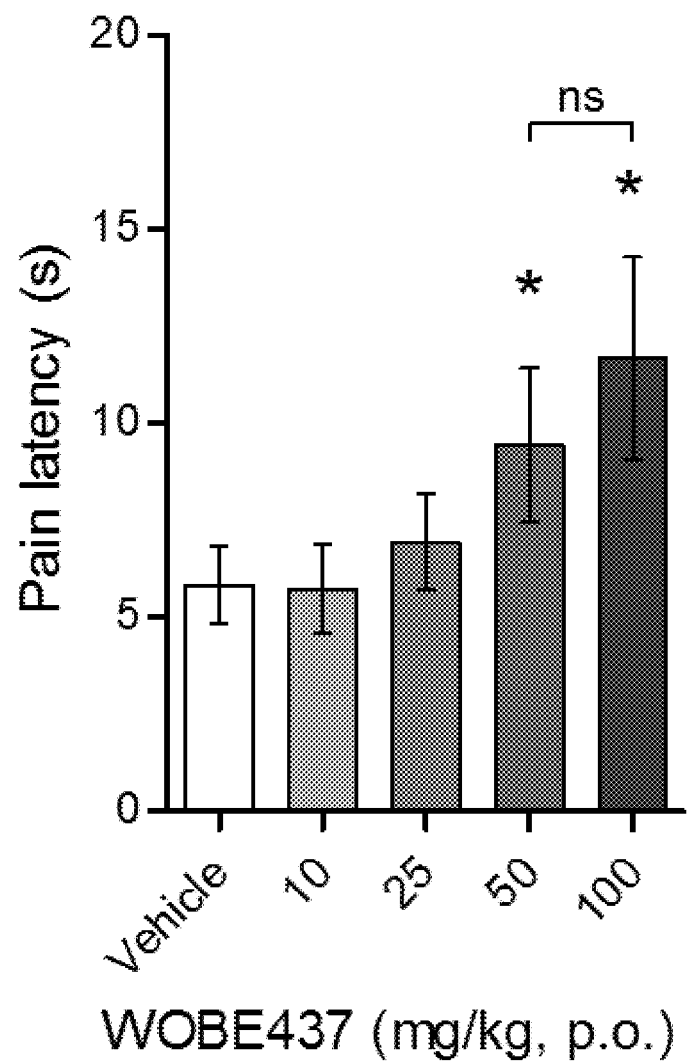
FIGS. 7A-7B. Oral administration of WOBE437 attenuates acute pain in the hot plate test in BALB/c male mice in a CB1 receptor-dependent manner.
Figure 7B:
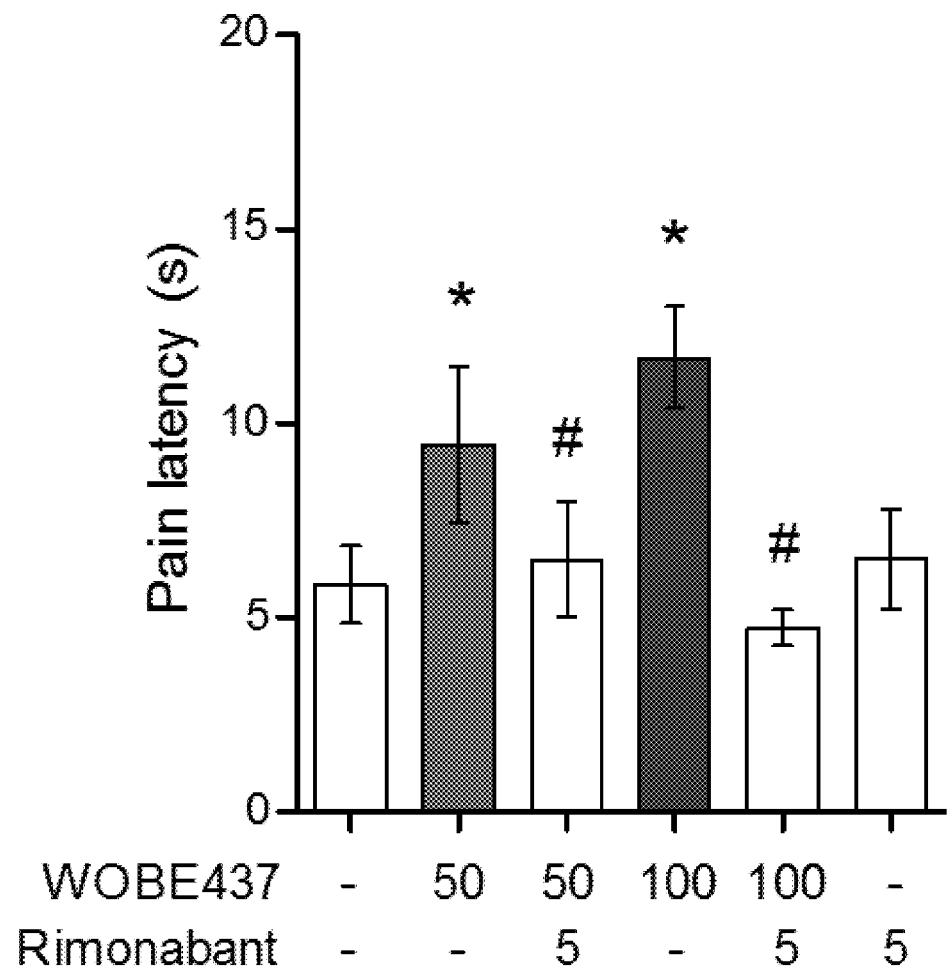
Figure 8A:
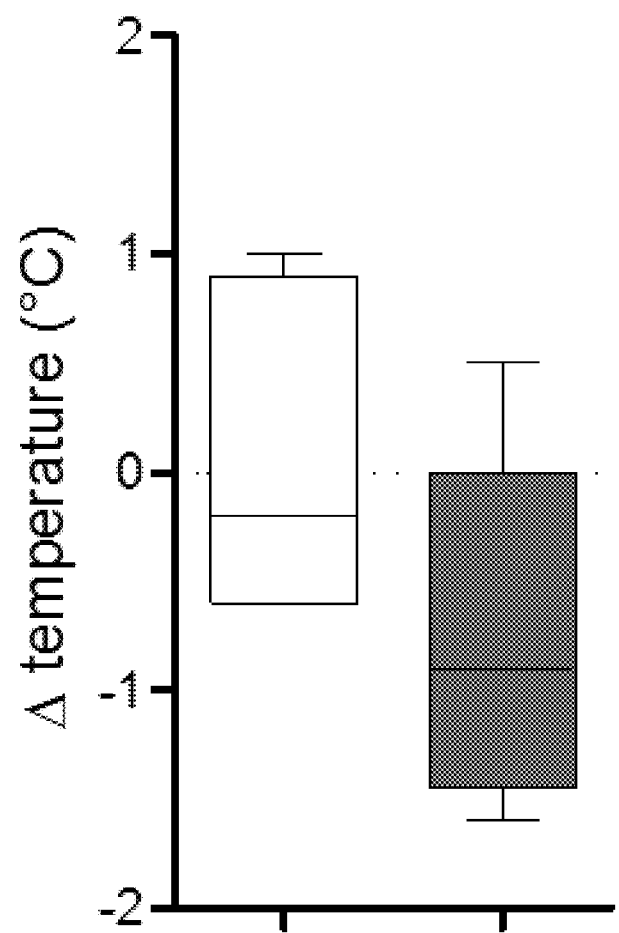
FIGS. 8A-8D. Oral administration of 50 mg/kg WOBE437 did not elicit all the effects in the cannabinoid tetrad test in BALB/c male.
Figure 8B:
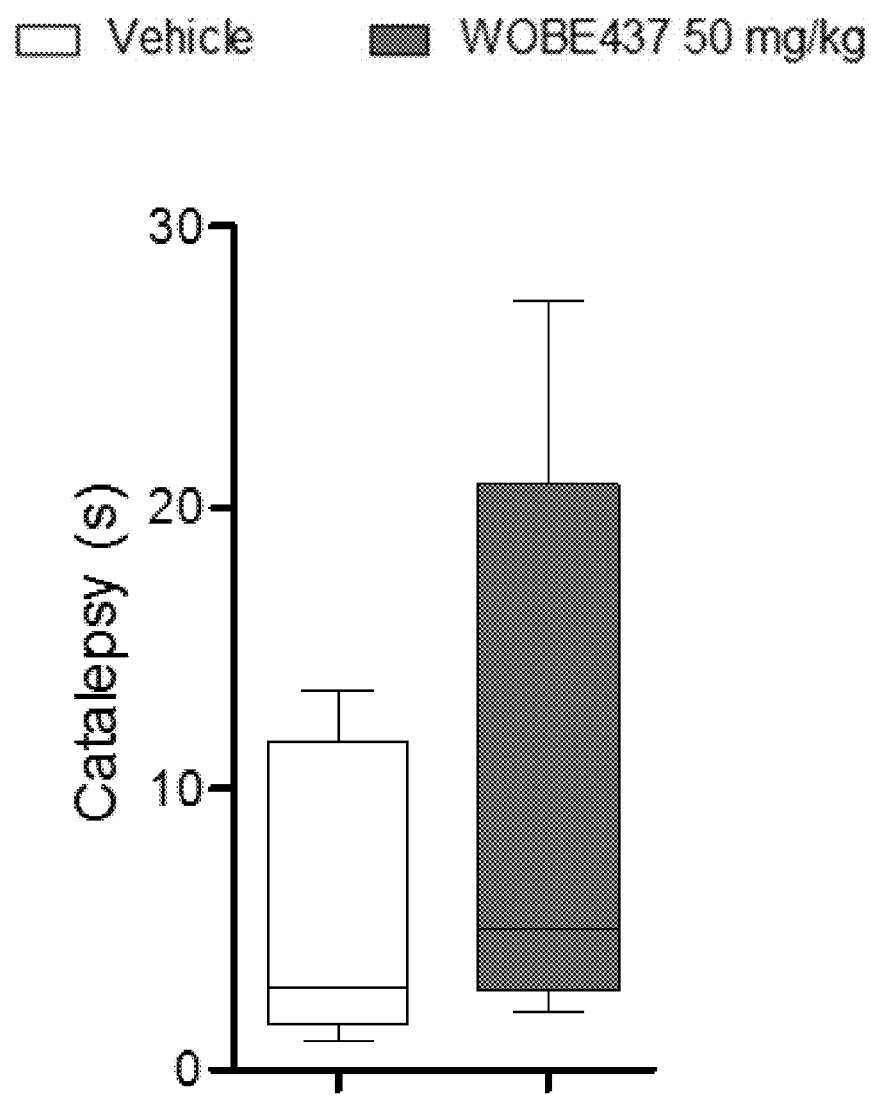
Figure 8C:
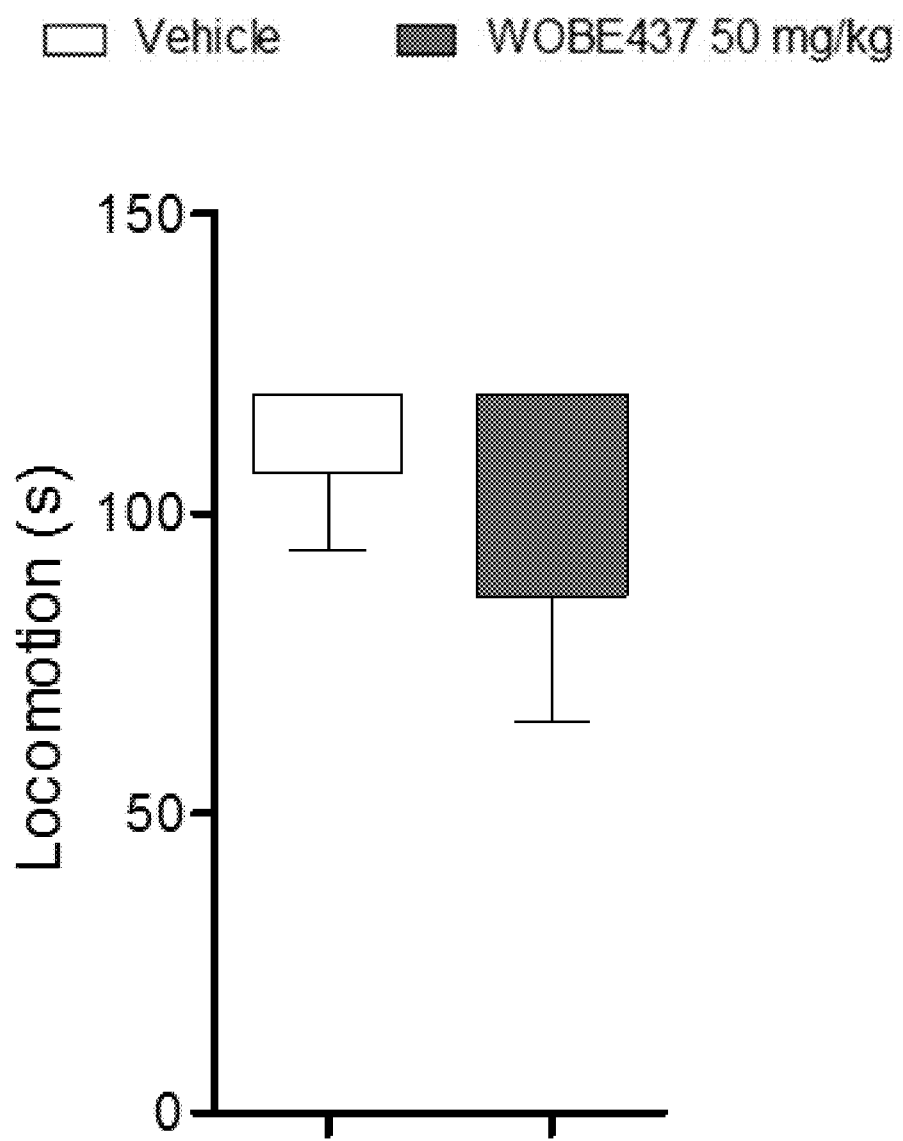
Figure 8D:
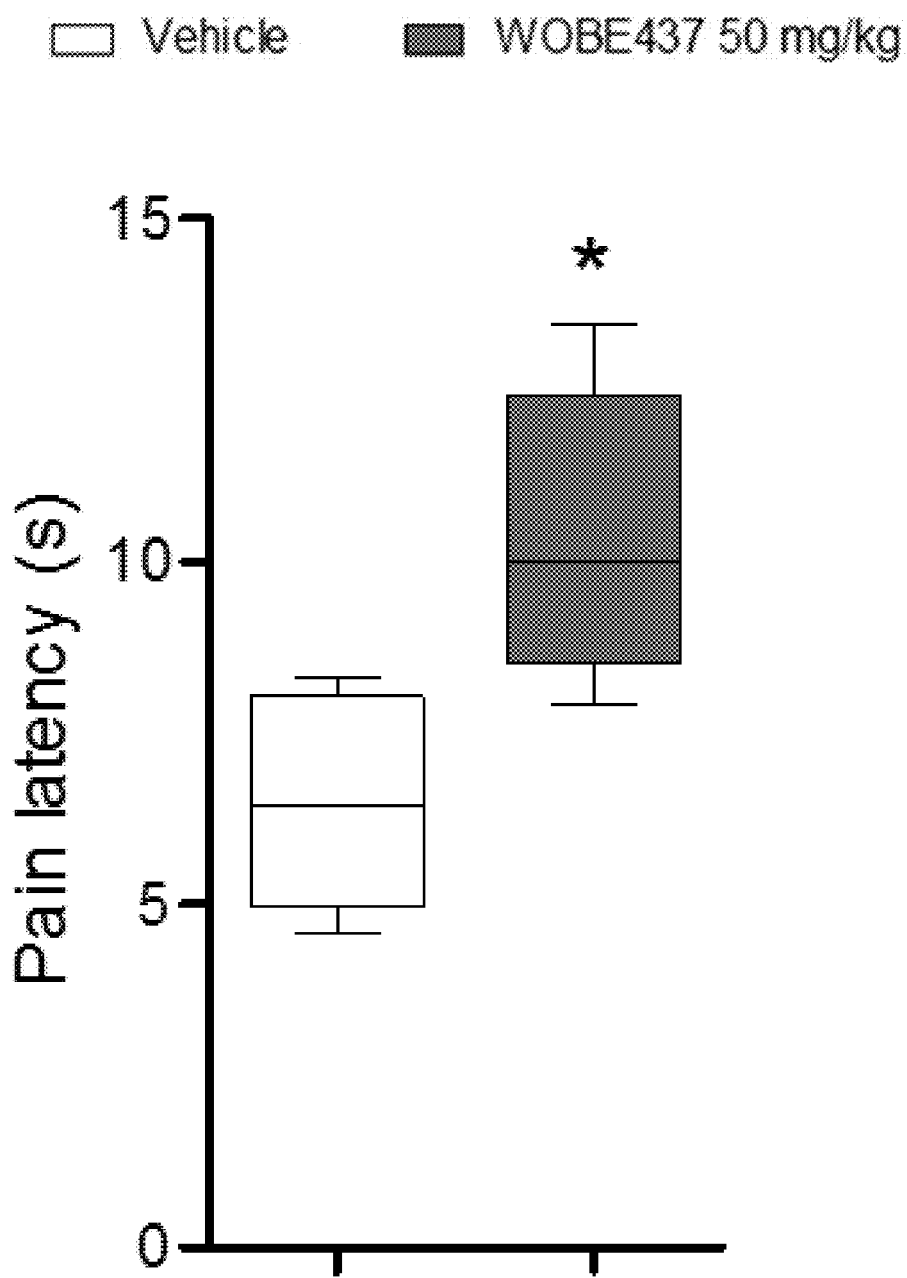
Figure 9A:
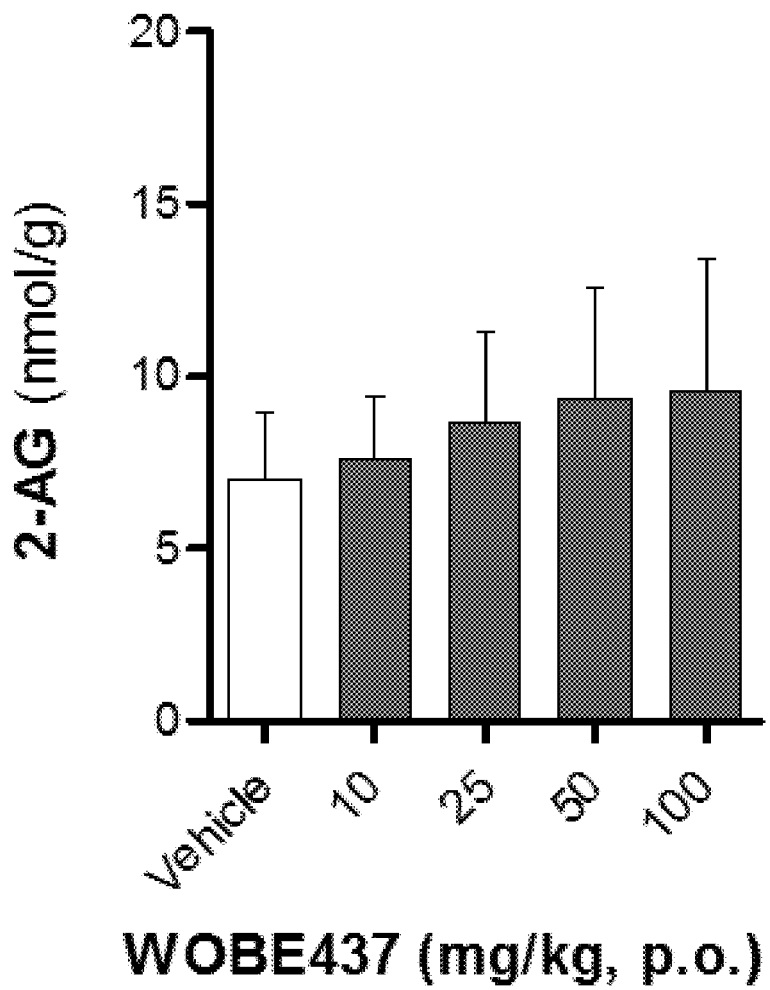
FIGS. 9A-9I. Changes in endocannabinoid levels 1 h after oral administration of WOBE437 in BALB/c male mice.
Figure 9B:
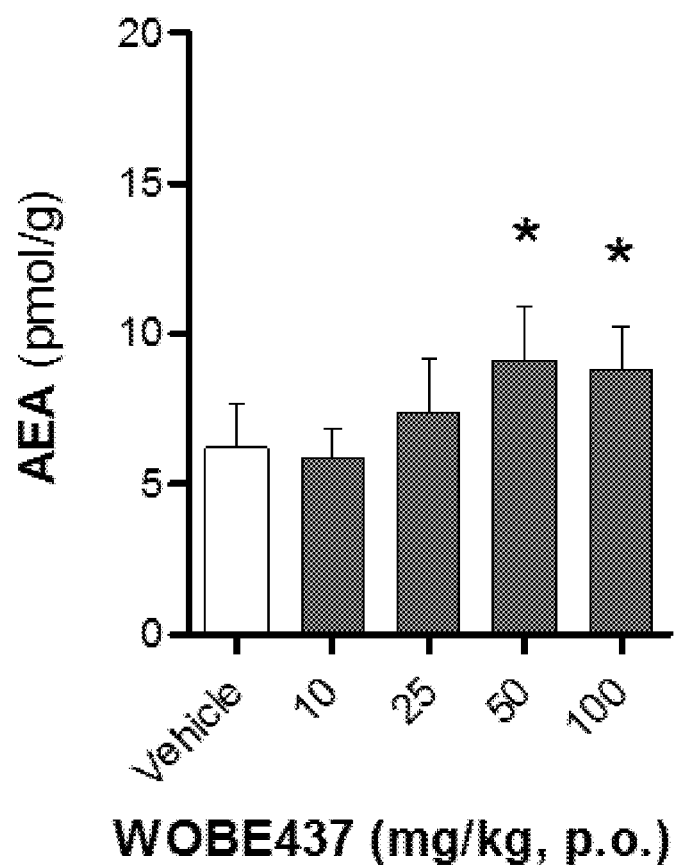
Figure 9C:
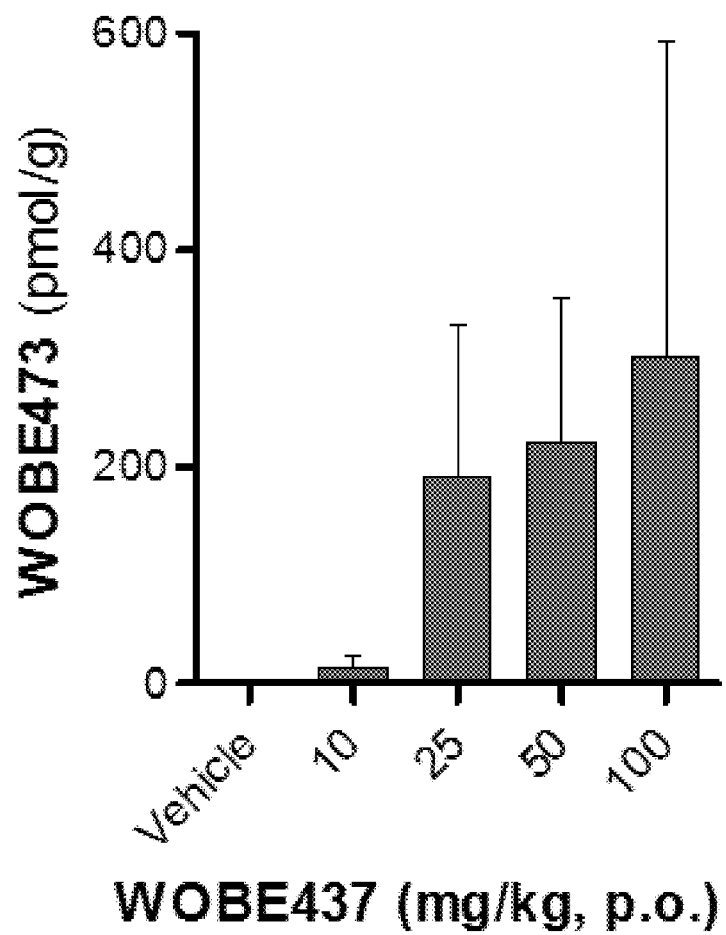
Figure 9D:
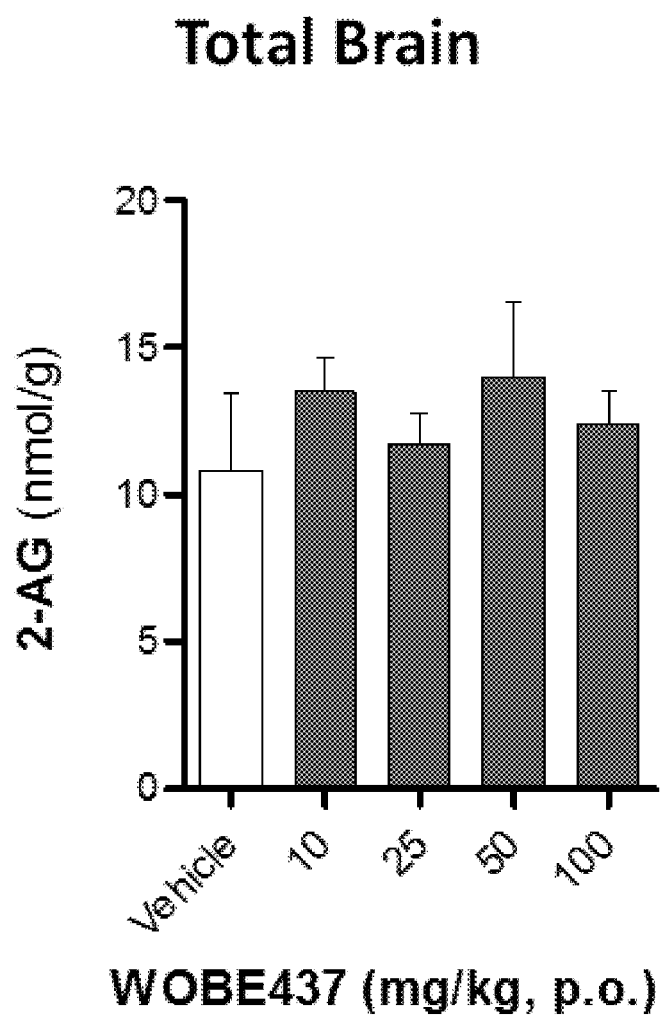
Figure 9E:
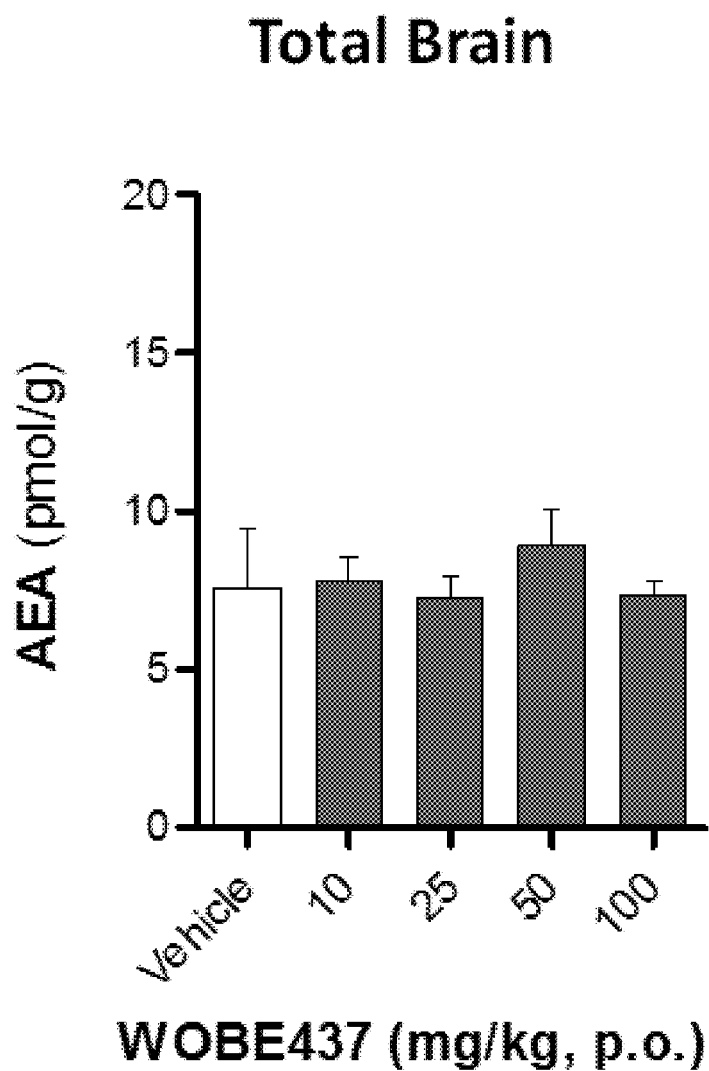
Figure 9F:
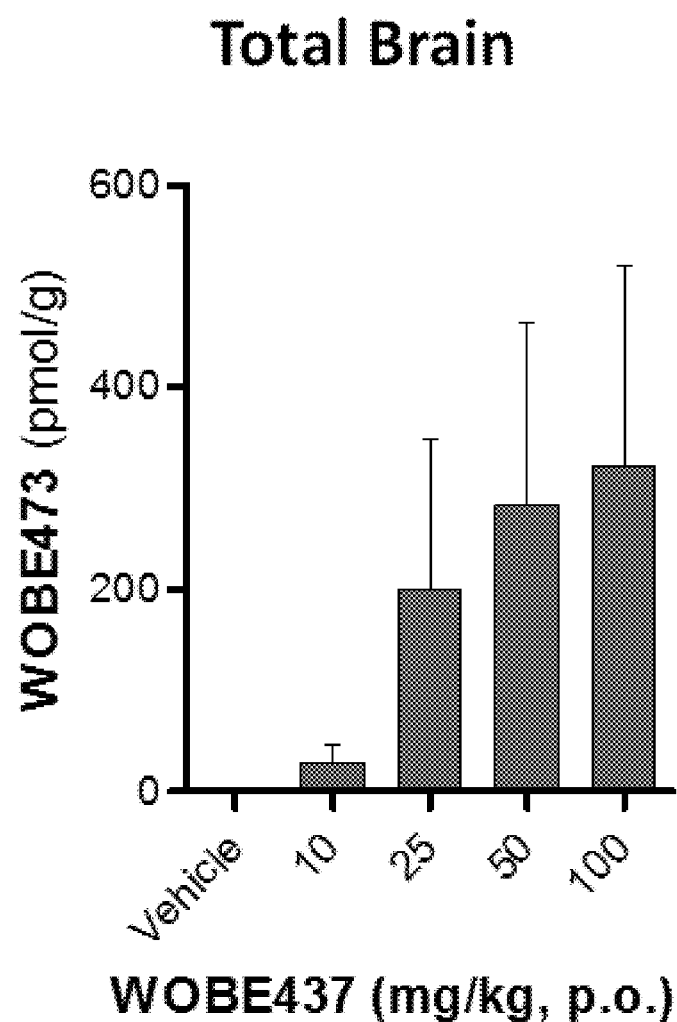
Figure 9G:
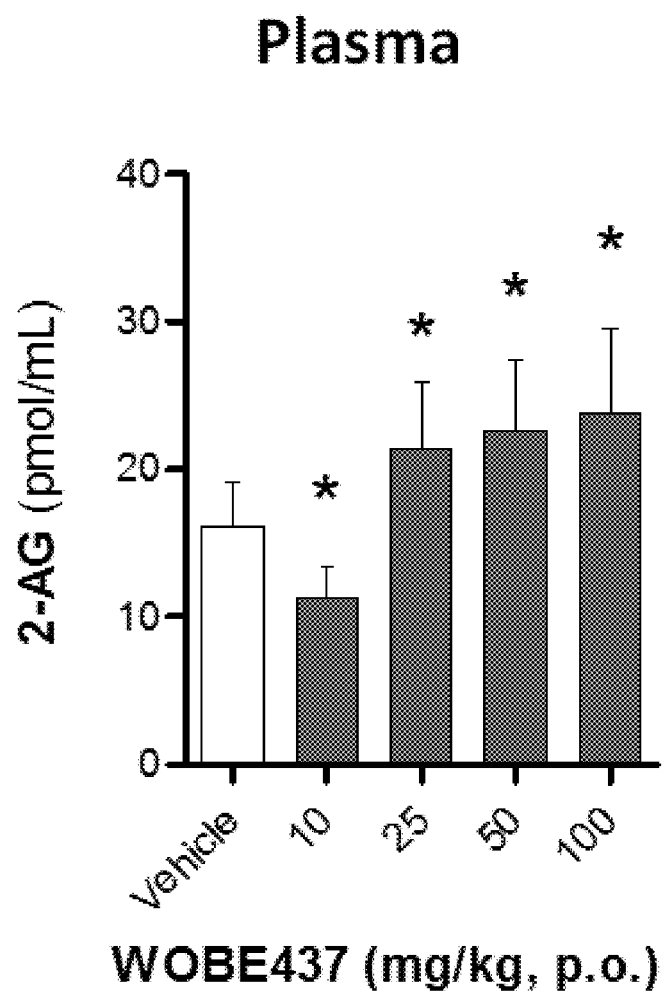
Figure 9H:
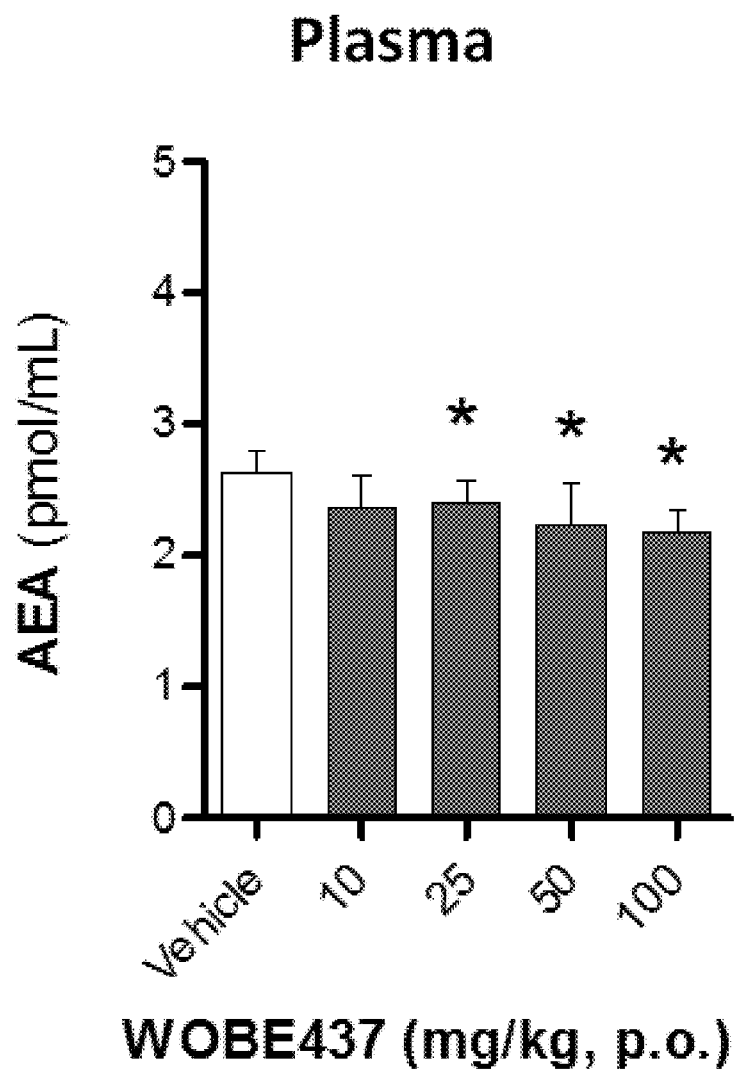
Figure 9I:
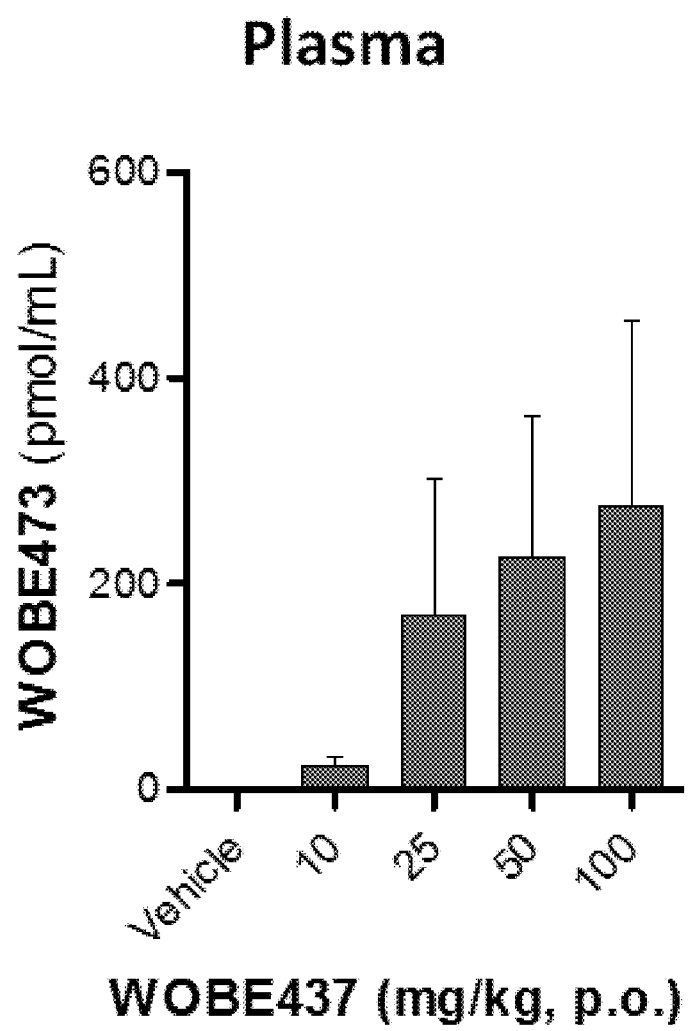
Figure 10A:
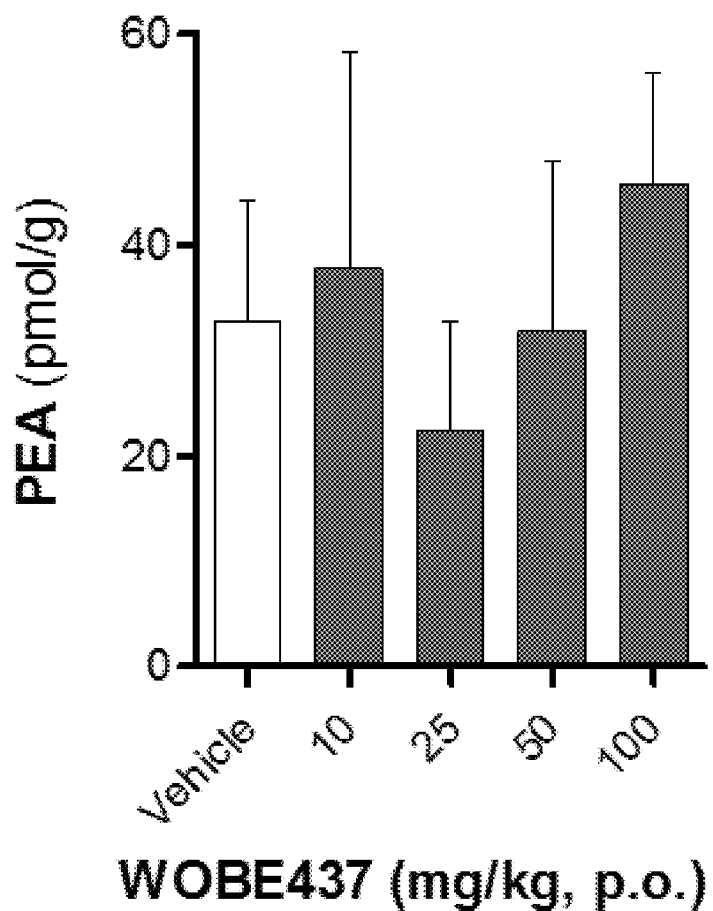
FIGS. 10A-10I. Levels of N-acylethanolamines 1 h after oral administration of WOBE437 in BALB/c male mice.
Figure 10B:
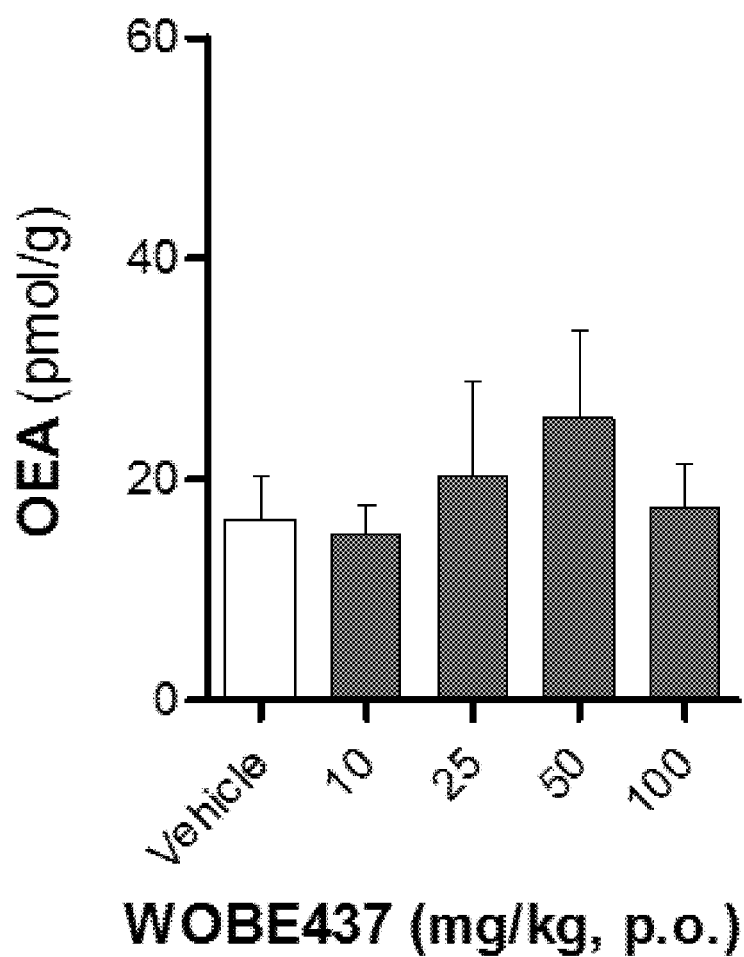
Figure 10C:
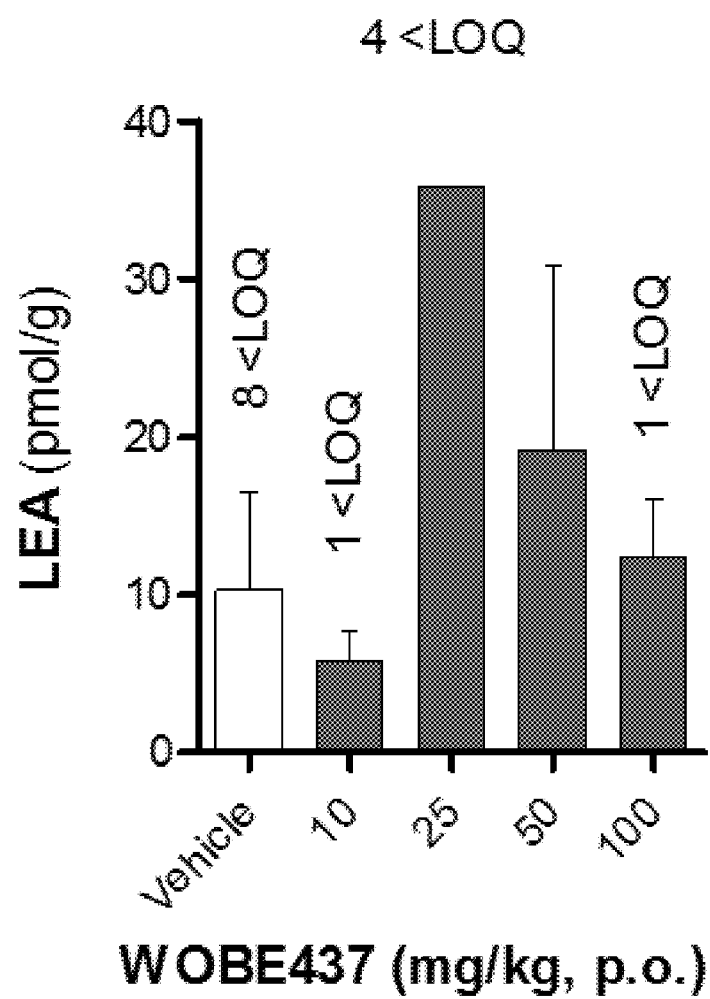
Figure 10D:
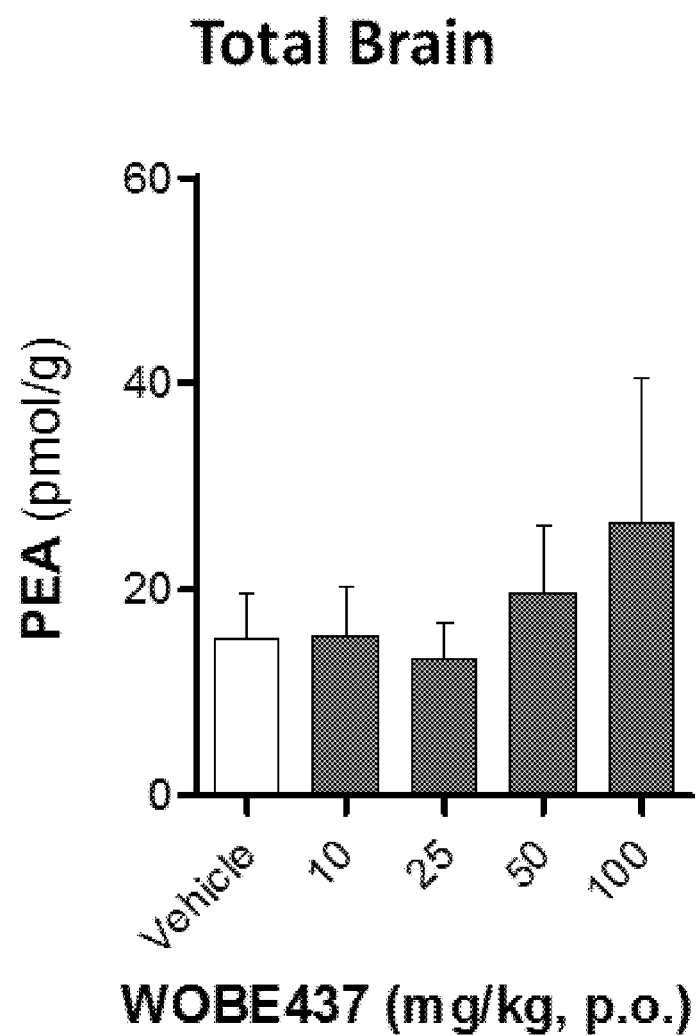
Figure 10E:
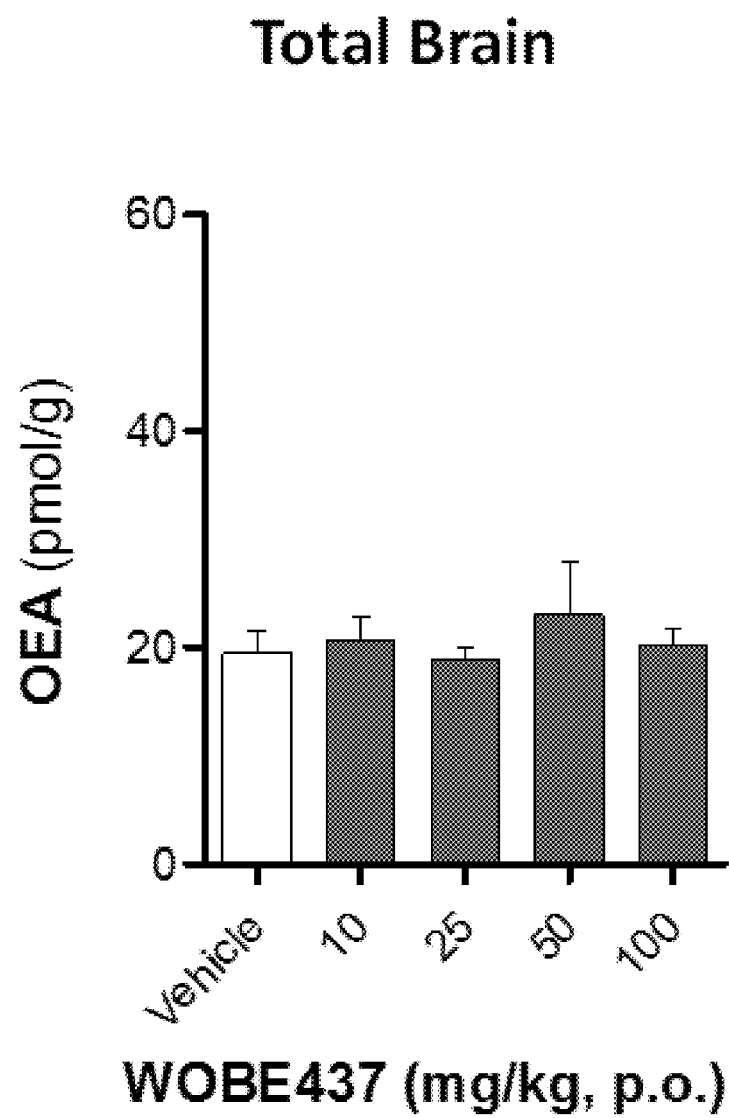
Figure 10F:
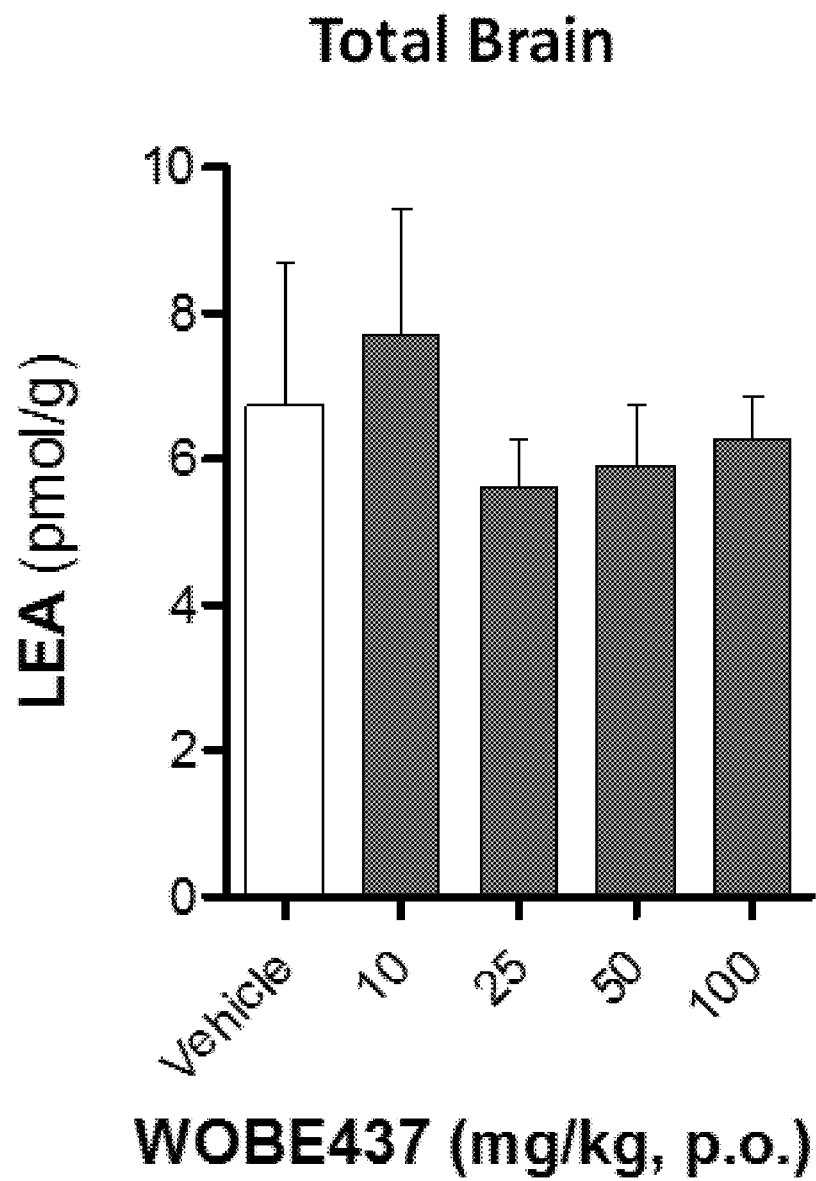
Figure 10G:
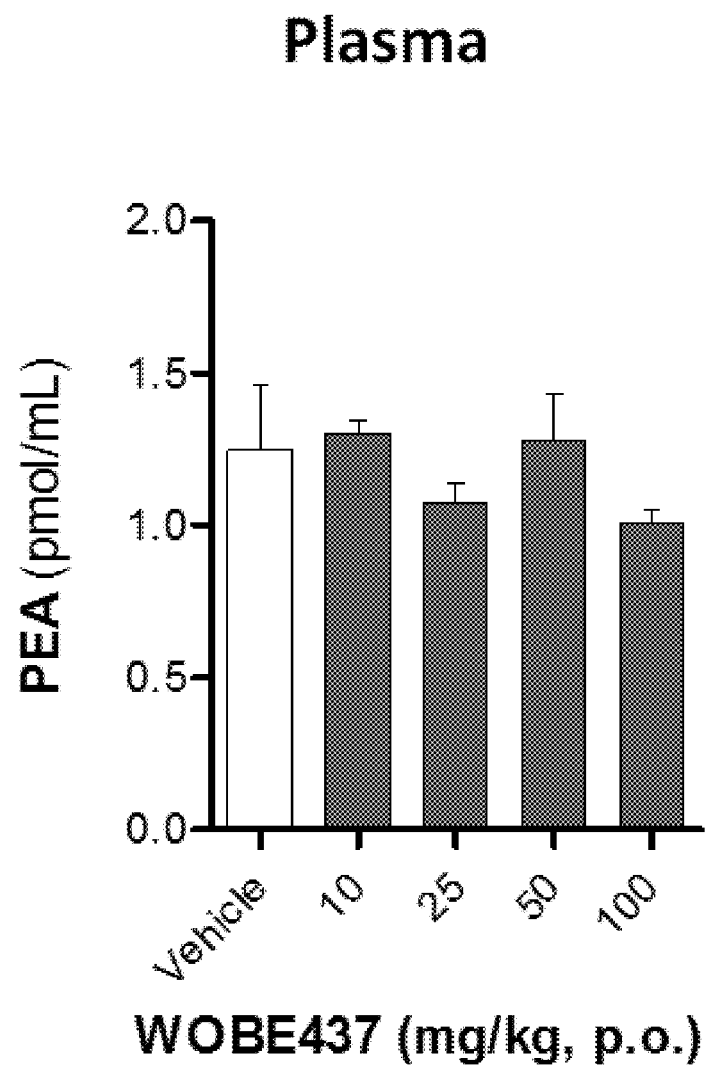
Figure 10H:
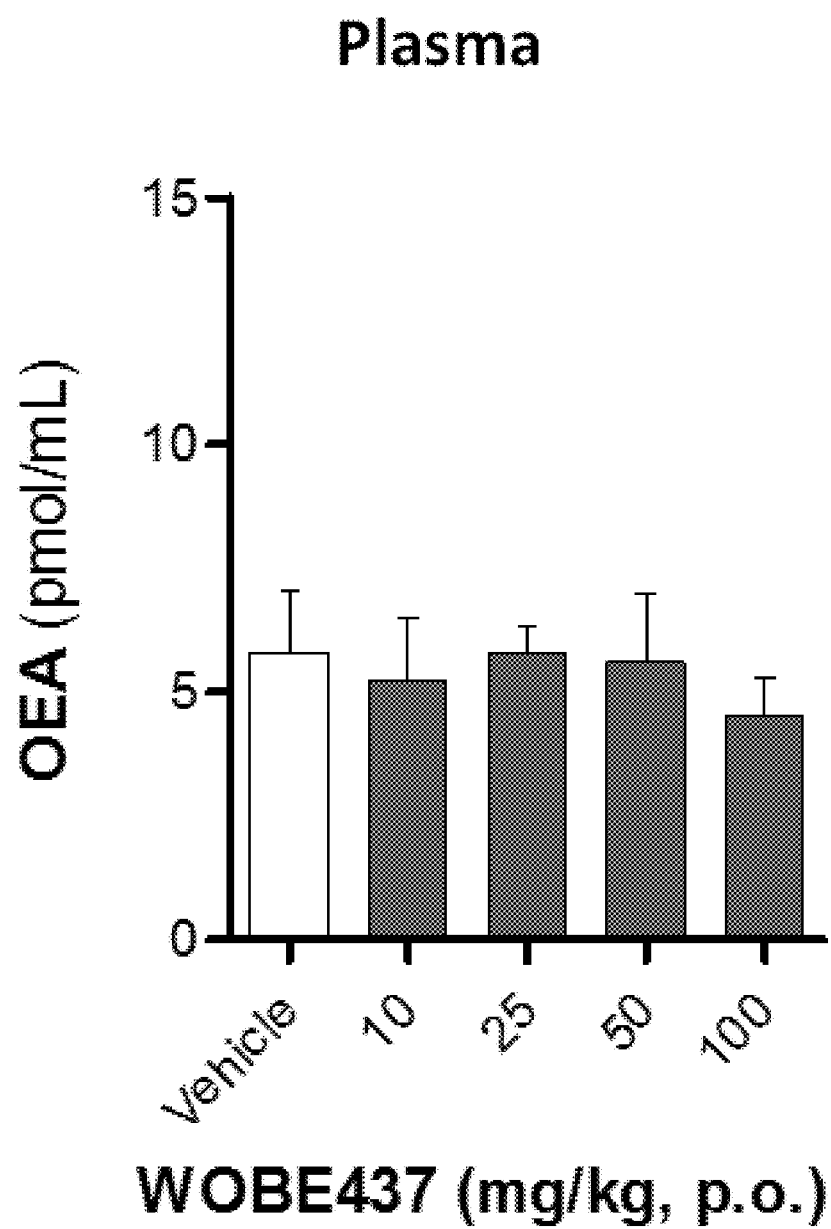
Figure 10I:
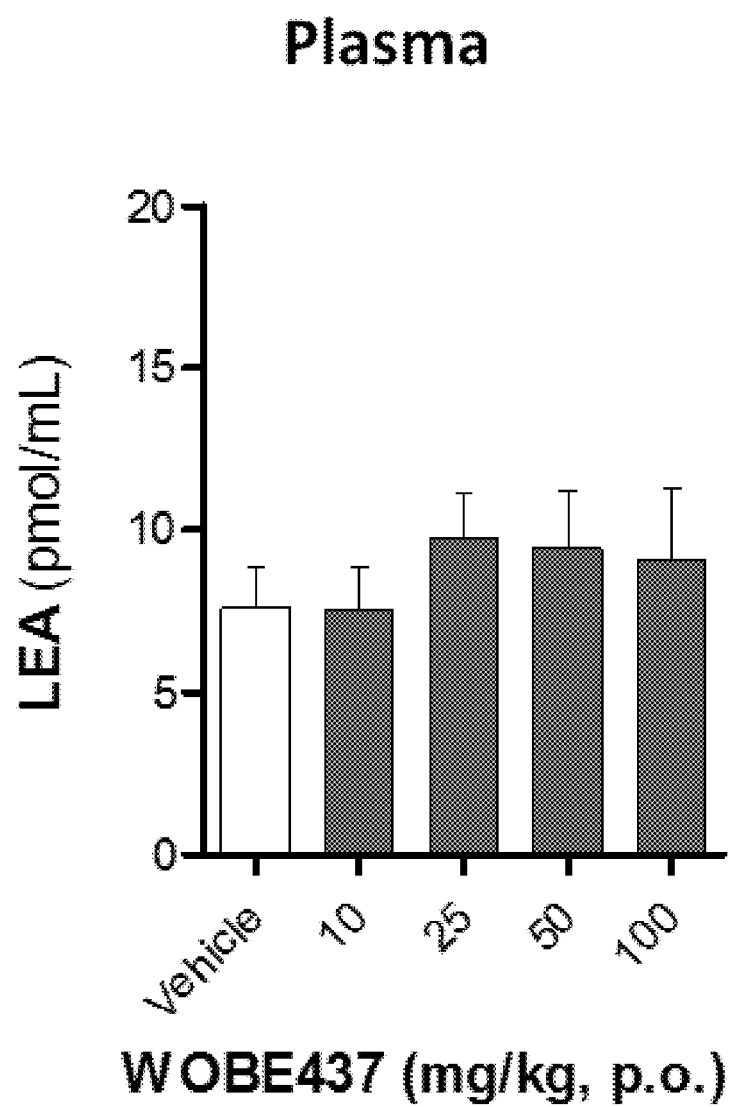

Since WOBE437 has previously shown analgesic effects in different models of acute pain after single i.p. injection (Chicca et al., 2017), we evaluated the pharmacological effects of WOBE437 after oral administration in BALB/c male mice. In a dose-response curve, 50 mg/kg p.o. of WOBE437 was the minimum dose necessary to significantly increase the pain threshold from 5.8±0.9 s in the vehicle group to 9.4±1.9 s (61.7% increase, FIG. 7A). WOBE437 at 100 mg/kg p.o. marginally further increased the pain threshold to 11.7±2.6 s, thus not significantly more than 50 mg/kg, with an estimated effective dose (ED50) value of 42.5±3.9 mg/kg. The analgesic effect of WOBE437 was mediated through the CB1 receptor as the antinociceptive effect was completely abolished after rimonabant pre-treatment (FIGS. 7B and 7C). Additionally, the oral administration of 50 mg/kg of WOBE437 was evaluated in the tetrad test (FIG. 8). No statistical differences were found in body temperature, catalepsy or motor coordination, but significant antinociception was measured. However, a tendency to induce hypothermia (FIG. 9A) and catalepsy (FIG. 9B) was observed as the body temperature decreased from +0.1±0.8° C. (control) to −0.8±0.8° C. (WOBE437 50 mg/kg) and the latency of catalepsy increased from 5.9±5.4 s (control) to 10.5±10.6 s (WOBE437 50 mg/kg). To further characterize the effects of oral administration of WOBE437, brain and plasma samples were collected after the hot plate test to analyze the EC levels. In somatosensory cortex, 50 mg/kg of WOBE437 showed a significant increase in AEA levels (FIG. 9B) but no changes in 2-AG (FIG. 9A). In total brain, WOBE437 showed a tendency to increase both AEA and 2-AG levels (FIGS. 9D and 9E). Interestingly, in plasma we measured a dose-dependent biphasic effect on 2-AG with a significant rise in 2-AG levels after 50 and 100 mg/kg of WOBE437 (FIG. 9G). AEA showed a statistically significant but slight reduction in plasma (FIG. 9H). The levels of WOBE437 were similar in somatosensory cortex, total brain and plasma (FIGS. 9C, 9F, and 9I) and in the same range as in male C57BL6/J mice (FIG. 5B), despite BALB/c showing a tendency towards lower plasma levels (not statistically significant). Overall, the oral administration resulted in high variability of WOBE437 tissue concentrations. No changes in the levels of N-acylethanolamines other than AEA were measured in the somatosensory cortex, total brain or plasma (FIG. 10).

Figure 11A:
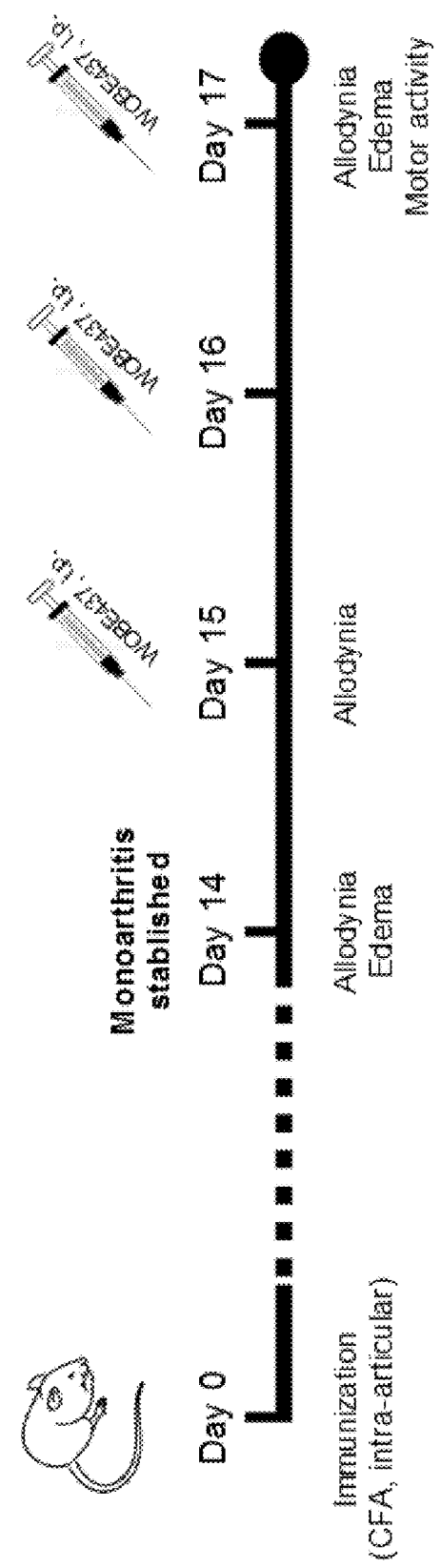
FIGS. 11A-11E. Effect of WOBE437 on allodynia and inflammation after a single dose or 3 days treatment in a mouse model of monoarthritis.
Figure 11B:
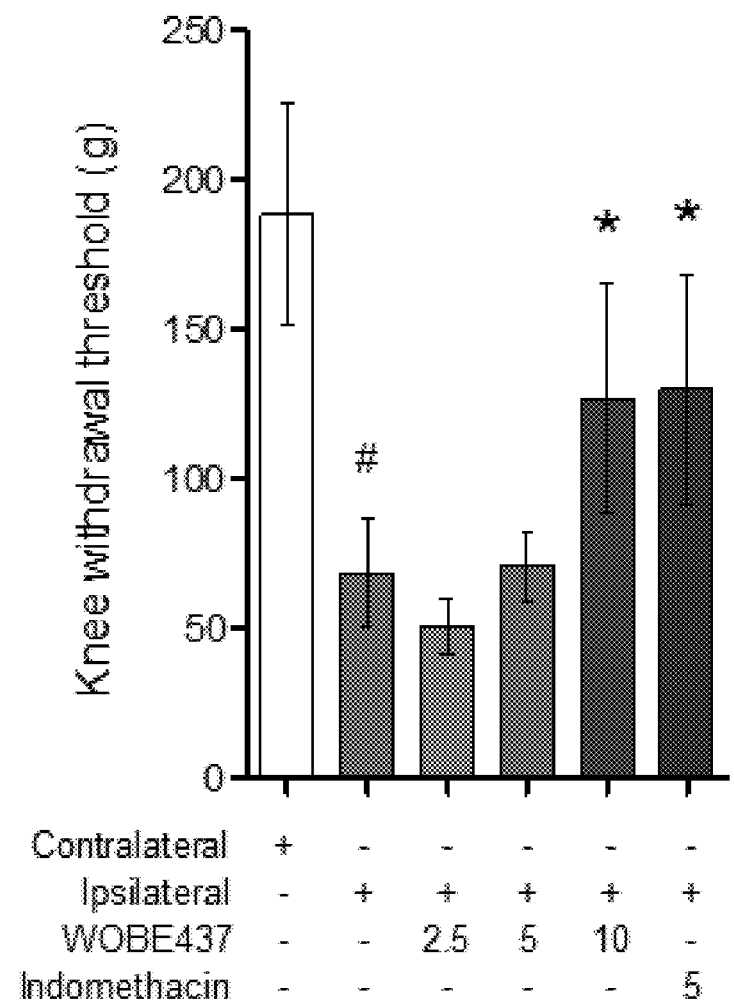
Figure 11C:
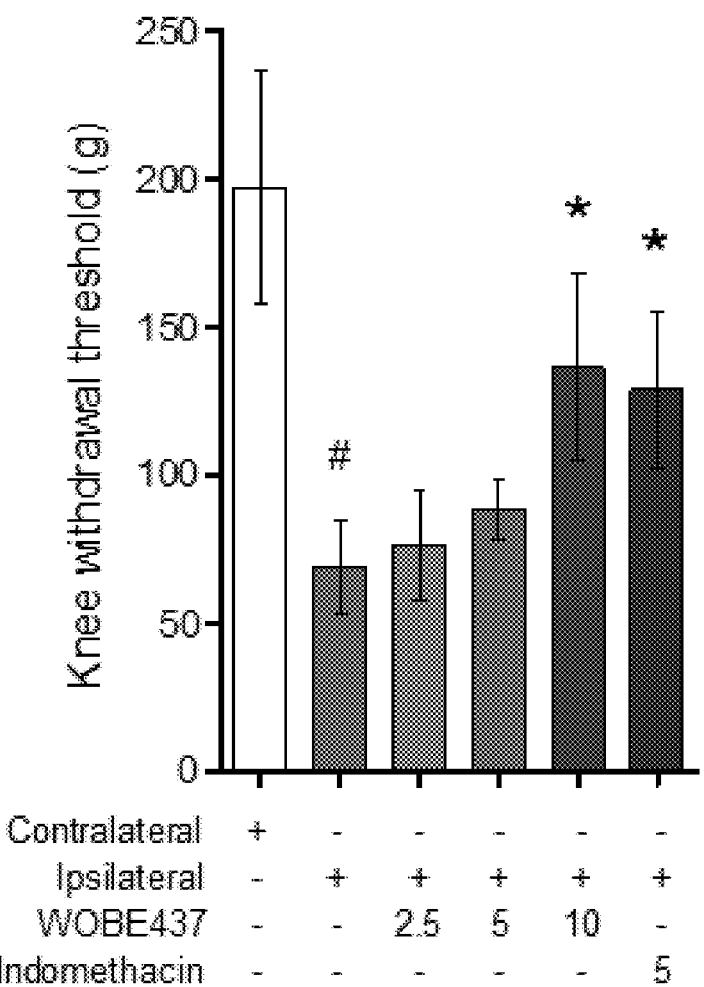
Figure 11D:
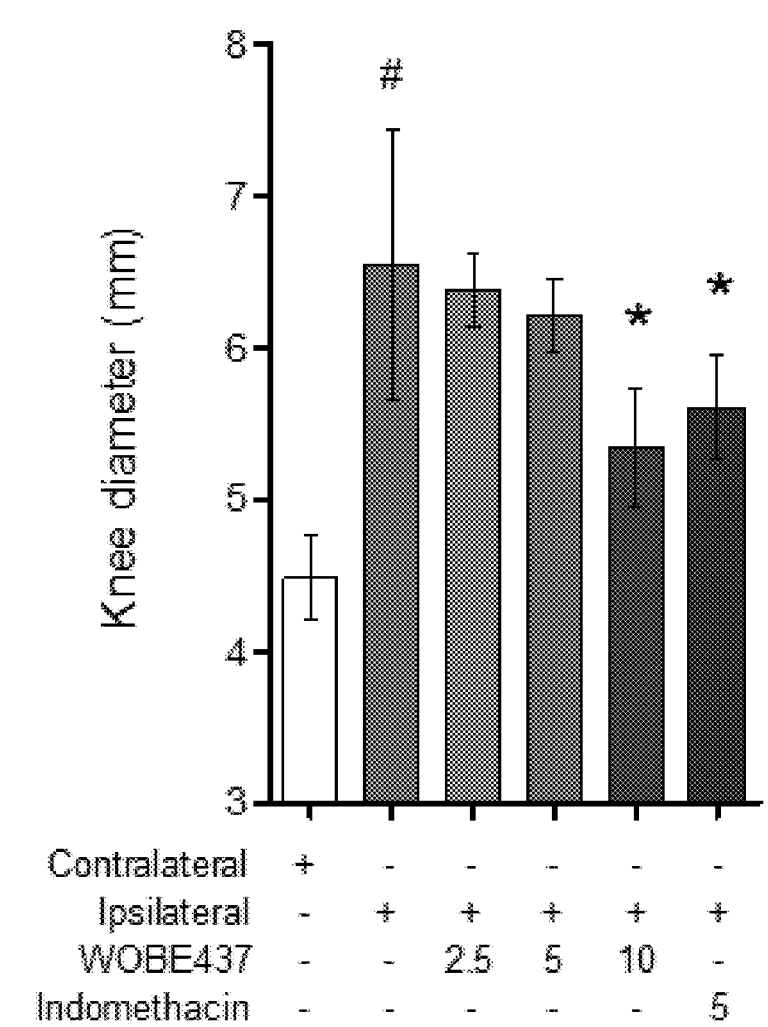
Figure 11E:
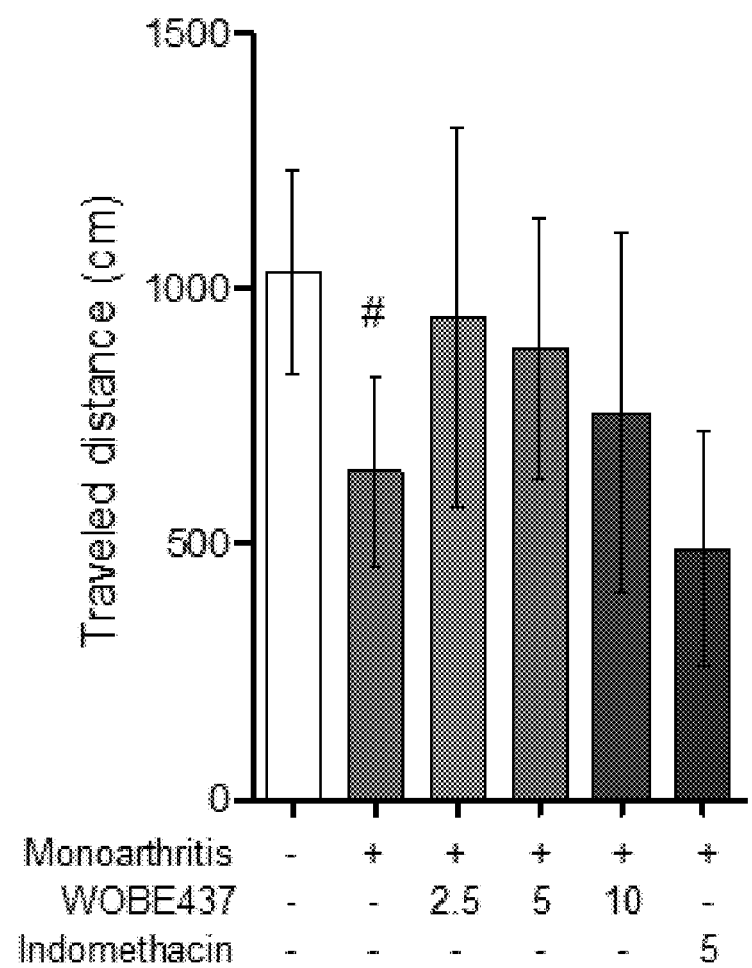

WOBE437 Indirectly Triggers Polypharmacological Effects in a Model of Chronic Inflammation Considering our previous data showing the analgesic and antiinflammatory effects of WOBE437 after single i.p. injection (Chicca et al., 2017) and the confirmation of CB1 receptor-dependent antinociception after oral WOBE437 administration (FIG. 7), we decided to further evaluate its pharmacological properties and underlying mechanism(s) in a chronic model of inflammatory pain. After the induction of monoarthritis by intra-articular injection of CFA in mice (FIG. 11A), a single dose of WOBE437 at 10 mg/kg i.p. was able to significantly decrease allodynia (FIG. 11B). After 3 days treatment, allodynia was reduced by increasing the pain threshold from 69.0±15.7 g in the vehicle group to 136.3±31.7 g in the group treated with WOBE437 10 mg/kg i.p., reflecting a reduction of 52% in allodynia as compared to the contralateral knee (197.0±39.6 g) (FIG. 11C). Furthermore, the inflammation (edema) was reduced by 58% resulting in a decrease of the knee diameter from 6.5±0.9 mm in the vehicle group to 5.3±0.4 mm in the WOBE437 10 mg/kg group as compared to the contralateral knee (4.5±0.3 mm) (FIG. 11D). The doses of 2.5 and 5.0 mg/kg i.p. did not show any significant changes. The spontaneous motor activity was measured, but without significant observable changes upon WOBE437 treatment. Nevertheless, a noteworthy tendency to improve spontaneous locomotion was noticed in the monoarthritic group treated with WOBE437 2.5 mg/kg (FIG. 11E).

Figure 12A:
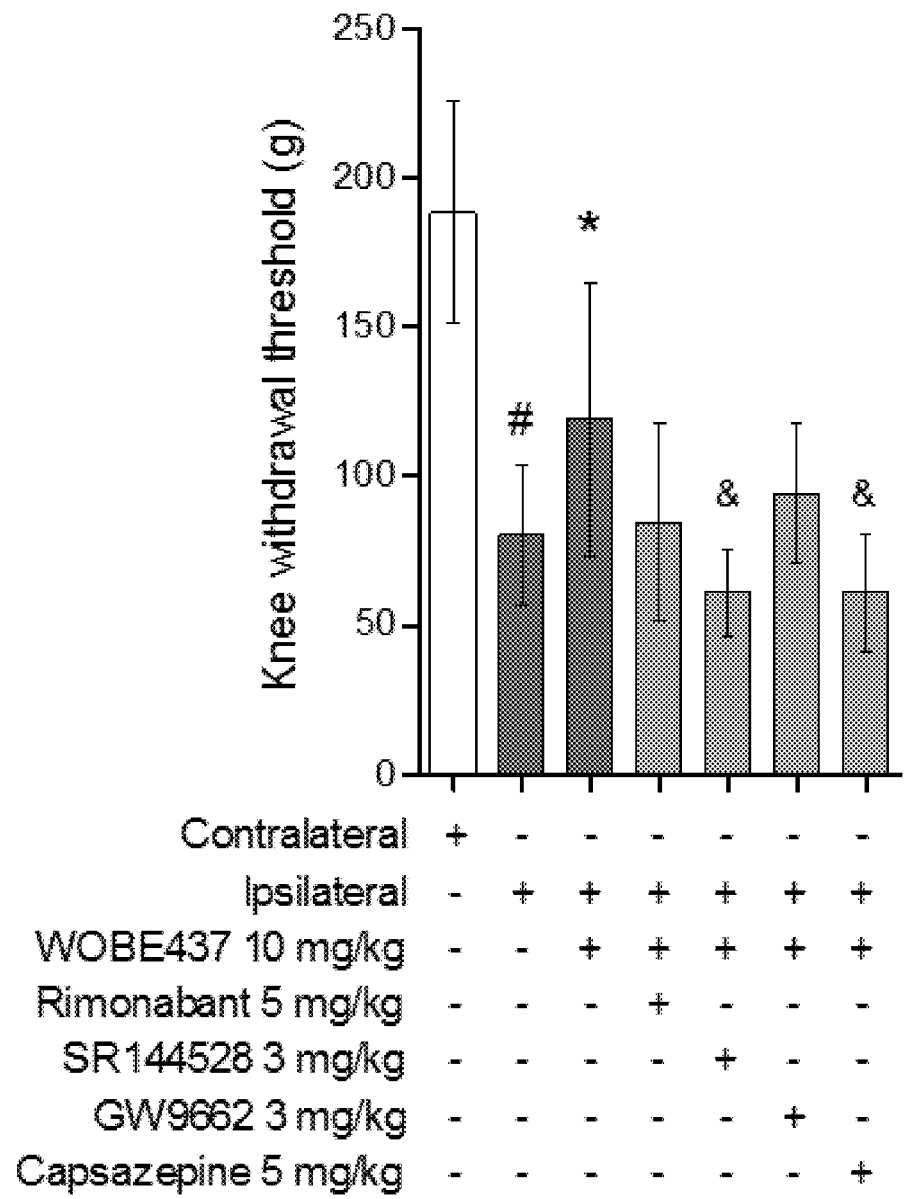
FIGS. 12A-12C. Polypharmacological effects observed upon 3 days treatment with 10 mg/kg of WOBE437
Figure 12B:
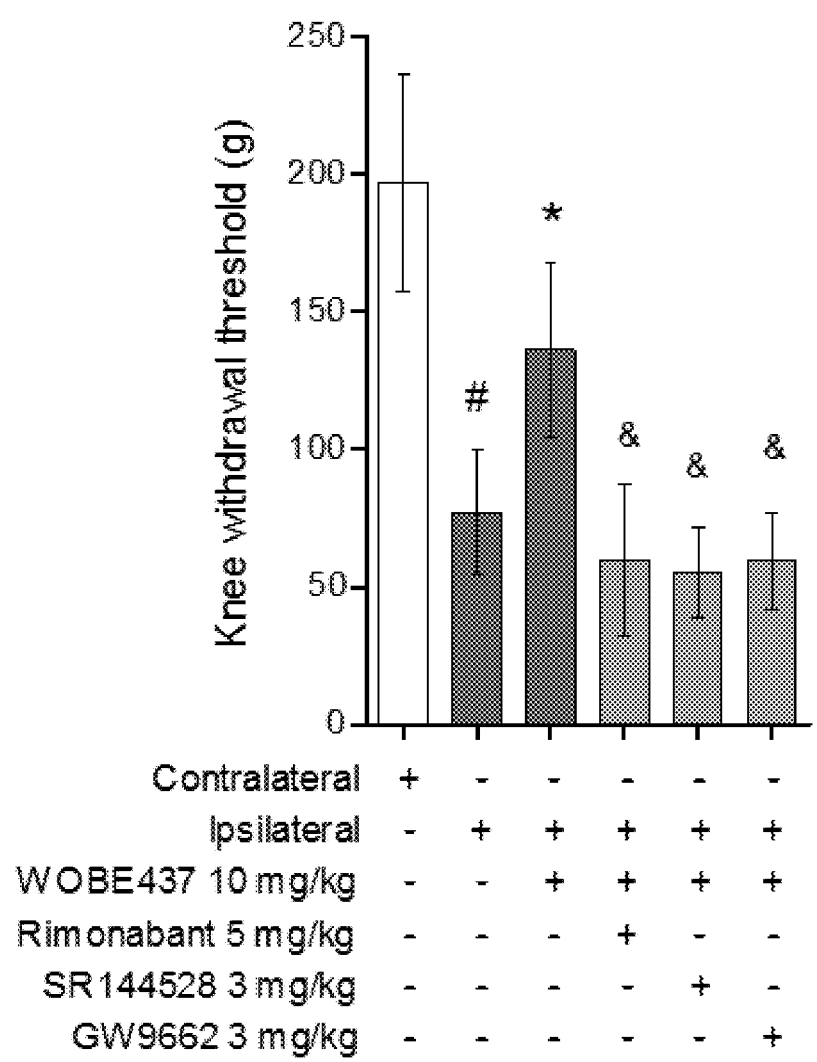
Figure 12C:
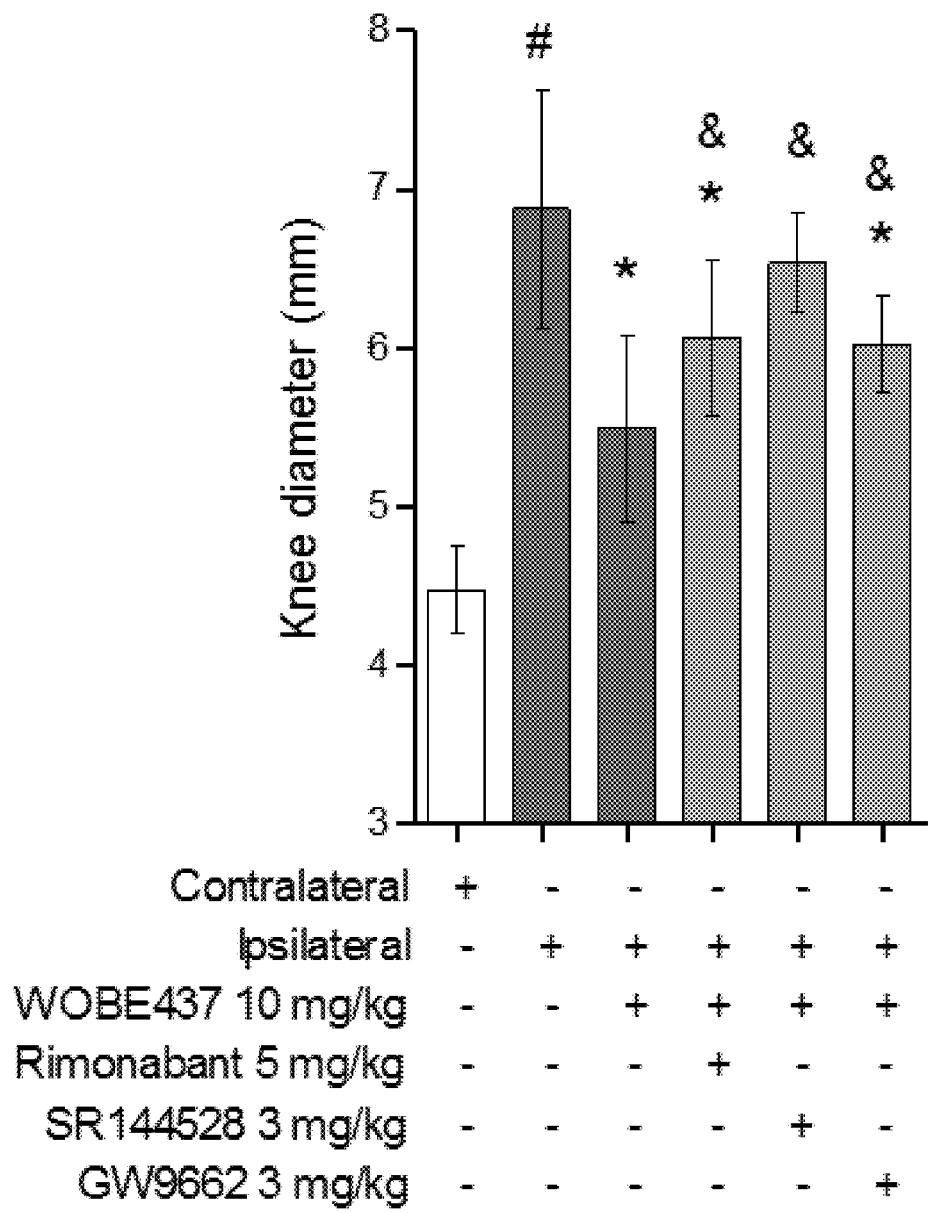
Figure 13A:
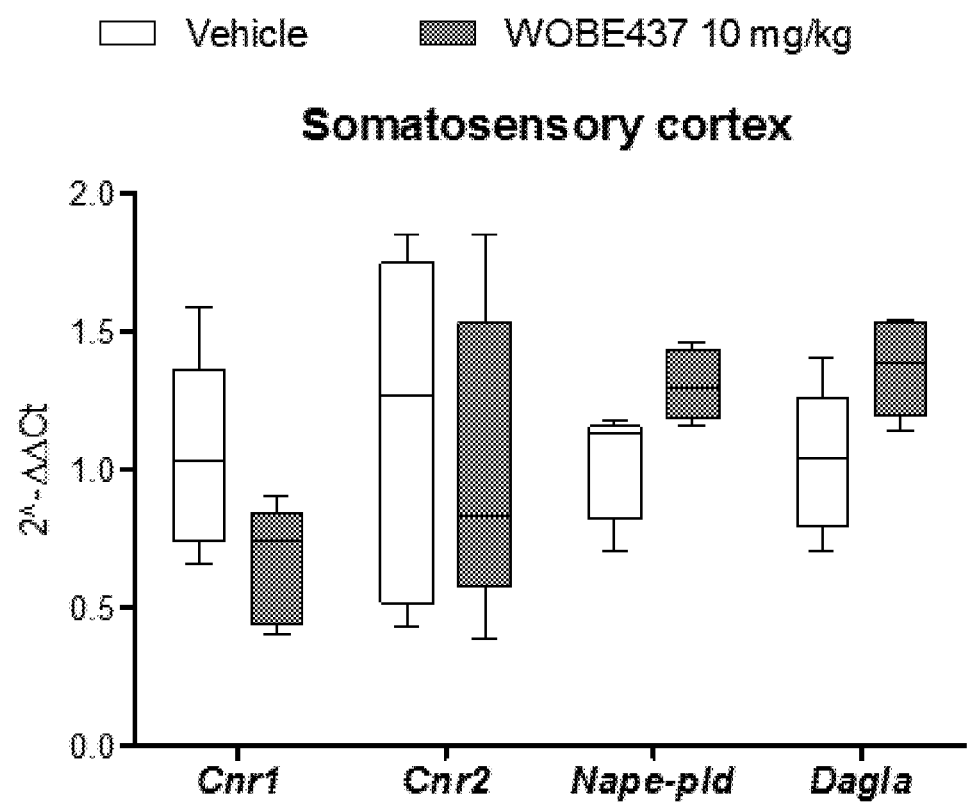
FIGS. 13A-13C. Changes in total RNA levels of EC components after the CFA-induced monoarthritis model and 3 days treatment with WOBE437 10 mg/kg i.p. in BALB/c mice.
Figure 13B:
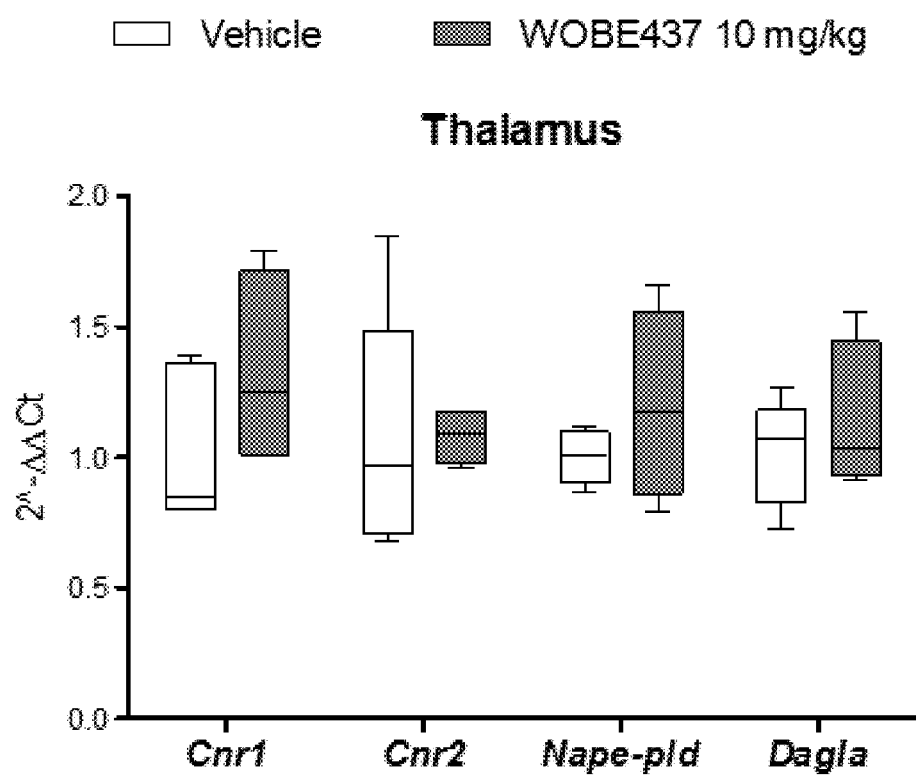
Figure 13C:
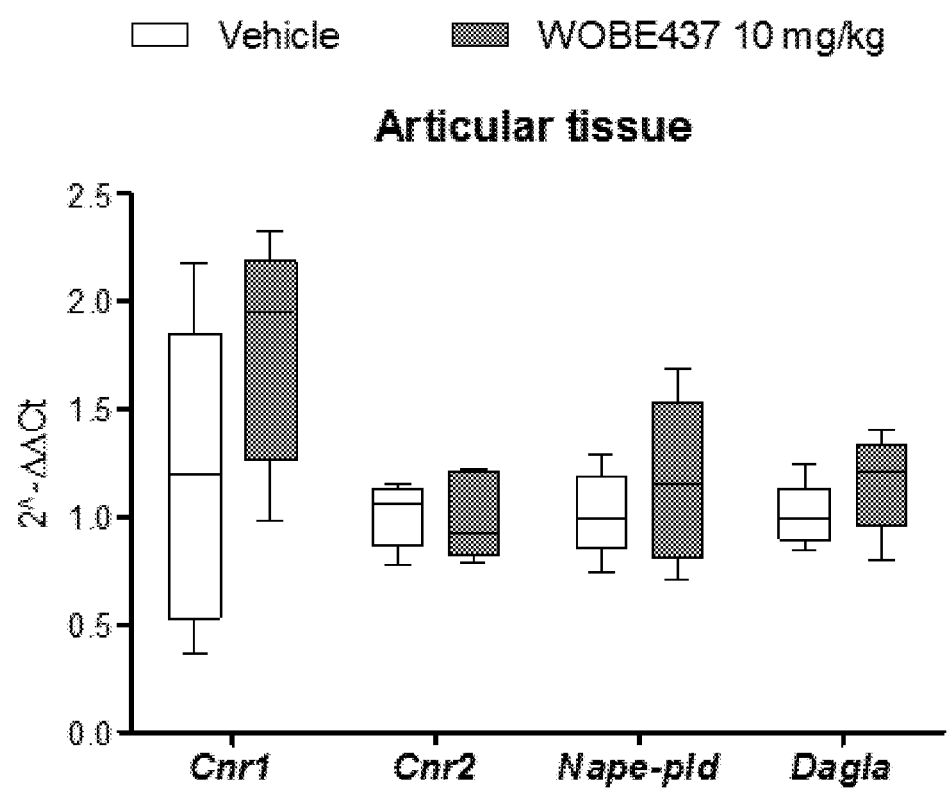

In an attempt to better characterize the downstream mechanism(s) involved in the pharmacological effects mediated by WOBE437 in the monoarthritis model, we pre-treated the mice with cannabinoid CB1 receptor, cannabinoid CB2 receptor, PPARγ and TRPV1 antagonists. In the single dose experiment, the antiallodynia effects of WOBE437 (10 mg/kg i.p.) were clearly mediated by cannabinoid CB2 and TRPV1 receptors because the CB2 receptor antagonist/inverse agonist SR144528 (3 mg/kg, i.p.) and the TRPV1 antagonist capsazepine (5 mg/kg, i.p.) completely prevented the improvement in mechanical sensitivity by WOBE437 (FIG. 7A). Conversely, the CB1 antagonist/inverse agonist rimonabant and PPARγ antagonist GW9662 did not block the effect of WOBE437 in this experiment. Interestingly, a clear multi-target mechanism was seen after 3 days treatment with WOBE437 10 mg/kg i.p. because the antiallodynia and antiinflammatory effects were fully abolished by each of the cannabinoid CB1 receptor antagonist/inverse agonist rimonabant (5 mg/kg, i.p.), the CB2 antagonist SR144528 (3 mg/kg, i.p.) and PPARγ antagonist GW9662 (3 mg/kg, i.p.) (FIGS. 12B and 12C). On the other hand, the antiinflammatory effect was only partially prevented with rimonabant and GW9662 (FIG. 12C), indicating additive contributions of CB1 and PPARγ receptors, respectively. In the 3 days WOBE437 treatment we could not use the TRPV1 antagonist capsazepine because the mice showed an unexpected hypersensitivity. In the monoarthritic mice, WOBE437 treatment did not lead to any significant change in the expression of the cannabinoid CB1 receptor (Cnr1), the cannabinoid CB2 receptor (Cnr2) or the enzymes involved in EC production, namely diacylglycerol lipase (Dagla) and N-acylphosphatidylethanolamine specific phospholipase D (Nape-pld) (FIG. 13), thus excluding broad transcriptional effects on the ECS.

Discussion

WOBE437 is Orally Bioavailable to the Brain and Exerts Cannabinoid CB1 Receptor-Dependent Antinociceptive Effects As outlined by Arrowsmith et al., chemical probes are powerful tools with increasing impact on biomedical research. However, probes and inhibitors of poor quality or that are used incorrectly generate misleading results (Arrowsmith et al., 2015). Among the AEA transport inhibitors, this problem is inherent because they do not generally fulfil the criteria of a good chemical probe, such as potency, selectivity and bioavailability. Importantly, none of the AEA/EC transporter inhibitors (UCM707, OMDM-2, AM404, guineensine) has been investigated for general bioavailability, pharmacokinetic parameters or brain penetration by analytical methods (see below). WOBE437 is a novel highly potent and selective EC reuptake inhibitor (SERI) which specifically increases/modulates the levels of the two main ECs AEA and 2-AG in vitro and in vivo (Chicca et al., 2017). WOBE437 showed relevant pharmacological effects in different animal models of acute pain, anxiety and endotoxemia, reaching bioactive concentrations in the brain after intraperitoneal injection (Chicca et al., 2017). Here, we assessed the basic oral bioavailability of WOBE437, its distribution to the brain, plasma and peripheral tissues and evaluated its corresponding antinociceptive and cannabimimetic effects. Considering the stress induced by gavage feeding, the hot plate assay was an ideal nociception paradigm as it avoids chronic stress, unlike e.g. chronic inflammation. Our results showed quantifiable levels of WOBE437 in brain already 10 min after oral gavage, reaching the highest concentration 20 min after administration, with an estimated $t_{max}$ of ≤20 min in plasma ($C_{max}$~2000 pmol/mL after 50 mg/kg p.o.) and brain ($C_{max}$~500 pmol/g after 50 mg/kg p.o.). The WOBE437 concentration in brain remained relatively stable between 300 and 400 pmol/g up to 1 h and was still detectable 3 h after administration (18 pmol/g). A control over the bioavailability and basic pharmacokinetics requirements (e.g. reaching bioactive tissue concentrations) are fundamental to understand the pharmacological effects measured in behavioral tests. However, the oral bioavailability of the currently used non-selective AEA transport inhibitors remains unknown. We and others have previously shown that AEA uptake inhibitors like UCM707, AM404 and VDM11 are substrates for h/rFAAH or hMAGL, which strongly suggest their metabolic instability, i.e. degradation after systemic administration (Chicca et al., 2017; Fegley et al., 2004; Vandevoorde and Fowler, 2005). Conversely, WOBE437 is not affected by the hydrolytic activity of FAAH and MAGL and is not modified by COX-2 (Chicca et al., 2017). Nevertheless, that the present data show that WOBE437 is significantly metabolized by liver microsomes (human and mouse) after 2 h of incubation, resulting in an estimated oral bioavailability of 4% (human) and 17% (mouse). In the hot plate test, WOBE437 exerted significant analgesic effects at the dose of 50 mg/kg upon oral administration, while the fully effective dose was 10 mg/kg upon systemic administration (i.p.) (Chicca et al., 2017). This difference suggests an overall 20% bioavailability compared to the i.p. administration route, in agreement the estimated maximal bioavailability of 17% calculated in mouse liver microsomes. According to these findings, one could assume that 50 mg/kg p.o. is almost equivalent to 10 mg/kg i.p (i.e., a factor of 5). However, the brain levels were approximately 10 times lower after p.o. as compared to i.p. Our previous findings showed that 10 mg/kg of WOBE437 i.p. induced a slight but significant effect in the entire tetrad test battery (hypothermia, catalepsy, hypolocomotion and analgesia) (Chicca et al., 2017). Therefore, we also tested the effects of 50 mg/kg of WOBE437 p.o. in BALB/c mice. However, statistical significance was only found for analgesia 1 h after oral administration of WOBE437 but only a tendency to induce hypothermia and catalepsy. This can be explained by the lower levels of WOBE437 in the brain.

One hour after oral administration of WOBE437 at the single dose of 50 mg/kg, a significant increase of AEA levels in the somatosensory cortex was measured, with only a tendency to increase AEA in the total brain. These findings point to a brain region-specific increment in the AEA levels, in agreement with the different EC levels across brain regions and changes in a tissue specific manner (Bystrowska et al., 2014; Chicca et al., 2017; Gonzalez et al., 2002). Moreover, 2-AG concentration showed a tendency to increase in total brain, from 10.8±2.6 nmol/g to 13.9±2.6 nmol/g after 50 mg/kg of WOBE437, without significant changes in somatosensory cortex. This lack of statistical significance in somatosensory cortex might be due to limited involvement of 2-AG in this area under basal conditions, because significant increase in 2-AG levels have been shown after stress or chronic constriction injury in dorsal midbrain and particularly in periaqueductal grey matter (PAG) (Hohmann et al., 2005; Petrosino et al., 2007). On the contrary, the treatment with 25, 50 and 100 mg/kg of WOBE437 induced a significant increase by 40% of 2-AG levels from 16.1±2.9 pmol/mL to 21.4±4.5 pmol/mL (25 mg/kg), 22.6±4.8 pmol/mL (50 mg/kg) and 23.8±5.7 pmol/mL (100 mg/kg) in plasma. On the other hand, the concentration of AEA in plasma was weakly but significantly reduced by 23%, from 2.6±0.2 pmol/mL in the control group to 2.2±0.3 pmol/mL in the group treated with WOBE437 at 50 mg/kg. This slight decrease in AEA levels may not cause biological effects but could rather reflect differential AEA transport kinetics between AEA and 2-AG in a complex tissue environment. We have previously shown that AEA and 2-AG compete for cellular uptake in vitro with different affinities (Chicca et al., 2012). Finally, the effects of WOBE437 on circulating ECs upon i.p. administration exhibited yet a different pattern leading to significant increase of 2-AG levels as compared to vehicle (after 15 min) but without affecting AEA levels (Chicca et al., 2017).

Selective Inhibition of Endocannabinoid Uptake Through WOBE437 Triggers Polypharmacological Effects in Inflammatory Pain To evaluate the preclinical potential of WOBE437, or in general of selective inhibition of the EC reuptake process, chronic inflammatory pain was induced by the intra-articular injection of CFA, with the subsequent development of monoarthritis-like conditions. Consecutive treatment for 3 days with 10 mg/kg of WOBE437 significantly attenuated allodynia and edema induced during monoarthritis. The allodynia was already reduced by single injection of 10 mg/kg of WOBE437. In models of CFA-induced persistent inflammatory pain, the antiallodynia effects of cannabinomimetics such as WIN55212-2, AM404 and ajulemic acid, have been previously shown to be mediated either via cannabinoid CB1 receptors or cannabinoid CB2 receptors (Li et al., 2017; Mitchell et al., 2007; Vann et al., 2007).

Moreover, both cannabinoid CB1 and CB2 receptors have shown to be involved in the antiallodynic effect of JZL195, a dual inhibitor of AEA and 2-AG degradation (Anderson et al., 2014), suggesting a pleotropic multi-target mechanism associated to the simultaneous increase of both AEA and 2-AG levels (Di Marzo and De Petrocellis, 2012; Pertwee, 2015; Pistis and O'Sullivan, 2017). Given the fact that WOBE437 inhibits the reuptake of both AEA and 2-AG, we wondered whether the pharmacological action resembles the one observed with JZL195, but with a different mechanism of action. Interestingly, the selective and independent blockage of either, CB1 receptor, CB2 receptor or PPARγ fully reversed the antiallodynic effect induced by the treatment with WOBE437 for 3 days. Similarly, the antiinflammatory effect of WOBE437 (3 days of treatment), measured by the reduction of the knee diameter (edema), was partially and independently reversed by all three receptor antagonists. However, in the single dose treatment with WOBE437, only the selective CB2 receptor antagonist SR144528 and the TRPV1 antagonist capsazepine were able to fully block the antiallodynic effect of WOBE437, while selective antagonists of CB1 receptor and PPARγ did not achieve a significant reduction. Because AEA is the endogenous TRPV1 agonist (Smart et al., 2000) and capsazepine was able to block the effect of WOBE437 in the single dose treatment we assume that the increase of AEA levels induced by WOBE437 in the somatosensory cortex caused the underlying pharmacology. Analgesic effects of TRPV1 agonist have been reported after central activation of TRPV1 receptor channels within the descending antinociceptive pathway (Mascarenhas et al., 2015; Starowicz et al., 2007a), which includes spinal and supraspinal structures, such as PAG and rostral ventromedial medulla (RVM). In addition, intrathecal or intra-PAG administration of AEA have shown to induce antinociceptive or antiallodynia effects through TRPV1 activation (Horvath et al., 2008; Maione et al., 2006; Starowicz et al., 2012). In the CFA monoarthritis model, TRPV1 have shown to mediate analgesic effects by integrating different stimuli (Szabó et al., 2005). In addition, the expression of TRPV1 in cortical neurons and their functional role in modulating synaptic activity was recently described in mice suffering from neuropathic pain (Marrone et al., 2017). Furthermore, it has been propose that intra-PAG administration of capsaicin induce an antinociceptive response involving the activation of presynaptic TRPV1 receptors in glutamatergic neurons, activation of postsynaptic mGlu5 receptors, release of 2-AG via diacylglycerol lipase activation, activation of presynaptic CB1 receptor and inhibition of GABA release, which leads to disinhibition of the descending pain inhibitory pathway (Liao et al., 2011). On the other hand, it has also been reported that high concentrations of AEA at the peripheral level leads to nociception or hyperalgesia via TRPV1 receptors on primary sensory neurons, while low concentrations leads to antinociception via CB1 receptor (Gauldie et al., 2001; Morisset et al., 2001; Starowicz et al., 2007b). According to this report, we assume an influence of the supraspinal TRPV1 receptors on the antiallodynia effects of WOBE437, rather than TRPV1 activation at the peripheral level. This hypothesis is in agreement with the present results, where AEA increases in the somatosensory cortex but decreases in plasma. It has been shown that subtle increments (1.2 to 1.5 times) in AEA levels in spinal cord or in PAG are enough to observe the antinociceptive or antiallodynia effects through TRPV1 activation (Maione et al., 2006; Starowicz et al., 2012). However, a proper measurement of AEA levels in the PAG and synovial tissue would be required to make any conclusions. Our data also show the involvement of CB2 receptors in the antiallodynic effect of WOBE437 which is fully prevented also by the selective CB2 receptor antagonist SR144528.

Activation of CB2 receptor has been shown to counteract inflammatory pain, e.g. in models of neuropathic pain (Davis, 2014; Klauke et al., 2014; Racz et al., 2008). Interestingly, upon single administration p.o., WOBE437 induced a significant increase of 2-AG level in plasma. Since 2-AG is considered the endogenous full agonist at CB2 receptors (Gonsiorek et al., 2000; Soethoudt et al., 2017), we can speculate that the antiallodynic effect observed after single administration of WOBE437 reflects the pleiotropic biological actions of both ECs, specifically through the activation of TRPV1 (AEA) and CB2 receptors (2-AG). In the 3 days WOBE437 treatment we could not use the TRPV1 antagonist capsazepine because the mice showed an unexpected hypersensitivity, which appeared to be caused by concomitant WOBE437 and capsazepine administration. Our data suggest that the potentiation of EC signaling obtained by blocking cellular EC reuptake, and potentially interfering with AEA trafficking in a bidirectional manner (vide infra), leads to alleviation of allodynia by a common potentially synergistic signaling pathway activated by cannabinoid CB2 and CB1 receptors, PPARγ and possibly TRPV1. On the other hand, the antiinflammatory effect seems to be associated to more than one mechanism of action in which activation of CB2 receptors is predominant. Thus, EC signaling through CB1 receptor and PPARγ activation might only partially contribute to the antiinflammatory effect in this mouse model of monoarthritis. Since WOBE437 after 3 days treatment did not influence transcription of CB receptors or the enzymes involved in the generation of ECs we excluded indirect effects on gene expression of the major proteins of the ECS.

A possible common signaling node activated by cannabinoid CB1, CB2 and PPARγ receptors could be at the transcriptional level. In animal models of adjuvant-induced arthritis, osteoarthritis and neuroinflammation, it has been observed that independent activation of CB2 receptor and PPARγ can inhibit the activation of the canonical transcription factor NF-κB (Fakhfouri et al., 2012; Saravanan et al., 2014) and the mitogen-activated protein kinases (MAPKs) (Li et al., 2013; Ma et al., 2015; Moens et al., 2013; Ribeiro et al., 2013). This inhibition attenuates the expression and final release of pro-inflammatory mediators such tumor necrosis factor-α, interleukin 1-β, but also iNOS and COX2 (Fakhfouri et al., 2012; Luo et al., 2014), which are associated with the pain sensitization and the edema formation seen after CFA injection (Khan et al., 2013; Li et al., 2013; Luo et al., 2014). On the other hand, activation of cannabinoid CB1 receptors can also modulate NF-κB and MAPKs pathways via upregulation of the transcriptional activity of PPARγ (Carroll et al., 2012; Du et al., 2011; Fakhfouri et al., 2012; Ignatowska-Jankowska et al., 2014). In addition, ECs have been shown to modulate the activation of PPARγ through three possible mechanisms: (1) direct binding/activation, (2) via metabolites generated after AEA and 2-AG degradation, or (3) via cannabinoid CB1/CB2 receptor-mediated downstream signaling (i.e. MAPKs) (Burstein, 2005; O'Sullivan, 2007; O'Sullivan and Kendall, 2010). Therefore, ECs might modulate the inflammatory stage in monoarthritic mice through the inhibition of NF-κB/MAPKs signaling pathways, as a plausible explanation of the indirect polypharmacological effects of WOBE437 after 3 days of treatment. Nevertheless, further experiments are necessary to understand the exact molecular mechanism. There are not direct reports about the involvement of PPARγ in the pharmacological effects of MAGL or FAAH inhibitors in vivo. However, in an in vitro model of neuroinflammation, the pharmacological effects of the MAGL inhibitor JZL184 and the FAAH inhibitor URB597 were shown to be mediated by PPARγ in a CB1 receptor-depended manner (Du et al., 2011). In addition, the antidyskinetic effects of URB597 in combination with capsazepine were reversed by a non-selective PPAR antagonist, and in the same model a PPARγ selective agonist showed a significant reduction of dyskinesia (Martinez et al., 2015). Conversely, in an acute model of carrageenan-induced inflammatory hyperalgesia, PPARα but not PPARγ was involved in the analgesic effects of URB597 (Jhaveri et al., 2008). These reports might suggest that PPARγ is primarily involved in chronic but not acute inflammatory conditions (Villapol, 2018). Thus, cannabinoid receptors and PPARγ may potentially constitute a synergic antiinflammatory signaling network. The pharmacological differences between WOBE437 and FAAH/MAGL inhibitors could involve tissue selectivity, the degree of increment in ECs levels and the differential extracellular EC accumulation leading to increased cannabinoid CB1 and CB2 receptor activation. However, the present data point towards a more complex action of WOBE437 as also the intracellular AEA receptors TRPV1 and PPARγ were involved in the analgesic effects of this EC reuptake inhibitor, accompanied by a weak but significant decrease of AEA in plasma. Therefore, we cannot exclude bidirectional transport effects in vivo as shown previously in vitro (Chicca et al., 2012; Nicolussi and Gertsch, 2015).

In conclusion, the novel EC reuptake inhibitor WOBE437 not only exhibits a high potency and selectivity (Chicca et al., 2017) but also matches the bioavailability criteria (in mice) that depict an adequate pharmacological tool compound. By applying WOBE437 in different mouse models of pain and inflammation, we found that the inhibition of EC reuptake triggers differential effects via elevation of ECs in different tissues and distinct pathophysiological/nociceptive contexts. This is in strong agreement with data obtained from the dual inhibition of AEA and 2-AG degradation (Anderson et al., 2014). Moreover, our data obtained with WOBE437 treatment reveal the noteworthy polypharmacology mediated by cannabinoid CB2, CB1, TRPV1 and PPARγ receptors in a mouse monoarthritis pain model. This indicates that this class of ECS modulators has the potential to exert therapeutic effects in chronic inflammatory conditions in which the pleiotropic effects of AEA and 2-AG counteract the pathophysiology. Therefore, selective EC reuptake inhibitors (SERIs) together with non-selective FAAH/MAGL inhibitors are promising indirect cannabimimetics and should be further investigated in preclinical models of chronic inflammatory pain.

What is claimed:

1. A compound represented by formula (I):

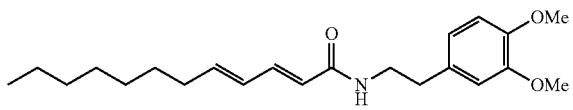 [SMILES: CCCCCCC/C=C/C=C/C(=O)NCCc1ccc(OC)c(OC)c1]

or a pharmaceutically acceptable solvate thereof.

2. A formulation, comprising the compound of claim 1 and a pharmaceutically acceptable excipient.

3. A method of treating a mammal suffering from a disease, disorder, or condition, the method comprising administering to said mammal a therapeutically effective amount of a compound represented by formula (I):

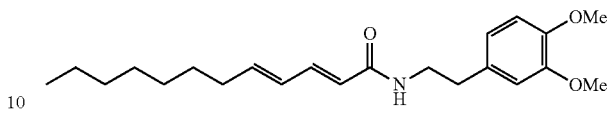

or a pharmaceutically acceptable solvate thereof;
wherein said disease, disorder, or condition is one or more of neuropathic pain, peripheral pain, persistent pain, inflammatory pain, or anxiety.

4. The method of claim 3, wherein said mammal is a primate, equine, canine or feline.

5. The method of claim 3, wherein said mammal is a human.

6. The method of claim 3, wherein said compound is administered orally, intravenously, sublingually, ocularly, transdermally, rectally, vaginally, topically, intramuscularly, subcutaneously, buccally or nasally.

7. The method of claim 3, wherein said compound is administered orally.

8. A method of treating a mammal suffering from a disease, illness or disorder associated with endocannabinoid reuptake, comprising:
administering to said mammal a therapeutically effective amount of a compound represented by formula (I):

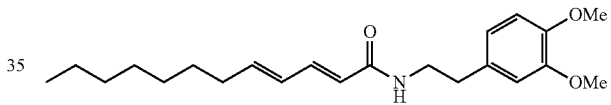

or a pharmaceutically acceptable solvate thereof;
wherein said disease, illness, or disorder is pain.

9. The method according to claim 8, wherein the endocannabinoid is at least one of anandamide or 2-arachidonoyl glycerol.

10. The method of claim 8, wherein said compound is administered orally.

11. The method of claim 8, wherein said mammal is a human.

12. The method according to claim 11, wherein the endocannabinoid is at least one of anandamide or 2-arachidonoyl glycerol.

13. The method of claim 11, wherein said compound is administered orally or topically.

14. The method of claim 3, wherein said disease, disorder, or condition is anxiety.

* * * * *